United States Patent [19]

Dorssers et al.

[11] Patent Number: 5,304,637
[45] Date of Patent: Apr. 19, 1994

[54] EXPRESSION AND PURIFICATION OF HUMAN INTERLEUKIN-3 AND MUTEINS THEREOF

[75] Inventors: Lambertus C. J. Dorssers, Randwijk; Gerard Wagemaker, Den Haag; Yvonne J. Vos, Capelle a/d IJssel; Robert W. Van Leen, Nijmegen; Maria L. N. Persoon, NA Leiden, all of Netherlands

[73] Assignee: Gist-brocades N.V., Delft, Netherlands

[21] Appl. No.: 494,182

[22] Filed: Mar. 13, 1990

Related U.S. Application Data

[63] Continuation-in-part of Ser. No. 249,184, Aug. 16, 1988, abandoned.

[30] Foreign Application Priority Data

Jul. 13, 1987 [NL] Netherlands ............... 87201322.2

[51] Int. Cl.$^5$ .............................................. C07K 3/28
[52] U.S. Cl. .................................... 530/351; 530/412; 530/413; 530/415; 530/417; 530/418; 530/419; 530/420; 435/69.5; 435/69.52; 930/141
[58] Field of Search .................. 530/351, 412–413, 530/415–417, 418–420; 435/69.5, 69.52

[56] References Cited

U.S. PATENT DOCUMENTS

| | | | |
|---|---|---|---|
| 4,419,446 | 12/1983 | Howley et al. | 435/69.1 |
| 4,959,455 | 9/1990 | Clark et al. | 530/351 |

FOREIGN PATENT DOCUMENTS

| | | |
|---|---|---|
| 0105141 | 4/1984 | European Pat. Off. |
| 0138133 | 4/1985 | European Pat. Off. |
| 0224294 | 6/1987 | European Pat. Off. |
| 0244042 | 11/1987 | European Pat. Off. |
| 0282185 | 11/1988 | European Pat. Off. |
| 8800598 | 1/1988 | PCT Int'l Appl. |
| 8804691 | 6/1988 | PCT Int'l Appl. |

OTHER PUBLICATIONS

Murthy et al., *Experimental Hematology*, 17, 1989, pp. 997–1003.
Yang et al., *Cell*, (1986), 47:3–10.
Dorssers et al., *Gene*, (1987), 55:115–124.
Law et al., *Proc. Natl. Acad. Sci. (U.S.A.)*, (1981), 78:2727–2731.
Lambert et al., *Ann. Rev. Genet.*, (1988), 22:235–258.
Ihle et al., *J. Immunol.*, (1982), 129:2431–2436.
Miyajima et al., *Gene*, (1987), 58:273–281.
Zilterner et al., *J. Biol. Chem.*, (1988), 263:14511–14517.
Clark-Lewis et al., *Science*, (1986), 231:134–139.
DeLamarter et al., *EMBO J.*, (1985), 4(10):2575–2581.
Dorssers et al., *Exp. Hematol.*, (1984), 12(6):357.
Fung et al., *Nature*, (1984), 307:233–237.
Garland et al., *Exp. Hematol.*, (1983), 11(8):757–761.
Hapel et al., *Blood*, (1985), 65(6):1453–1459.
Higashi et al., *J. Bio. Chem.*, (1983), 258(15):9522–9527.
Ihle et al., *Adv. Viral. Oncology*, (1984), 4:95–137.
Kinder et al., *Proc. Natl. Acad. Sci.*, (1986), 83:1001–1005.
Kriegler et al., *Blood*, (1982), 60(2):503–508.
Lemischka et al., *Cell*, (1986), 45:917–927.
March et al., *Nature*, (1985), 315:641–647.
Metcalf et al., *Blood*, (1986), 67(2):257–267.
Metcalf, *Brit. J. Hematol.*, (1986), 62:409–412.
Miyatake et al., *Proc. Natl. Acad. Sci.*, (1985), 82:316–320.
Schrader et al., *Proc. Natl. Acad. Sci.*, (1986), 83:2458–2462.
Shaw et al., *Cell*, (1986), 46:659–667.
van Bekkum et al., "Bone Marrow Transplantation: Biological Mechanisms and Clinical Practice", Marcel Dekker, Inc., New York, 1985, pp. 1–72.
Whetton et al., *TIBS*, May, 1986, pp. 207–211.
Yokota et al., *Adv. Gene Technol.*, (1985), 2:49–52.
Yokota et al., *Proc. Natl. Acad. Sci.*, (1984), 81:1070–1074.
Zwarthoff et al., *Nuc. Acid Res.*, (1985), 13(3):791–804.

*Primary Examiner*—Garnette D. Draper
*Attorney, Agent, or Firm*—Morrison and Foerster

[57] ABSTRACT

Methods are provided for improved production of hIL-3 either in glycosylated form from mammalian and yeast cells or in unglycosylated form from prokaryotes. Recombinantly produced human IL-3 is purified in a series of steps, initially employing hydrophobic interaction, followed by ion exchange chromatography and gel filtration.

18 Claims, 37 Drawing Sheets

```
            EcoRI SacI   KpnI SmaI BamHI XbaI SalI   PstI    SphI    HindIII
pTZ18R  gggaattcgagctcggtacccggggatcctctagagtcgacctgcaggcatgcaagcttg EcoRI SacI   EcoRV HindIII BglII      BamHI XbaI   SalI    PstI
pT1     gggaattcgagctcgatatcaagcttagatctcgagggggatcctctagagtcgacctgcag SphI         NdeI
        gcatgcaagctgcatatgcagcttg
```

FIG. 6 pGB/IL-301      Met Thr Met Ile Thr Asn Ser Arg Gly Ser Gly Pro
                atg acc atg att acg aat tcc cgg gga tct gGA CCA Glu Gln Asp Arg Val Pro Pro Ala Asp Pro Asn Met
                GAA CAA GAC AGA GTG CCT CCT GCC GAT CCA AAC ATG Ser Arg Leu Pro Val Leu Leu Leu Leu Gln Leu Leu
                AGC CGC CTG CCC GTC CTG CTC CTG CTC CAA CTC CTG Val Arg Pro Gly Leu Gln Ala¹Pro Met Thr Gln Thr
                GTC CGC CCC GGA CTC CAA GCT CCC ATG ACC CAG ACA Thr Pro Leu Lys Thr Ser Trp Val Asn Cys Ser Asn
                ACG CCC TTG AAG ACA AGC TGG GTT AAC TGC TCT AAC Met Ile Asp
                ATG ATC GAT pGB/IL-302      Met Thr Met Ile Thr Asn Ser Arg Gly Ser Ser Arg
                atg acc atg att acg aat tcc cgg gga tcc tct aga Val Asp Pro²Met Thr Gln Thr Thr Pro Leu Lys Thr
                gtc gac CCC ATG ACC CAG ACA ACG CCC TTG AAG ACA Ser Arg Val Asn Cys Ser Asn Met Ile Asp
                AGC CGG GTT AAC TGC TCT AAC ATG ATC GAT pGB/IL-303      Met Thr Met Ile Thr Asn Ser Arg Gly Ser Ser Arg
                atg acc atg att acg aat tcc cgg gga tcc tct aga Val Asp Pro²Met Thr Gln Thr Thr Pro Pro Lys Thr
                gtc gac CCC ATG ACC CAG ACA ACG CCC CCG AAG ACA Ser Arg Val Asn Cys Ser Asn Met Ile Asp
                AGC CGG GTT AAC TGC TCT AAC ATG ATC GAT pGB/IL-304      Met Thr Met Ile Thr Asn Leu Ile Arg Leu Thr Ile
                atg acc atg att acg aat tta ata cga ctc act ata Gly Asn Ser Ser Ser Val Pro Gly Asp Pro Leu Glu
                ggg aat tcg agc tcg gta ccc ggg gat cct cta gag Ser Ile Asp Pro²Thr Thr Glu Thr Thr Pro Leu Lys
                tcg atc gac CCC ACG ACC CAG ACA ACG CCC CTG AAG Thr Ser Trp Val Asn Cys Ser Asn Met Ile Asp
                ACA AGC TGG GTT AAC TGC TCT AAC ATG ATC GAT

FIG. 8A pGB/IL-305

Met Thr Met Ile Thr Asn Leu Ile Arg Leu Thr Ile
atg acc atg att acg aat tta ata cga ctc act ata Gly Asn Ser Ser Ser Val Pro Gly Asp Pro Leu Glu
ggg aat tcg agc tcg gta ccc ggg gat cct cta gag Asn$^{15}$ Cys Ser Asn Met Ile Asp
AAC TGC TCT AAC ATG ATC GAT pGB/IL-306

Met Ala$^{1}$ Pro Met Thr Gln Thr Thr Pro Leu Lys Thr
atg GCT CCC ATG ACC CAG ACA ACG CCC TTG AAG ACA Ser Trp Val Asn Cys Ser Asn Met Ile Asp
AGC TGG GTT AAC TGC TCT AAC ATG ATC GAT

FIG. 8B

*Sequence of the N-terminus of the fusion protein:

Met Ser Tyr Ala Val Cys Arg Met Glu Lys

Val Lys Ser Gly Val Pro Ser Ser Asn Ser Gly

Pro Glu Gln Asp Arg Val Pro Pro Ala Asp Pro

Asn Met Ser Arg Leu ......... Ala Pro .......
    -19↑                           +1↑
    hIL-3 signal sequence          hIL-3 mature sequence pIL-3: precursor gene human IL-3.

```
        10         20         30         40         50         60         70
AATTCACCTCGAAAGCAAGCTGATAAACCGATACAATTAAAGGCTCCTTTTGGAGCCTTTTTTTTTGGAGATTTT
        80         90        100        110        120        130        140        150
CAACGTGAAAAAATTATTATTCGCAATTCCAAGCTAATTCACCTCGAAAGCAAGCTGATAAACCGATACAATTAA
       160        170        180        190        200        210        220
AGGCTCCTTTTGGAGCCTTTTTTTTTGGAGATTTTCAACGTGAAAAAATTATTATTCGCAATTCCAAGCTCTGCC
       230        240        250        260        270        280        290        300
TCGCGCGTTTCGGTGATGACGGTGAAAACCTCTGACACATGCAGCTCCCGGAGACGGTCACAGCTTGTCTGTAAG
       310        320        330        340        350        360        370
CGGATGCAGATCACGCGCCCTGTAGCGGCGCATTAAGCGCGGCGGGTGTGGTGGTTACGCGCAGCGTGACCGCTA
       380        390        400        410        420        430        440        450
CACTTGCCAGCGCCCTAGCGCCCGCTCCTTTCGCTTTCTTCCCTTCCTTTCTCGCCACGTTCGCCGGCTTTCCCC
       460        470        480        490        500        510        520
GTCAAGCTCTAAATCGGGGGCTCCCTTTAGGGTTCCGATTTAGTGCTTTACGGCACCTCGACCCCAAAAAACTTG
       530        540        550        560        570        580        590        600
ATTAGGGTGATGGTTCACGTAGTGGGCCATCGCCCTGATAGACGGTTTTTCGCCCTTTGACGTTGGAGTCCACGT
       610        620        630        640        650        660        670
TCTTTAATAGTGGACTCTTGTTCCAAACTGGAACAACACTCAACCCTATCTCGGTCTATTCTTTTGATTTATAAG
       680        690        700        710        720        730        740        750
GGATTTTGCCGATTTCGGCCTATTGGTTAAAAAATGAGCTGATTTAACAAAAATTTAACGCGAATTTTAACAAAA
       760        770        780        790        800        810        820
TATTAACGTTTACAATTTGATCTGCGCTCGGTCGTTCGGCTGCGGCGAGCGGTATCAGCTCACTCAAAGGCGGTA
       830        840        850        860        870        880        890        900
ATACGGTTATCCACAGAATCAGGGGATAACGCAGGAAAGAACATGTGAGCAAAAGGCCAGCAAAAGGCCAGGAAC
       910        920        930        940        950        960        970
CGTAAAAAGGCCGCGTTGCTGGCGTTTTTCCATAGGCTCCGCCCCCCTGACGAGCATCACAAAAATCGACGCTCA
       980        990       1000       1010       1020       1030       1040       1050
AGTCAGAGGTGGCGAAACCCGACAGGACTATAAAGATACCAGGCGTTTCCCCCTGGAAGCTCCCTCGTGCGCTCT
      1060       1070       1080       1090       1100       1110       1120
CCTGTTCCGACCCTGCCGCTTACCGGATACCTGTCCGCCTTTCTCCCTTCGGGAAGCGTGGCGCTTTCTCAATGC
      1130       1140       1150       1160       1170       1180       1190       1200
TCACGCTGTAGGTATCTCAGTTCGGTGTAGGTCGTTCGCTCCAAGCTGGGCTGTGTGCACGAACCCCCCGTTCAG
      1210       1220       1230       1240       1250       1260       1270
CCCGACCGCTGCGCCTTATCCGGTAACTATCGTCTTGAGTCCAACCCGGTAAGACACGACTTATCGCCACTGGCA
      1280       1290       1300       1310       1320       1330       1340       1350
GCAGCCACTGGTAACAGGATTAGCAGAGCGAGGTATGTAGGCGGTGCTACAGAGTTCTTGAAGTGGTGGCCTAAC
```

FIG.17A

```
       1360      1370      1380      1390      1400      1410      1420
TACGGCTACACTAGAAGGACAGTATTTGGTATCTGCGCTCTGCTGAAGCCAGTTACCTTCGGAAAAAGAGTTGGT
   1430      1440      1450      1460      1470      1480      1490      1500
AGCTCTTGATCCGGCAAACAAACCACCGCTGGTAGCGGTGGTTTTTTTGTTTGCAAGCAGCAGATTACGCGCAGA
   1510      1520      1530      1540      1550      1560      1570
AAAAAAGGATCTCAAGAAGATCCTTTGATCTTTTCTACGGGGTCTGACGCTCAGTGGAACGAAAACTCACGTTAA
   1580      1590      1600      1610      1620      1630      1640      1650
GGGATTTTGGTCATGAGATTATCAAAAAGGATCTTCACCTAGATCCTTTTAAATTAAAAATGAAGTTTTAAATCA
   1660      1670      1680      1690      1700      1710      1720
ATCTAAAGTATATATGAGTAAACTTGGTCTGACAGTTACCAATGCTTAATCAGTGAGGCACCTATCTCAGCGATC
   1730      1740      1750      1760      1770      1780      1790      1800
TGTCTATTTCGTTCATCCATAGTTGCCTGACTCCCCGTCGTGTAGATAACTACGATACGGGAGGGCTTACCATCT
   1810      1820      1830      1840      1850      1860      1870
GGCCCCAGTGCTGCAATGATACCGCGAGACCCACGCTCACCGGCTCCAGATTTATCAGCAATAAACCAGCCAGCC
   1880      1890      1900      1910      1920      1930      1940      1950
GGAAGGGCCGAGCGCAGAAGTGGTCCTGCAACTTTATCCGCCTCCATCCAGTCTATTAATTGTTGCCGGGAAGCT
   1960      1970      1980      1990      2000      2010      2020
AGAGTAAGTAGTTCGCCAGTTAATAGTTTGCGCAACGTTGTTGCCATTGCTGCAGGCATCGTGGTGTCACGCTCG
   2030      2040      2050      2060      2070      2080      2090      2100
TCGTTTGGTATGGCTTCATTCAGCTCCGGTTCCCAACGATCAAGGCGAGTTACATGATCCCCCATGTTGTGCAAA
   2110      2120      2130      2140      2150      2160      2170
AAAGCGGTTAGCTCCTTCGGTCCTCCGATCGTTGTCAGAAGTAAGTTGGCCGCAGTGTTATCACTCATGGTTATG
   2180      2190      2200      2210      2220      2230      2240      2250
GCAGCACTGCATAATTCTCTTACTGTCATGCCATCCGTAAGATGCTTTTCTGTGACTGGTGAGTACTCAACCAAG
   2260      2270      2280      2290      2300      2310      2320
TCATTCTGAGAATAGTGTATGCGGCGACCGAGTTGCTCTTGCCCGGCGTCAACACGGGATAATACCGCGCCACAT
   2330      2340      2350      2360      2370      2380      2390      2400
AGCAGAACTTTAAAAGTGCTCATCATTGGAAAACGTTCTTCGGGGCGAAAACTCTCAAGGATCTTACCGCTGTTG
   2410      2420      2430      2440      2450      2460      2470
AGATCCAGTTCGATGTAACCCACTCGTGCACCCAACTGATCTTCAGCATCTTTTACTTTCACCAGCGTTTCTGGG
   2480      2490      2500      2510      2520      2530      2540      2550
TGAGCAAAAACAGGAAGGCAAAATGCCGCAAAAAAGGGAATAAGGGCGACACGGAAATGTTGAATACTCATACTC
   2560      2570      2580      2590      2600      2610      2620
TTCCTTTTTCAATATTATTGAAGCAGACAGTTTTATTGTTCATGATGATATATTTTTATCTTGTGCAATGTAACA
   2630      2640      2650      2660      2670      2680      2690      2700
TCAGAGATTTTGAGACACAACGTGGCTTTGTTGAATAAATCGAACTTTTGCTGAGTTGACTCCCCGCGCGCGATG
```

FIG.17B

```
      2710      2720      2730      2740      2750      2760      2770
GGTCGAATTTGCTTTCGAAAAAAAAGCCCGCTCATTAGGCGGGCTAAAAAAAAGCCCGCTCATTAGGCGGGCTCG
      2780      2790      2800      2810      2820      2830      2840      2850
AATTTCTGCCATTCATCCGCTTATTATCACTTATTCAGGCGTAGCAACCAGGCGTTTAAGGGCACCAATAACTGC
      2860      2870      2880      2890      2900      2910      2920
CTTAAAAAAATTACGCCCCGCCCTGCCACTCATCGCAGTACTGTTGTAATTCATTAAGCATTCTGCCGACATGGA
      2930      2940      2950      2960      2970      2980      2990      3000
AGCCATCACAGACGGCATGATGAACCTGAATCGCCAGCGGCATCAGCACCTTGTCGCCTTGCGTATAATATTTGC
      3010      3020      3030      3040      3050      3060      3070
CCATAGTGAAAACGGGGGCGAAGAAGTTGTCCATATTCGCCACGTTTAAATCAAAACTGGTGAAACTCACCCAGG
      3080      3090      3100      3110      3120      3130      3140      3150
GATTGGCTGAGACGAAAAACATATTCTCAATAAACCCTTTAGGGAAATAGGCCAGGTTTTCACCGTAACACGCCA
      3160      3170      3180      3190      3200      3210      3220
CATCTTGCGAATATATGTGTAGAAACTGCCGGAAATCGTCGTGGTATTCACTCCAGAGCGATGAAAACGTTTCAG
      3230      3240      3250      3260      3270      3280      3290      3300
TTTGCTCATGGAAAACGGTGTAACAAGGGTGAACACTATCCCATATCACCAGCTCACCGTCTTTCATTGCCATAC
      3310      3320      3330      3340      3350      3360      3370
GAAATTCCGGATGAGCATTCATCAGGCGGGCAAGAATGTGAATAAAGGCCGGATAAAACTTGTGCTTATTTTTCT
      3380      3390      3400      3410      3420      3430      3440      3450
TTACGGTCTTTAAAAAGGCCGTAATATCCAGCTAAACGGTCTGGTTATAGGTACATTGAGCAACTGACTGAAATG
      3460      3470      3480      3490      3500      3510      3520
CCTCAAAATGTTCTTTACGATGCCATTGGGATATATCAACGGTGGTATATCCAGTGATTTTTTTCTCCATTTTAG
      3530      3540      3550      3560      3570      3580      3590      3600
CTTCCTTAGCTCCTGAAAATCTCGATAACTCAAAAAATACGCCCGGTAGTGATCTTATTTCATTATGGTGAAAGT
      3610      3620      3630      3640      3650      3660      3670
TGGAACCTCTTACGTGCCGATCAACGTCTCATTTTCGCCAAAAGTTGGCCCAGGGCTTCCCGGTATCAACAGGGA
      3680      3690      3700      3710      3720      3730      3740      3750
CACCAGGATTTATTTATTCTGCGAAGTGATCTTCCGTCACAGGTATTTATTCGAAGACGAAAGGGCATCGCGCGC
      3760      3770      3780      3790      3800      3810      3820
GGGGAATTCCCGGGAGAGCTCGATATCGCATGCGGTACCTCTAGAAGAAGCTTGGAGACAAGGTAAAGGATAAAA
      3830      3840      3850      3860      3870      3880      3890      3900
CAGCACAATTCCAAGAAAAACACGATTTAGAACCTAAAAAGAACGAATTTGAACTAACTCATAACCGAGAGGTAA
      3910      3920      3930      3940      3950      3960      3970
AAAAAGAACGAAGTCGAGATCAGGGAATGAGTTTATAAAATAAAAAAAGCACCTGAAAAGGTGTCTTTTTTTGAT
      3980      3990      4000      4010      4020      4030      4040      4050
GGTTTTGAACTTGTTCTTTCTTATCTTGATACATATAGAAATAACGTCATTTTTATTTTAGTTGCTGAAAGGTGC
```

FIG.17C

```
      4060      4070      4080      4090      4100      4110      4120
GTTGAAGTGTTGGTATGTATGTGTTTTAAAGTATTGAAAACCCTTAAAATTGGTTGCACAGAAAAACCCCATCTG
    4130      4140      4150      4160      4170      4180      4190      4200
TTAAAGTTATAAGTGACTAAACAAATAACTAAATAGATGGGGGTTTCTTTTAATATTATGTGTCCTAATAGTAGC
      4210      4220      4230      4240      4250      4260      4270
ATTTATTCAGATGAAAAATCAAGGGTTTTAGTGGACAAGACAAAAAGTGGAAAAGTGAGACCATGGAGAGAAAAG
    4280      4290      4300      4310      4320      4330      4340      4350
AAAATCGCTAATGTTGATTACTTTGAACTTCTGCATATTCTTGAATTTAAAAAGGCTGAAAGAGTAAAAGATTGT
    4360      4370      4380      4390      4400      4410      4420
GCTGAAATATTAGAGTATAAACAAAATCGTGAAACAGGCGAAAGAAAGTTGTATCGAGTGTGGTTTTGTAAATCC
    4430      4440      4450      4460      4470      4480      4490      4500
AGGCTTTGTCCAATGTGCAACTGGAGGAGAGCAATGAAACATGGCATTCAGTCACAAAAGGTTGTTGCTGAAGTT
    4510      4520      4530      4540      4550      4560      4570
ATTAAACAAAAGCCAACAGTTCGTTGGTTGTTTCTCACATTAACAGTTAAAAATGTTTATGATGGCGAAGAATTA
    4580      4590      4600      4610      4620      4630      4640      4650
AATAAGAGTTTGTCAGATATGGCTCAAGGATTTCGCCGAATGATGCAATATAAAAAAATTAATAAAAATCTTGTT
    4660      4670      4680      4690      4700      4710      4720
GGTTTTATGCGTGCAACGGAAGTGACAATAAATAATAAAGATAATTCTTATAATCAGCACATGCATGTATTGGTA
    4730      4740      4750      4760      4770      4780      4790      4800
TGTGTGGAACCAACTTATTTTAAGAATACAGAAAACTACGTGAATCAAAAACAATGGATTCAATTTTGGAAAAAG
    4810      4820      4830      4840      4850      4860      4870
GCAATGAAATTAGACTATGATCCAAATGTAAAAGTTCAAATGATTCGACCGAAAAATAAATATAAATCGGATATA
    4880      4890      4900      4910      4920      4930      4940      4950
CAATCGGCAATTGACGAAACTGCAAAATATCCTGTAAAGGATACGGATTTTATGACCGATGATGAAGAAAAGAAT
    4960      4970      4980      4990      5000      5010      5020
TTGAAACGTTTGTCTGATTTGGAGGAAGGTTTACACCGTAAAAGGTTAATCTCCTATGGTGGTTTGTTAAAAGAA
  5030      5040      5050      5060      5070      5080      5090      5100
ATACATAAAAAATTAAACCTTGATGACACAGAAGAAGGCGATTTGATTCATACAGATGATGACGAAAAAGCCGAT
    5110      5120      5130      5140      5150      5160      5170
GAAGATGGATTTTCTATTATTGCAATGTGGAATTGGGAACGGAAAAATTATTTTATTAAAGAGTAGTTCAACAAA
  5180      5190      5200      5210      5220      5230      5240      5250
CGGGCCAGTTTGTTGAAGATTAGATGCTATAATTGTTATTAAAAGGATTGAAGGATGCTTAGGAAGACGAGTTAT
      5260      5270      5280      5290      5300      5310      5320
TAATAGCTGAATAAGAACGGTGCTCTCCAAATATTCTTATTTAGAAAAGCAAATCTAAAATTATCTGAAAAGGGA
  5330      5340      5350      5360      5370      5380      5390      5400
ATGAGAATAGTGAATGGACCAATAATAATGACTAGAGAAGAAAGAATGAAGATTGTTCATGAAATTAAGGAACGA
```

FIG. 17D

```
      5410      5420      5430      5440      5450      5460      5470
ATATTGGATAAATATGGGGATGATGTTAAGGCTATTGGTGTTTATGGCTCTCTTGGTCGTCAGACTGATGGGCCC
   5480      5490      5500      5510      5520      5530      5540      5550
TATTCGGATATTGAGATGATGTGTGTCATGTCAACAGAGGAAGCAGAGTTCAGCCATGAATGGACAACCGGTGAG
      5560      5570      5580      5590      5600      5610      5620
TGGAAGGTGGAAGTGAATTTTGATAGCGAAGAGATTCTACTAGATTATGCATCTCAGGTGGAATCAGATTGGCCG
   5630      5640      5650      5660      5670      5680      5690      5700
CTTACACATGGTCAATTTTTCTCTATTTTGCCGATTTATGATTCAGGTGGATACTTAGAGAAAGTGTATCAAACT
      5710      5720      5730      5740      5750      5760      5770
GCTAAATCGGTAGAAGCCCAAACGTTCCACGATGCGATTTGTGCCCTTATCGTAGAAGAGCTGTTTGAATATGCA
   5780      5790      5800      5810      5820      5830      5840      5850
GGCAAATGGCGTAATATTCGTGTGCAAGGACCGACAACATTTCTACCATCCTTGACTGTACAGGTAGCAATGGCA
      5860      5870      5880      5890      5900      5910      5920
GGTGCCATGTTGATTGGTCTGCATCATCGCATCTGTTATACGACGAGCGCTTCGGTCTTAACTGAAGCAGTTAAG
   5930      5940      5950      5960      5970      5980      5990      6000
CAATCAGATCTTCCTTCAGGTTATGACCATCTGTGCCAGTTCGTAATGTCTGGTCAACTTTCCGACTCTGAGAAA
      6010      6020      6030      6040      6050      6060      6070
CTTCTGGAATCGCTAGAGAATTTCTGGAATGGGATTCAGGAGTGGACAGAACGACACGGATATATAGTGGATGTG
   6080      6090      6100      6110      6120      6130      6140      6150
TCAAAACGCATACCATTTTGAACGATGACCTCTAATAATTGTTAATCATGTTGGTTACGTATTTATTAACTTCTC
      6160      6170      6180      6190      6200      6210      6220
CTAGTATTAGTAATTATCATGGCTGTCATGGCGCATTAACGGAATAAAGGGTGTGCTTAAATCGGGCCATTTTGC
   6230      6240      6250      6260      6270      6280      6290      6300
GTAATAAGAAAAAGGATTAATTATGAGCGAATTGAATTAATAATAAGGTAATAGATTTACATTAGAAAATGAAAG
      6310      6320      6330      6340      6350      6360      6370
GGGATTTTATGCGTGAGAATGTTACAGTCTATCCCGGCATTGCCAGTCGGGGATATTAAAAAGAGTATAGGTTTT
   6380      6390      6400      6410      6420      6430      6440      6450
TATTGCGATAAACTAGGTTTCACTTTGGTTCACCATGAAGATGGATTCGCAGTTCTAATGTGTAATGAGGTTCGG
      6460      6470      6480      6490      6500      6510      6520
ATTCATCTATGGGAGGCAAGTGATGAAGGCTGGCGCTCTCGTAGTAATGATTCACCGGTTTGTACAGGTGCGGAG
   6530      6540      6550      6560      6570      6580      6590      6600
TCGTTTATTGCTGGTACTGCTAGTTGCCGCATTGAAGTAGAGGGAATTGATGAATTATATCAACATATTAAGCCT
      6610      6620      6630      6640      6650      6660      6670
TTGGGCATTTTGCACCCCAATACATCATTAAAAGATCAGTGGTGGGATGAACGAGACTTTGCAGTAATTGATCCC
   6680      6690      6700      6710      6720      6730      6740      6750
GACAACAATTTGATTAGCTTTTTTCAACAAATAAAAAGCTAAAATCTATTATTAATCTGTTCAGCAATCGGGCGC
```

FIG.17E

```
        6760      6770      6780      6790      6800      6810      6820
GATTGCTGAATAAAAGATACGAGAGACCTCTCTTGTATCTTTTTTATTTTGAGTGGTTTTGTCCGTTACACTAGA
     6830      6840      6850      6860      6870      6880      6890      6900
AAACCGAAAGACAATAAAAATTTTATTCTTGCTGAGTCTGGCTTTCGGTAAGCTAGACAAAACGGACAAAATAAA
     6910      6920      6930      6940      6950      6960      6970
AATTGGCAAGGGTTTAAAGGTGGAGATTTTTTGAGTGATCTTCTCAAAAAATACTACCTGTCCCTTGCTGATTTT
     6980      6990      7000      7010      7020      7030      7040      7050
TAAACGAGCACGAGAGCAAAACCCCCCTTTGCTGAGGTGGCAGAGGGCAGGTTTTTTTGTTTCTTTTTTCTCGTA
      7060      7070      7080      7090      7100      7110      7120
AAAAAAAGAAAGGTCTTAAAGGTTTTATGGTTTTGGTCGGCACTGCCGACAGCCTCGCAGGACACACACTTTATG
     7130      7140      7150      7160      7170      7180      7190      7200
AATATAAAGTATAGTGTGTTATACTTTACTTGGAAGTGGTTGCCGGAAAGAGCGAAAATGCCTCACATTTGTGCC
       7210      7220      7230      7240      7250      7260      7270
ACCTAAAAAGGAGCGATTTACATATGAGTTATGCAGTTTGTAGAATGCAAAAAGTGAAATCAGGGGGATCCTCTA
     7280      7290      7300      7310      7320      7330
GAGTCGAGCTCAAGCTAGCTTGGTACGTACCAGATCTGAGATCACGCGTTCTAGAGGTCGA
```

FIG. 17F

Sequence:

Hpall promoter-AAAGGAGCGATTTACAT ATG AGT
                    ── S.D. ──           met ser TAT GCA GTT TGT AGA ATG CAA AAA GTG
tyr ala val cys arg met gln lys val ── S.D. ──
AAA TCA GGG GGA TCC AAG GAG GTG ATC
lys ser gly gly ser lys glu val ile TAG AGT CGA CATG...pIL-3
stop        met

```
      4466                4486                4506                4526                4546                4556
CCGCGGGAT CGACTCATAA AATAGTAACC TTCTAATGCG TATCTATTGA CTACCAACCA TTAGTGTGGT TGCAGAAGGC GGAATTCTCC CTTCTTCGAA
      4566                4586                4606                4626                4646                4656
TTCAGCTTGC TTTTCATTTT TATTTTCCAT TTTTCAGTTT TTGTTTGTGT CGAATTTAGC CAGTTGCTTC TCCAAGATGA AAAAACCCCT GCGCAGTTTC
      4666                4686                4706                4726                4746                4756
TGTGTGCAA GATCCTAATC GACTTTTCCA CCCCCACAA AAGTAAATGT TTCTTTGTTA CATTCGGCGTG GGTAGCTAGC TCCCCGAATC TCAAAGGACT
      4766                4786                4806                4826                4846                4856
TAGGGACTGC ACTACATCAG AGTGTGTTCA CCTGGTTTGC TGCCTGGTTT GAAAGAAAAG AGCGGGAACT CGGCGGTTCC CGGCGAATAA TCATGCGATA
      4866                4886                4906                4926                4946                4956
GTCCTTTGGC CTTCCAAGTC GCATGTAGAG TAGACAACAG CAGGGAGGG CTTTCACTGA GATCCTGTAT CTTGTTGGGT AAGTCGGATG
      4966                4986                5006                5026                5046                5056
AAAGGGAAT CGTATGAGAT TGGAGAGGAT GCGGAAGAGG TAACGCCTTT TGTTAACTTG TTTAATTATT ATGGGCAGG CGAGAGGGG AGGAATGTAT
      5066                5086                5106                5126                5146                5156
GTGTGTGAGG CGGGCGAGAC GGAGCCATCC AGGCCAGGTA GAAATAGAGA AAGCCGAATG TTAGACAATA TGGCAGCGTA GTAGAGTAGG TAGGTAGGCA
      5166                5186                5206                5226                5246                5256
AGTACTGCTA GCAAAGAGGA GAAGGGTAAG CTCACTCTTC GCATTCCACA CCGTTAGTGT GTCAGTTTAG ACAAAAAAAC AACTACTATA CCAATTAGTA
      5266                5286                5306                5326                5346                5356
GACTGTGAAC TGACTTTTGG AACGGCTTTT CGGACTGCGA TTATTCGTGA GGAATCAAGG GTCATATTTA CGGACAACAG TGGGTGATTC
      5366                5386                5406                5426                5446                5456
CCATATGGAG TAGGAAAACG AGATCATGGT ATCCTCAGAT ATGTTGCGGA ATTCTGTTCA CCGCAAAGTT CAGGGTGCTC TGGTGGTTT CGGTTGGTCT
      5466                5486                5506                5526                5546                5556
TTGCTTTGCT TCTCCCTTGT CTTGCATGTT AATAATAGCC TAGCCTGTGA GCCGAAACTT AGGGTAGGCT TAGTGTTGGA ACGTACATAT GTATCACGTT
      5566                5586                5606                5626                5646                5656
GACTTGGTTT AACCAGGCGA CCTGGTAGCC AGCCATACCC ACACACGTTT TTTGTATTCT TCAGTATAGT TGTGAAAAGT GTAGCGGAAA TATGTGGTCC
      5666                5686                5706                5726                5746                5756
GAGCAACAGC GTCTTTTTCT AGTAGTGCGG TCGGTTACTT GGTTGACATT GGTATTTGGA CTTTGTTGCT ACACCATTCA CTACTTGAAG TCGAGTGTGA
      5766                5786                5806                5826                5846                5856
AGGGTATGAT TTCTAGTGGT GAACACCTTT AGTTACGTAA TGTTTTCATT GCTGTTTTAC TTGAGATTTC GATTGAGAAA AAGGTATTTA ATAGCTCGAA
```

FIG.22A

```
      5866        5876        5889        5896        5906        5916        5926        5936        5946        5956
TCAATGTGTT ATCATTGTGA AGATGTTCTT CCCTAACTCG AAAGGTATAT GAGGCTTGTG TTTCTTAGGA GAATTATTAT TCTTTTGTTA TGTTGCGCTT
      5966        5976        5986        5996        6006        6016        6026        6036        6046        6056
GTAGTTGGAA AAGGTGAAGA GACAAAAGCT TAACACTTGA AATTTAGGAA AGAGCAGAAT TTGGCAAAAA AAATAAAACA AAATAAACA CGTCGACTTG
      6066        6076        6086        6096        6106        6116        6126        6136        6146        6156
TGAGCGGATA ACAATCGACA CATACTCATC GAGAACTGAA AGATATGAGA TTTCCATCGA TTTTTACTGC AGTTTTATTC GCAGCATCCT CCGCATTAGC
      6166        6176        6186        6196        6206        6216        6226        6236        6246        6256
TGCTCCAGTC AACACTACAA CAGAAGATGA AACGGCACAA ATTCCGGCTG AAGCTGTCAT CGGTTACTTA GATTTAGAAG GGGATTTCGA TGTTGCTGTT
      6266        6276        6286        6296        6306        6316        6326        6336        6346        6356
TTGCCATTTT CCAACAGCAC AAATAACGGG TTATTGTTTA TAAATACTAC TATTGCCAGC ATTGCTGCTA AAGAAGAAGG GGTATCTCTA GATAAAAGAG
      6366        6376        6386        6396        6406        6416        6426        6436        6446        6456
CTCCCATGAC CCAGACAACG CCCTTGAAGA CAAGCTGGGT TAACTGCTCT AACATGATCG ATGAAATTAT AACACACTTA AAGCAGCCAC CTTTGCCTTT
      6466        6476        6486        6496        6506        6516        6526        6536        6546        6556
GCTGGACTTC AACAACCTCA ATGGGGAAGA CCAAGACATT CTGATGGAAA ATAACCTTCG AAGGCCAAAC CTGGAGGCAT TCAACAGGGC TGTCAAGAGT
      6566        6576        6586        6596        6606        6616        6626        6636        6646        6656
TTACAGAACG CATCAGCAAT TGAGAGCATT CTTAAAAATC TCCTGCCATG TCTGCCCCTG GCCACGGCCG CACCCACGCG ACATCCAATC CATATCAAGG
      6666        6676        6686        6696        6706        6716        6726        6736        6746        6756
ACGGTGACTG GAATGAATTC CGGAGGAAAC TGACGTTCTA TCTGAAAACC CTTGAGAATG CGCAGGCTCA ACAGACGACT TCTGAAACCT TTGAGCCTCG CGATCTTTTG
      6766        6776        6786        6796        6806        6816        6826        6836        6846        6856
AGTCCAACGT CCAGCTCGTT CTCTGGGCCT TCTCACCACA GAGCCTCGGG ACATCAAAAA CAGCAGAACT TCTGAAACCT CTGGTCATC TCTCACACAT
      6866        6876        6886        6896        6906        6916        6926        6936        6946        6956
TCCAGGACCA GAAGCATTTC ACCTTTTCCT GCGGCATCAG ATGAATTGTT AATTATCTAA TTTCTGAAAT GTGCAGCTCC CATTTGGCCT TGTGCGGTTG
      6966        6976        6986        6996        7006        7016        7026        7036        7046        7056
TGTTCTCATT TTTATCCCAT TGAGACTATT TATTTATGTA TATTTATTTA TTGCCTGGAG TGTGAACTGT ATTTATTTTA GCAGAGGAGC
      7066        7076        7086        7096        7106        7116        7126        7136        7146        7156
CATGTCCTGC TGCTTCTGCA AAAAACTCAG AGTGGGGTGG GGAGCATGTT CATTTGTACC TCGAGAATTT ATACTTAGAT AAGTATGTAC TTACAGGTAT
      7166        7176        7186        7196
ATTTCTATGA GATACTGATG TATACATGCA TGATAATATT TAAAGCTT
```

FIG.22B

```
4466       4476       4486       4496       4506       4516       4526       4536       4546       4556
CCGCGGGAT CGACTCATAA AATAGTAACC TTCTAATGCG TATCTATTGA CTACCAACCA TTAGTGTGGT TGCAGAAGGC GGAATTCTCC CTTCTTCGAA
4566       4576       4586       4596       4606       4616       4626       4636       4646       4656
TTCAGCTTGC TTTTCATTTT TATTTTCCAT TTTTCAGTTT TTGTTTGTGT CGAATTTAGC CAGTTGCTTC TCCAAGATGA AAAAACCCCT GCGCAGTTTC
4666       4676       4686       4696       4706       4716       4726       4736       4746       4756
TGTGTCGCAA GATCCTAATC GACTTTTCCA CCCCCCACAA AAGTAAATGT TTCTTTGTTA CATTCGCGTG GGTAGCTAGC TCCCCGAATC TCAAAGGACT
4766       4776       4786       4796       4806       4816       4826       4836       4846       4856
TAGGGACTGC ACTACATCAG AGTGTGTTCA CCTGGTTTGC TGCCTGGTTT GAAAGAAAAG AGCGGGAACT CGGGGTTCC CGGCGAATAA TCATGCGATA
4866       4876       4886       4896       4906       4916       4926       4936       4946       4956
GTCCTTTGGC CTTCCAAGTC GCATGTAGAG TAGACAACAG ACAGGGAGGG CAGGAAGGAT CTTTCACTGA GATCCTGTAT CTTGTTGGGT AAGTCGGATG
4966       4976       4986       4996       5006       5016       5026       5036       5046       5056
AAAGGGAAT CGTATGAGAT TGGAGAGGAT GCGGAAGAGG TAACGCCTTT TGTTAACTTG TTTAATTATT ATGGGGCAGG CGAGAGGGGG AGGAATGTAT
5066       5076       5086       5096       5106       5116       5126       5136       5146       5156
GTGTGTGAGG CGGGCGAGAC GGAGCCATCC AGGCCAGGTA GAAATAGAGA AAGCCGAATG TTAGACAATA TGGCAGCGTA GTAGAGTAGG TAGGTAGGCA
5166       5176       5186       5196       5206       5216       5226       5236       5246       5256
AGTACTGCTA GCAAAGAGGA GAAGGGTAAG CTCACTCTTC GCATTCCACA CCGTTAGTGT GTCAGTTTAG ACAAAAAAAC AACTACTATA CCAATTAGTA
5266       5276       5286       5296       5306       5316       5326       5336       5346       5356
GACTGTGAAC TGACTTTTGG AACGGCTTTT CGGACTGCGA TTATTCGTGA GGAATCAAGG GTCATATTTA CGGACAACAG TGGGTGATTC
5366       5376       5386       5396       5406       5416       5426       5436       5446       5456
CCATATGGAG TAGGAAAACG AGATCATGGT ATCCTCAGAT ATGTTGCGGA ATTCTGTTCA CCGCAAAGTT CAGGGTGCTC TGGTGGTTT CGGTTGGTCT
5466       5476       5486       5496       5506       5516       5526       5536       5546       5556
TTGCTTTGCT TCTCCCTTGT CTTGCATGTT AATAATAGCC TAGCCTGTGA GCCGAAACTT AGGGTAGGCT TAGTGTTGGA ACGTACATAT GTATCACGTT
5566       5576       5586       5596       5606       5616       5626       5636       5646       5656
GACTTGGTTT AACCAGGCGA CCTGGTAGCC AGCCATACCC ACACACGTTT TTTGTATTCT TCAGTATAGT TGTGAAAAGT GTAGCGGAAA TATGTGGTCC
5666       5676       5686       5696       5706       5716       5726       5736       5746       5756
GACTTGGGAGC GTCTTTTCT AGTAGTGCGG TCGGTTACTT GGTTGACATT GGTATTTGGA CTTTGTTGCT ACACCATTCA CTACTTGAAG TCGAGTGTGA
5766       5776       5786       5796       5806       5816       5826       5836       5846       5856
AGGGTATGAT TTCTAGTGGT GAACACCTTT AGTTACGTAA TGTTTTCATT GCTGTTTTAC TTGAGATTTC GATTGAGAAA AAGGTATTTA ATAGCTCGAA
```

```
      5866       5876       5886       5896       5906       5916       5926       5936       5946       5956
TCAATGTGTT ATCATTGTGA AGATGTTCTT CCCTAACTCG AAAGGTATAT GAGGCTTGTG TTTCTTAGGA GAATTATTAT TCTTTTGTTA TGTTGCGCTT
      5966       5976       5986       5996       6006       6016       6026       6036       6046       6056
GTAGTTGGAA AAGGTGAAGA GACAAAAGCT TAACACTTGA AATTTAGGAA AGAGCAGAAT TTGGCAAAAA AAATAAAACA CGTCGACTTG
      6066       6076       6086       6096       6106       6116       6126       6136       6146       6156
TGAGCGGGATA ACACTCGAGG GATCTTCATT ATGAAATTCT CTACTATATT AGCCGCATCT ACTGCTTTGT TTTCCGTTGT TATGGCTGCT CCAGTTTCTA
      6166       6176       6186       6196       6206       6216       6226       6236       6246       6256
CCGAAACTGA CATCGACGAT CTTCCAATTT CGGTTCCAGA AGAAGCCTTG ATTGGATTCA TTGACTTAAC CGGGGATGAA GTTTCCTTGT TGCCTGTTAA
      6266       6276       6286       6296       6306       6316       6326       6336       6346       6356
TAACGGAACC CACACTGGTA TTCTATTCTT AAACACCACC ATCGCTGAAG CTGCTTTCGC TGACAAGGAT GATTGAAGA AGCGCGCTCC CATGACCCAG
      6366       6376       6386       6396       6406       6416       6426       6436       6446       6456
ACAACGCCCT TGAAGACAAG CTGGGTTAAC TGCTCTAACA TGATCGATGA AATTATAACA CACTTAAAGC AGCCACCTTT GCCTTTGCTG GACTTCAACA
      6466       6476       6486       6496       6506       6516       6526       6536       6546       6556
ACCTCAATGG GGAAGACCAA GACATTCTGA TGGAAAATAA CCTTCGAAGG CCAAACCTGG AGGCATTCAA CAGGGCTGTC AAGAGTTTAC AGAACCCATC
      6566       6576       6586       6596       6606       6616       6626       6636       6646       6656
AGCAATTGAG AGCATTCTTA AAAATCTCCT GCCATGTCTG CCCCTGGCCA CGGCCGCACC CCAATCCATA TCAAGGACGG TGACTGGAAT
      6666       6676       6686       6696       6706       6716       6726       6736       6746       6756
GAATTCCGGA GGAAACTGAC GTTCTATCTG AAAACCCTTG AGAATGCGCA GGCTCAACAG ACGACTTTGA GCCTCGCGAT CTTTGAGTC CAACGTCCAG
      6766       6776       6786       6796       6806       6816       6826       6836       6846       6856
CTCGTTCTCT GGGCCTTCTC ACCACAGAGC CTCGGGACAT CAAAAACAGC AGAACTTCTG GTCATCTCTC ACACATTCCA GGACCAGAAG
      6866       6876       6886       6896       6906       6916       6926       6936       6946       6956
CATTTCACCT TTTCCTGCGG CATCAGATGA ATTGTTAATT ATCTAAATTC TGAAATGTGC AGCTCCCATT AAACCTCTGG CGGTTGTGTT CTCATTTTA
      6966       6976       6986       6996       7006       7016       7026       7036       7046       7056
TCCCATTGAG ACTATTATT TATGTATGTA CTGTATTTATT TATTTATTGC CTGGAGTGTG AACTGTATTT ATTTTAGCAG AGGAGCCATG TCCTGCTGCT
      7066       7076       7086       7096       7106       7116       7126       7136       7146       7156
TCTGCAAAAA ACTCAGAGTG GGGTGGGGAG CATGTTCATT TGTACCTCGA GAATTTATAC TTAGATAAGT ATGTACTTAC AGGTATATTT CTATGAGATA
      7166       7176       7186
CTGATGTATA CATGCATGAT AATATTTAAA GCTT
```

```
         10         20         30         40         50         60         70         80         90        100
TCGAATTTGC GGGGAGAAGA TGGATCTATG CTAAATCTAA ATAGGCATTT GAAAAACGAC GACGAGTTAC ACGACATATC GCCATCTTTA AATGAGCAAC
        110        120        130        140        150        160        170        180        190        200
CACACTGGGA CCTCATAGAG GACGGGTCTC GCTGGAGTAA ATTTTTCAAC GGGATAATTA AGACGACAAG AAGGTTCACG AAATCTTTAA TGAGGTCTTT
        210        220        230        240        250        260        270        280        290        300
AGTCAGAGGC AGGAACAGCC GTCAAGGGGG CATAAGACTA CGGTCATCCC CATCTGCCTC TTCGTCCAGC CTTGCCAACA GGGAGTTCTT CAGAGACATG
        310        320        330        340        350        360        370        380        390        400
GAGGCTCAAA ACGAAATTAT TGACAGCCTA GACATCAATA GTCATACAAC AGAAAGCGAC CACCCAACTT TGGCTGATAA TAGGCGTATAA ACAATGCATA
        410        420        430        440        450        460        470        480        490        500
CTTTGTACGT TCAAAATACA ATGCAGTAGA TATATTTATG CATATTACAT ATAATACATA TCACATAGGA AGCAACAGGC GCGTTGGACT TTTAATTTTC
        510        520        530        540        550        560        570        580        590        600
GAGGACCGCG AATCCTTACA TCACACCCAA TCCCCCACAA GTGATCCCCC ACACCACATA GCTTCAAAAT GTTCTACTC CTTTTTACT CTTCCAGATT
        610        620        630        640        650        660        670        680        690        700
GAGGACCGCG AATCCTTACA TCACACCCAA TCCCCCACAA GTGATCCCCC ACACCACATA GCTTCAAAAT GTTCTACTC CTTTTTACT CTTCCAGATT
        610        620        630        640        650        660        670        680        690        700
TTCTCGGACT CCGTACCACT CCGTACCACT TCAAAACACC CAAGCACAGC ATACTAAATT TCCCCTCTTT CTTCCTCTAG GGTGTGTTA ATTACCGTA
        710        720        730        740        750        760        770        780        790        800
CTAAAGGTTT GGAAAAGAAA AAAGAGACCG CCTCGGTTCT TTTTCTTCGT CGAAAAAGGC AATAAAAATT TTTATCACGT TTCTTTTTCT TGAAAATTTT
        810        820        830        840        850        860        870        880        890        900
TTTTTTTGAT TTTTTTCTCT TTCGATGACC TCCCATTGAT ATTTAAGTTA ATAAACGGTC TTCAATTTCT CAAGTTTCAG TTTCATTTTT CTTGTTCTAT
        910        920        930        940        950        960        970        980        990       1000
TACAACTTTT TTTACTTCTT GCTCATTAGA AAGAAAGCAT AGCAATCTAG TCGACAGATC TCTCGAGTGC TTTTGTGCGC GTATGTTTAT GTATGTACCT
       1010       1020       1030       1040       1050       1060       1070       1080       1090       1100
CTCTCTCTAT TTCTATTTTT AAACCACCCT CTCAATAAAA TAAAAATAAT AAAGTATTTT TAAGGAAAAG ACGTGTTTAA GCACTGACTT TATCTACTTT
       1110
TTGTACGTCT AGA
```

FIG. 24

EXPRESSION AND PURIFICATION OF HUMAN INTERLEUKIN-3 AND MUTEINS THEREOF

CROSS-REFERENCE TO RELATED APPLICATION

This application is a continuation-in-part of U.S. patent application Ser. No. 07/249,184, filed 16 Aug. 1988; now abandoned and PCT Application No. NL87/00037, filed 16 Dec. 1987.

FIELD OF THE INVENTION

The present invention relates to cDNA encoding human interleukin-3 (IL-3) and its use, inter alia, in cloning and expression in various organisms, including microorganisms, in particular yeasts, bacteria and fungi, tissue culture cells and transgenic animals and plants. The instant invention also relates to improved methods for the production and purification of hIL-3 and muteins thereof.

BACKGROUND OF THE INVENTION

Hemopoiesis involves the active process of proliferation and differentiation of pluripotent progenitor cells into all types of mature blood cells and some specialized tissue cells. Production of functional blood cells is regulated by specific proteins, the hemopoietic growth factors (HGFs). Some of the HGFs control maturation of a specific maturation lineage, whereas others stimulate proliferation and differentiation of progenitors along multiple pathways. Much of our knowledge of the hemopoietic differentiation process has been obtained from mouse studies in vitro and in vivo, using purified growth factors. The murine growth factor interleukin-3 (mIL-3), also termed multi-CSF, mast cell growth factor, stem cell activating factor or several other designations, stimulates the proliferation of developmentally early, multipotent cells (CFU-S) as detected by the spleen colony assay, resulting in the production of progenitor cells along the erythroid, megakaryocyte, granulocyte/macrophage, osteoblast and several other lineages. Furthermore, mIL-3 has been implicated in replication of pluripotent stem cells, probably in synergism with other HGFs.

In recent years, several groups have succeeded in cloning mIL-3 cDNA. No results have been reported so far of identifying homologous sequences in human DNA using mIL-3 DNA as a probe. Presumably, the human gene has diverged extensively from the mIL-3 gene or has lost its function during primate evolution. However, human leukocytes were found to produce an HGF(s) which can replace M-GSF in supporting the proliferation of murine CFU-S. Thus, the existence of a human HGF was postulated, which shares biological properties with mIL-3 and therefore could be the human homolog.

Recently, DNA sequences encoding hIL-3 have been identified by several investigators. For instance, using as probe a cDNA coding for gibbon IL-3, the human IL-3 gene was isolated (Yang et al., 1986). The sequence of the exons of the human gene was disclosed in the cited paper as well as in patent application WO 88/00598 (published 28 Jan. 1988). However, as known to those skilled in the art, the intron-containing genomic sequence cannot be used for synthesis of hIL-3 in microorganisms. Rather, the coding sequence used should be a continuous coding sequence as in a cDNA. A cDNA sequence encoding human IL-3 is also disclosed in WO 88/00598. Following another route, Dorssers et al. (1987) also isolated a cDNA coding for human IL-3.

Patent Application No. WO 88/05469 discloses the isolation of a cDNA encoding hIL-3 using a synthetic DNA derived from the genomic sequence described by Yang et al. (1986) as a probe. The disclosed cDNA sequence, however, lacks two amino acids, nos. 44 and 45 or 45 and 46. The amino acid bordering either deletion is a GAC encoded Asp. Nonetheless, the culture supernatant of a yeast transformant carrying this cDNA sequence in an expression cassette, encoding mature hIL-3 fused to an N-terminal "flag" of 8 amino acids, shows IL-3 activity in a human bone marrow proliferation assay. This finding indicates that the absence of the aforementioned two amino acids and the N-terminal extension of 8 amino acids has no deleterious effect on the biological activity of the protein.

Finally, EP 282.185 also discloses the isolation of a hIL-3 cDNA sequence using as probe a synthetic DNA derived from the genomic sequence described by Yang et al. (1986) and describes the construction of a completely synthetic hIL-3 coding sequence as well as the construction of two muteins, Ile$^2$ and Leu$^{131}$. There is no mention of biological activity. Furthermore, it was apparently assumed that hIL-3 contains 132 amino acids, starting at the N-terminus with Pro$^1$-Met$^2$-, whereas it is generally accepted that hIL-3 is 133 amino acids long and has as the N-terminus Ala$^1$-Pro$^2$-Met$^3$.

It is noteworthy that Yang et al. (1986) find a Ser residue at position 8 of the mature hIL-3, whereas all other references indicate the presence of a Pro at this position.

BPV-1 or the 69% subgenomic fragment (BamHI-HindIII) has been used for the expression cloning of a variety of genes in different cloning systems. EP-A-198386 describes the expression of gamma-interferon in C127 mouse cells. In EP-A-105141 the use of the BPV vector is described for the expression of hepatitis B surface antigen (HBsAg) in vertebrate cell lines e.g. NIH 3T3, LTK− mouse fibroblasts and African green monkey kidney cells. The general idea of using BPV-1 is disclosed in U.S. Pat. No. 4,419,446.

BPV-1 is one of at least six bovine papillomaviruses and is associated with cutaneous fibropapillomas in cattle. These viruses can readily transform a variety of rodent cells in culture. The molecularly cloned bovine papillomavirus DNA as well as a cloned 69% subgenomic fragment are efficient in inducing transformed foci. Transformed cells contain multiple copies (10 to 120 per cell) of the viral DNA as unintegrated molecules (Law et al., 1981). The genetics of bovine papillomavirus type I have been extensively studied (for a review see Lambert et al., 1981). The BPV-1 genome is a circular, 7946 base-pair, double-stranded DNA molecule. The transcription is complicated because of the presence of multiple promoters, splice sites, and differential production of RNA species. The activities of some of the promoters are under tight control of transcriptional enhancers.

The so-called E2 (=early) ORF is very important in this respect. The full-length E2 ORF encodes a transactivating protein (E2-ta) which can stimulate transcription of the early genes.

This protein consists of two conserved domains, the amino terminal domain (which has transactivating activity) and the carboxy-terminal domain (which has both DNA-binding and dimer formation activities). The E2 ORF encodes a second regulatory protein, the E2 transcriptional repressor (E2-tr), which is an amino-terminally truncated form of the E2-ta protein. E2-tr is encoded by another mRNA, whereby the translation initiation codon is an E2 ORF internal ATG-codon.

The present invention discloses cell lines not previously employed in hIL-3 production as well as mutations of the E2 ORF.

The clinical utility of hIL-3 is not only dependent on its inherent characteristics but also on its availability and the lack of contaminants. The prior art relating to the purification of murine, gibbon and human IL-3 is briefly reviewed here.

The mature murine T-cell enzyme marker 20a-hydroxy-steroid dehydrogenase (20aSDH) was found to be inducible in vitro. The factor responsible for this was partially purified from splenic lymphocytes by Ihle et al. (1981). It was distinct from other known lymphokines in both its biochemical and functional properties. Ihle et al. (1981) proposed the term interleukin-3 ("IL-3") for this factor. The purification by Sephadex G-100 and DEAE cellulose chromatography resulted in a 9000-fold purification, yet the final preparation still contained multiple proteins.

An improved purification procedure was presented by Ihle et al. (1982), wherein WEHI-3 cells which constitutively produce IL-3, were used. Here, through the extension of the earlier procedure with hydroxylappatite and reverse-phase high performance liquid chromatography, the final product could be obtained 1,800,000-fold purified (their Table I). This product was claimed to be homogeneous.

Miyajimi et al. (1987) used the silkworm *Bombyx mori* and an insect baculovirus vector for high-level expression and secretion of murine IL-3. Purification of IL-3 from tissue culture medium was carried out by sequential passage through DEAE-Sephadex, ACA 54 and C8 reverse-phase column chromatography. To obtain separation of three species of IL-3 (18, 20 and 22 kDa) a second C8 reverse-phase column was necessary. The different species are due to differential glycosylation, since N-glycanase treatment yielded one final band of 15 kDa.

Ziltener et al. (1988) described the isolation of multiple glycosylated forms of IL-3 by affinity purification. The observed microheterogeneity was dependent on the source (activated T-cells, WEHI-3B cells or COS 7 cells).

All of the above procedures describe the purification of murine IL-3. In spite of the observed similarity of murine and human IL-3 with respect to their proliferative action on haematopoietic progenitor cells, the structural homology between both proteins is rather low (28% at amino acid level). This heterogeneity is illustrated by the total absence of reactivity of the human protein on murine cells (and vice versa). Based on their specific amino acid composition, the proteins likely require different methods of purification.

The purification of both gibbon and human IL-3, which show a structural homology of 93% (at the amino acid level), is disclosed in several patent publications. WO 88/00598 describes the isolation of a partially synthetic hIL-3 from the inclusion bodies of *E. coli* cells. The cells are first disrupted by two passages through a french press, and the inclusion bodies are isolated by centrifugation in a sucrose step gradient. This reference describes also three procedures for purifying a human or gibbon IL-3-like polypeptide from COS cell conditioned medium. In all cases a one-column process is used: either ion exchange or a lentil lectin column or reversed-phase HPLC. The maximum purity obtained for gibbon IL-3 as determined with automated Edman degradation was 98%.

WO 88/05469 describes the purification of human IL-3 from yeast strains by single or sequential reversed-phase HPLC steps. Since additional HPLC steps can be employed if indicated, it is clearly not assumed that the product is homogeneous. No test of the purity of the hIL-3 was described, nor were data mentioned on the purity of the product.

Thus, no specific methods have been disclosed so far for the purification of hIL-3. Therefore there is still a need for substantially pure hIL-3 which can be used therapeutically and for a method of preparing such substantially pure product in a high yield, and which can easily be scaled up.

SUMMARY OF THE INVENTION

The present invention describes the isolation of a cDNA comprising the entire coding sequence for human IL-3. The low degree of homology between the DNA sequences coding for murine and human IL-3 does not permit the retrieval of a cDNA for hIL-3 by hybridization with the mIL-3 coding sequence. Unexpectedly, the hIL-3 cDNA clone could be isolated by exploiting the rather high degree of homology in the 3' noncoding part of the cDNAs. The availability of the cDNA clone permits the production of hIL-3 in a wide range of host organisms. Subsequent to large-scale production, the protein may be purified and used therapeutically.

The present invention permits production of recombinant human IL-3 protein in a wide range of host cells by transcription and translation from a cDNA sequence encoding the human IL-3 protein. The production of the protein is illustrated hereinbelow in several hosts, including *E. coli*, COS cells, CHO cells, C127 cells, FR3T3 cells, *B. subtilis*, *B. licheniformis*, *S. cerevisiae* and *K. lactis*. Production in other hosts using appropriate expression systems is also made possible by provision of the intronless cDNA. More generally, the availability of antihuman IL-3 antibodies which permit identification of colonies exhibiting successful production of the recombinant protein aids in production of human IL-3 from any recombinant system.

In one aspect, therefore, the invention is directed to a recombinant, intronless, DNA encoding human IL-3 protein.

In another aspect, it is directed to expression systems capable of effecting the expression of said DNA sequence encoding hIL-3 in an appropriate host.

In other aspects, the invention is directed to recombinant human IL-3 protein in glycosylated or unglycosylated form, to purified human IL-3 free of substances normally accompanying said protein, and to antibodies specifically reactive with these recombinant or purified proteins.

The invention also provides a method for purifying human IL-3 to homogeneity by an initial stage of hydrophobic interaction, followed by ion exchange chromatography and gel filtration. This method is particularly useful for hIL-3 obtained by recombinant prokaryotic and eukaryotic expression systems. These and other aspects of the present invention will be further discussed below.

BRIEF DESCRIPTION OF THE DRAWINGS

FIGS. 1A–1B shows a comparison of DNA and protein sequences of human multi-CSF and mouse IL-3. The hmulti-CSF protein and DNA sequence (clone D11, top lines) were aligned with the mIL-3 DNA (Fung et al., 1984; Miyatake et al., 1985) and protein sequence (Clark-Lewis et al., 1986). Identical nucleotides are indicated by a vertical line, identical amino acids are shown in boxes. Black dots indicate a polyadenylation signal sequence and horizontal bars mark ATTTA repeat units.

FIG. 6 shows the sequence of the multicloning site in pTZ18R (Pharmacia) and its derivative pT1.

FIGS. 8A–8B shows the sequences of fusion regions of lacZ/hmulti-CSF DNA for various bacterial expression vectors. The sequence of clones is given from the start of the lacZ protein in either pUC8 or pTZ18R (lower case letters) and of hmulti-CSF DNA sequence up to the ClaI site at position 158. Mutations in the hmulti-CSF DNA sequence are underlined, resulting in: trp$^{13}$→arg$^{13}$ (pGB/IL-302); leu$^9$→pro$^9$ and trp$^{13}$→arg$^{13}$ (pGB/IL-303); met$^3$→thr$^3$ and a silent change (pGB/IL-304). The superscripts denote the amino acid residue number of the mature protein.

FIGS. 17A–17F shows the nucleotide sequence of plasmid pBHA1.

FIGS. 22A–22B shows the nucleotide sequence of plasmid pGB/IL-316 between the unique SacII site in the lactase promoter and the HindIII site behind the terminator (residues 4457 to 7204).

FIGS. 23A–23B shows the nucleotide sequence of plasmid pGB/IL-318 between the unique SacII site in the lactase promoter and the HindIII site behind the terminator (residues 4457 to 7190).

FIG. 24 shows the nucleotide sequence of the EF-1alpha promoter, SalI-BglII-XhoI linker, and actin terminator as present on plasmid pGB/TEFact.

DETAILED DESCRIPTION OF THE INVENTION

A. Definitions

Figure 2:
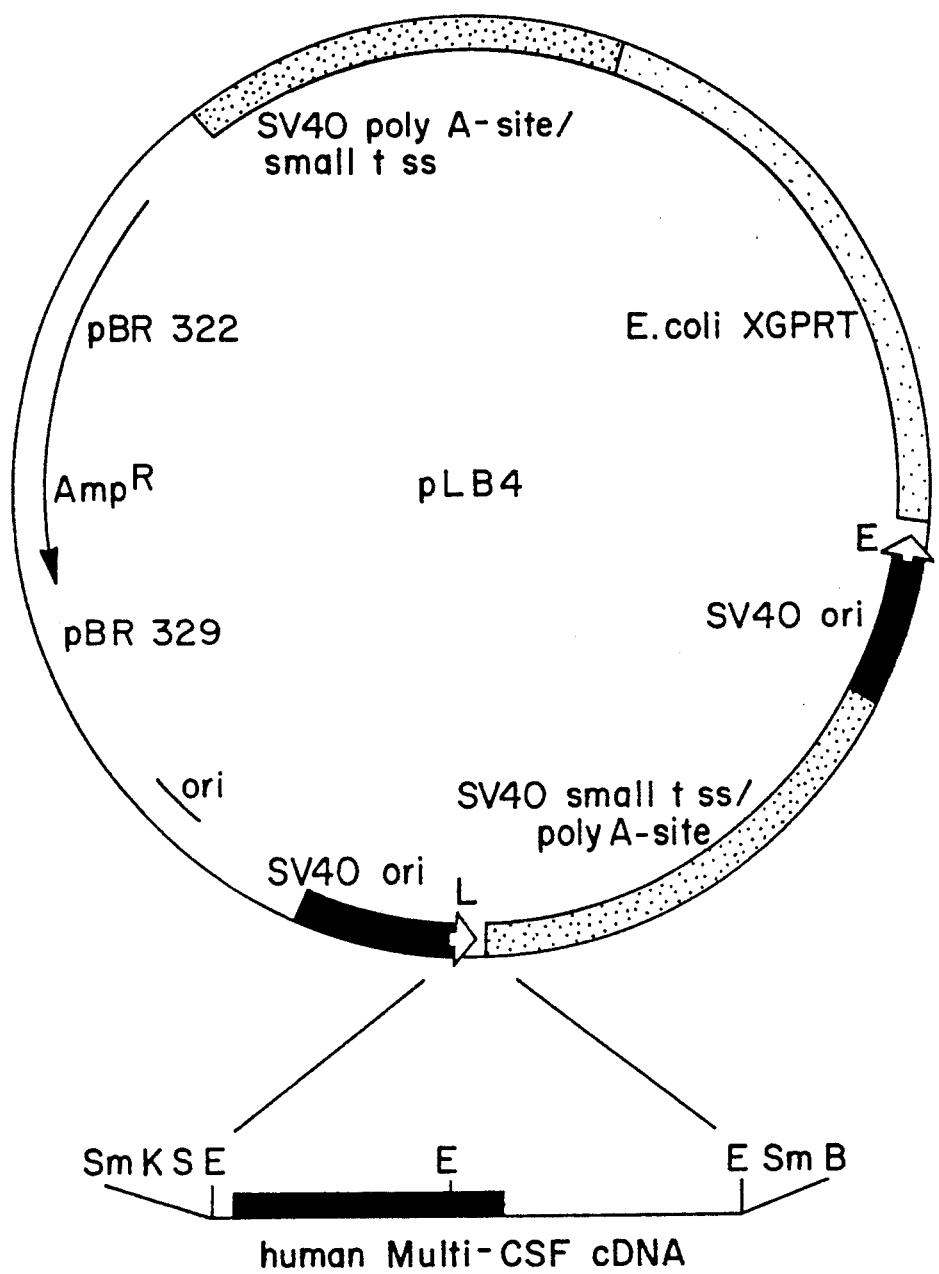
FIG. 2 shows the construction of plasmid pLB4 containing human IL-3 cDNA. E=EcoRI, Sm=SmaI, B=BamHI, S=SstI, K=KpnI.

As used herein, "human IL-3", "hIL-3", "human multi-CSF", and "hmulti-CSF" are used interchangeably, and designate a protein preparation which exhibits the following activities:

1. The protein stimulates colony formation by human hemopoietic progenitor cells wherein the colonies formed include erythroids, granulocytes, granulocyte macrophages, megakaryocytes and mixtures thereof.

2. The protein stimulates DNA synthesis by human acute myelogenous leukemia (AML) blasts, as evidenced, for example, by labeled thymidine uptake.

To fit the definition of hmulti-CSF, the activity in the foregoing assay must not be substantially inhibited by antibodies raised in response to, and immunospecific for, GM-CSF, unless these antibodies also inhibit these activities by the illustrative hmulti-CSF below.

By a protein "equivalent to hIL-3" is meant a protein displaying the above biological activity.

Figure 1A:
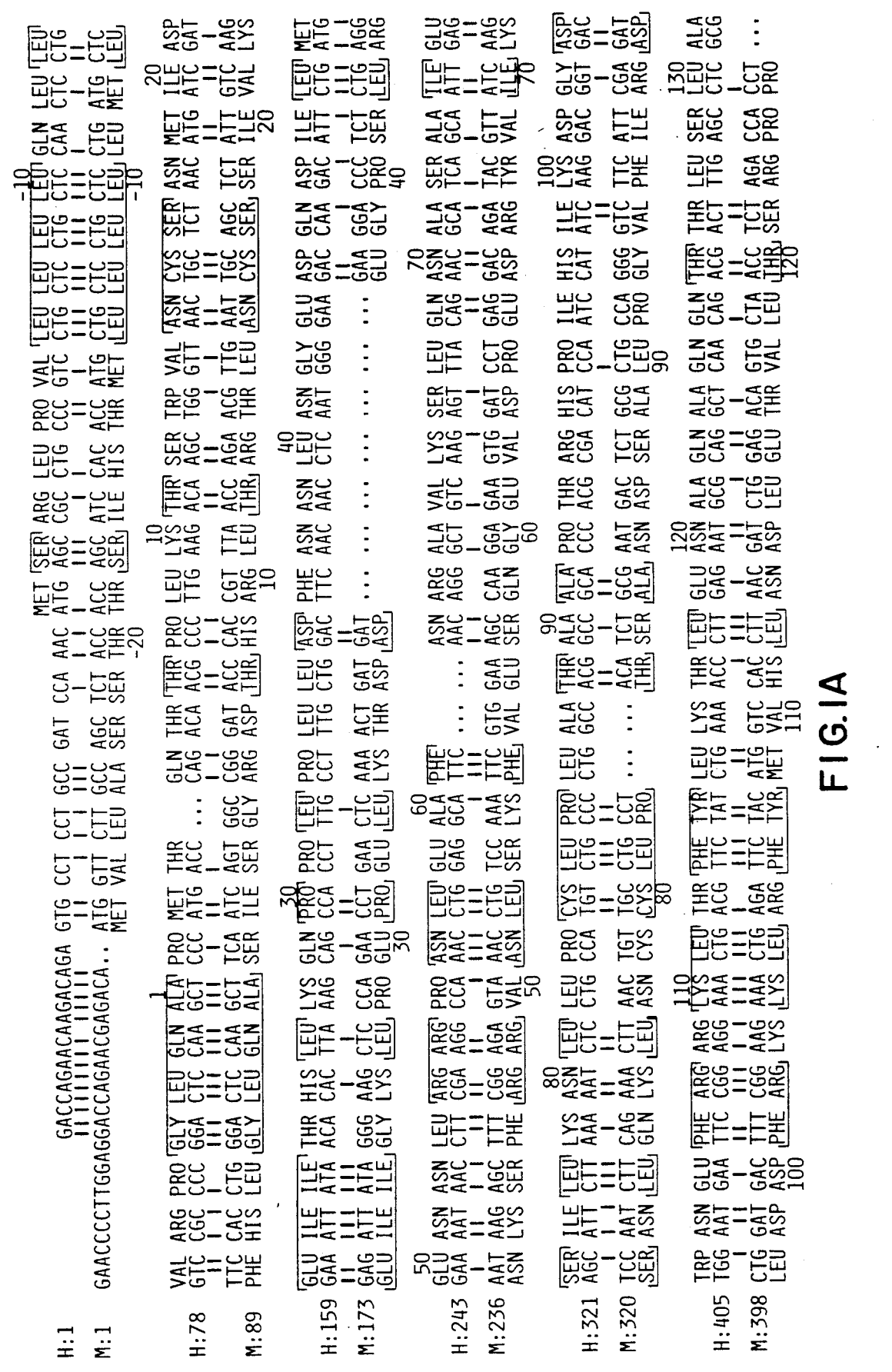
Figure 1B:
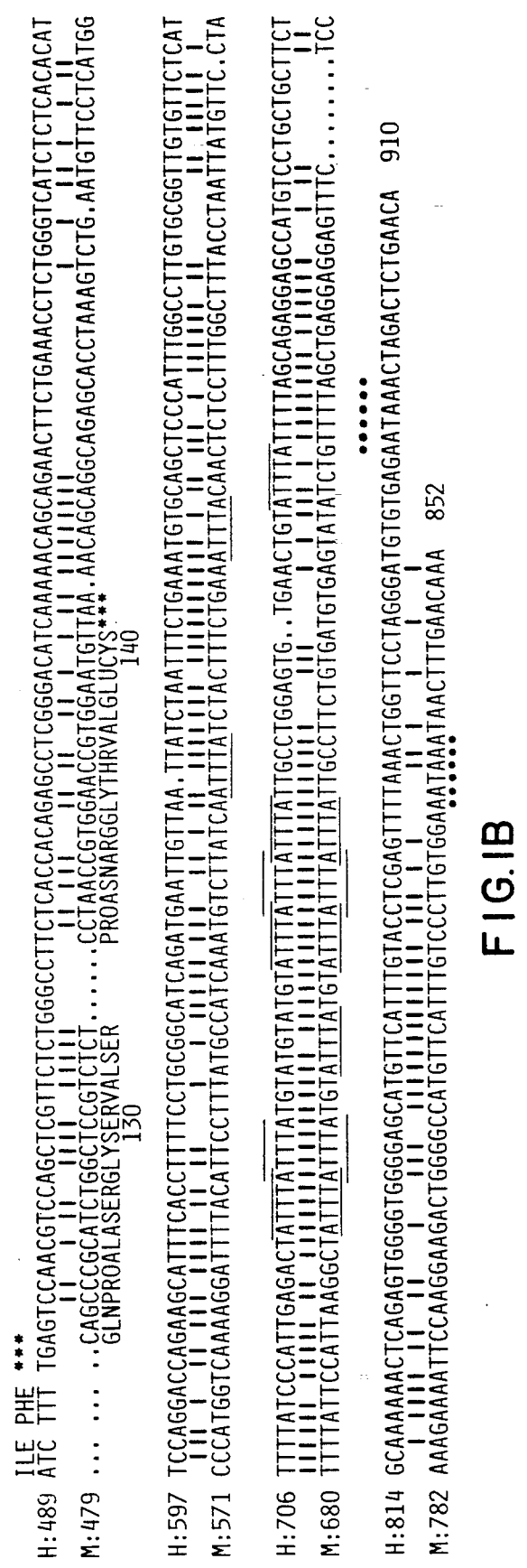

One illustrative form of hmulti-CSF is shown in FIG. 1 as a 133 amino acid mature protein, having a 19 amino acid signal sequence. The amino acid sequence of FIG. 1 is identical with that disclosed by Yang et al. (1986) except at position 8 of the mature protein wherein the Ser of the Yang protein is replaced by Pro herein. As shown herein, this amino acid sequence is effective in its nonglycosylated form. However, it contains two glycosylation sites, and the glycosylated form is also included within the scope of the invention. It is also recognized that the protein may exist in acid addition salt form, basic salt form, or may be neutral, depending upon the pH of its surroundings. Derivatization by phosphorylation, acetylation, and so forth to the extent that activity is not destroyed, also results in a protein included within the scope of the invention.

It is also recognized that the entire sequence may not be necessary for activity. Parts of the amino acid sequence may be deleted or replaced, while retaining biological activity. As illustrated herein, the alanine at position 1 may be deleted, as may as many as the first fourteen amino acid residues if replaced by a sequence of residues of a fused peptide sequence. In addition, it is believed that the murine form of the protein requires only the first 79 residues for activity; this corresponds approximately to the first 83 residues of the human counterpart. Accordingly, fragments which comprise only the first 83 amino acid residues of the protein, and the N-terminal replaced forms thereof, are also included within the scope of the invention. Furthermore, it should be considered that the N-terminus of mature hIL-3 is formed by the residues ala-pro-met etc. (see FIG. 1). It is known that the protein, when secreted by a yeast host, may in some instances be shortened by two amino acids (ala-pro), due to the interaction with a dipeptidylaminopeptidase (Suarez Rendueles, 1981). The hIL-3 without the N-terminal alanine and proline still retains its biological activity. Yeast strains carrying a null mutation of the X-prolyl dipeptidylaminopeptidase gene will produce complete hIL-3 (amino acids 1–133). Accordingly, included in the multi-CSFs of the invention are those which contain and those which do not contain the N-terminal alanine and proline, produced by X-prolyl dipeptidylaminopeptidase mutants and wild-type hosts, respectively.

When produced as a mature protein in a prokaryotic host, the coding sequence for the mature protein will be prefaced by an ATG start codon. The resulting N-terminal methionine may then be removed, or partially removed, by processing within the bacterial host, depending on the nature of the subsequent amino acid sequence. Again, both forms of the hIL-3 are biologically active. Therefore, included in the hmulti-CSFs of the invention are those which contain and those which do not contain the N-terminal methionine.

From the above it is clear that amino acid changes may be introduced into the human IL-3 protein without affecting its biological function. It is recognized that minor changes in amino acid sequences by chemical modification of the encoded residue, substitution of a different residue, or deletion or addition of one or more, but preferably only one, residue results in proteins which retain activity. Accordingly, these nondestructive mutations are also included within the invention, in particular, the naturally occurring allelic variations and other mutations which are nonlethal to the activity.

On the other hand, it should be considered that amino acid changes in the human IL-3 protein may be beneficial to the therapeutic use of the protein. As recognized herein, the mature protein has four conserved domains at residues 15–36, 54–61, 74–91, and 107–118. Proteins containing single and multiple amino acid changes in the nonconserved regions, 1–14 (which are, in any event, replaceable by the sequences of host-derived fusion proteins), 37–53, 62–73, 92–106, and 119–133, are possible. However, it appears that the cysteine residues at positions 16 and 84 may be necessary for disulfide bridge formation as they are conserved between species. Changes in the conserved domains mentioned above may influence biological properties of the protein, such as receptor binding and signal transduction. It is envisaged that hIL-3 having altered properties are of therapeutic use. Such derivatives of hIL-3, which may be made by known protein engineering techniques, are to be understood to be within the scope of the present invention.

hIL-3-like proteins, with altered amino acid sequences, may have altered effects on target cells. Such molecules may function either as agonists or as antagonists and have potential clinical applications. These altered molecules are included in the present invention, and several of these hIL-3-like proteins are biologically active. These active proteins may serve as agonists and may show properties beneficial in clinical use, such as enhanced stability, better binding to the IL-3 receptor, etc. Proteins which have lost their biological functions may still serve as antagonists, e.g., when binding of such a protein to the IL-3 receptor does not result in signal transduction. These proteins are also contemplated by the present invention.

The protein preparation may contain the hmulti-CSF peptides in monomeric or aggregated form, provided the aggregates retain activity as defined above.

As used herein, "expression system" refers to a DNA sequence which contains both a coding sequence whose expression is desired and appropriate control sequences in operable linkage with it which permits its expression when the control sequences are compatible with the host into which the expression system is placed. As is generally understood, "control sequences" refers to DNA segments which are required for or regulate the expression of the coding sequence with which they are operably linked.

Control sequences for all hosts include promoters, which may or may not be controllable by regulation of their environment. Typical promoters suitable for prokaryotes include, for example, the trp promoter (inducible by tryptophan deprivation), the lac promoter (inducible with the galactose analog IPTG), the beta-lactamase promoter, and the phage-derived $P_L$ promoter (inducible by temperature variation). Additionally, especially for expression in Bacillus, useful promoters include those for alpha-amylase, protease, Spo2 and synthetic promoter sequences. Suitable promoters for expression in yeast include the 3-phosphoglycerate kinase promoter and those for other glycolytic enzymes, as well as promoter regions for alcohol dehydrogenase, and yeast phosphatase. Also useful are the transcription elongation factor (TEF) and lactase promoters. Mammalian expression generally employs promoters derived from viruses such as the adenovirus promoters and the SV40 promoter systems, but they also include regulable promoters such as the metallothionein promoter, which is controlled by heavy metals or glucocorticoid concentration. There are also now available virus-based insect cell expression systems, as well as expression systems based on plant cell promoters such as the nopaline synthetase promoters.

In addition to the promoter DNA sequence, which is necessary for the transcription of the gene by RNA polymerase, a variety of control sequences, including those regulating termination (for example, resulting in polyadenylation in eukaryotic systems) are also useful in controlling expression. Some systems also contain enhancer elements which are desirable but not necessary in effecting expression.

Translation controls include a ribosome binding site (RBS) in prokaryotic systems, whereas in eukaryotic systems translation may be controlled by the nucleotide sequence around the AUG codon.

As implied above, recombinant protein production can be effected in a wide variety of hosts, including bacteria (predominantly *E. coli*, Bacillus, and Streptomyces), in yeast and fungi (such as Saccharomyces, Kluyveromyces, and Aspergillus), and in mammalian and other cell cultures such as COS cells, C127 cells, FR3T3 cells, Chinese hamster ovary cells, *Spodoptera frugiperda* (Sf9) cells, and so forth. The protein may be produced as an intracellular mature or fusion protein, or may be secreted when the DNA encoding an appropriate compatible signal is included in the gene.

It has been surprisingly found that the combination of a perfect fusion of host signal sequences to mature hIL-3 coding sequences, in conjunction with strong promoters in Bacillus, as well as the use of strong promoter/enhancer combinations and mRNA stabilizing sequences on BPV-1 derived vectors in C127, FR3T3 and CHO cells, leads to improved productivity of hIL-3.

All elements used for expression of hIL-3 in Bacillus species have been described in WO 88/04691. Surprisingly, however, optimal combinations of promoters, signal sequences and mature hIL-3 coding sequences were found by rearrangement of the different genetic elements. For proper secretion of hIL-3 by Bacillus species a perfect junction between a-amylase signal sequence and hIL-3 coding sequence was found to be crucial. Already using the sigma-43 promoter (see WO 88/04691) hIL-3 could be found in the culture medium, but only after inclusion of the strong a-amylase or HpaII promoter in the expression plasmid high level expression was obtained.

WO 88/04691 also describes expression of active hIL-3 by C127 cells. However, expression levels are relatively low when using the pLB4/BPV vector. It has now been surprisingly found that the use of the combination of The Moloney Murine Sarcoma Virus (MSV) enhancer and mouse metallothionein I promoter (MT promoter), or the Human Cytomegalovirus enhancer/promoter, instead of the SV40 enhancer/promoter as present in pLB4/BPV, results in improved expression levels of hIL-3 by mammalian cells. Specifically, when an expression vector containing the MSV enhancer/MT promoter is used to establish stable cell lines from C127 cells, a more than 20-fold increase in IL-3 expression can be obtained. These latter cell lines allow efficient production of hIL-3 with mammalian (complex) type glycosylation.

Furthermore, production of hIL-3 using stable CHO cell lines, described herein, unexpectedly equalled the best known production system. These CHO cells are also readily adapted to growth in suspension and can be mass-cultured in large reactors.

Additionally, replacement of the hIL-3 cDNA sequence by the genomic hIL-3 sequence has a beneficial effect on the steady state level of hIL-3 mRNA.

A further increase in mRNA level can be achieved by mutating the start codon used for the translation of E2-tr. From the description of BPV-1, it is already clear that E2-ta and E2-tr have an antagonistic activity. By mutating the aforementioned start codon, the production of E2-tr (the repressor protein) is clearly abolished. Without this repressor activity, the transcription of the early genes is considerably increased leading to an increase in plasmid copy number. This results in an increase of the expression of the cloned gene and thus in a higher protein yield.

The present invention, thus for the first time, enables large-scale production of recombinant human IL-3, so that this protein—in purified form—can now be used as a therapeutic agent. The methods described herein provide means for producing glycosylated as well as unglycosylated forms of the protein, which can be purified to substantially pure human IL-3. "Purified" human IL-3 refers to human IL-3 as defined above which is substantially free of other proteins which normally accompany it. That is, hIL-3 is substantially free of other proteins when at least about 75% by weight of the total hIL-3 plus other proteins is hIL-3. Preferably, hIL-3 comprises at least 90% by weight of the protein in the composition. By "crude" protein product is meant a protein product that is not comprised of substantially pure hIL-3.

Human IL-3 can be purified to homogeneity using a combination of hydrophobic interaction, ion exchange chromatography and gel filtration. Although many purification techniques have been known for quite some time, this specific combination surprisingly proved to be extremely powerful for obtaining substantially pure hIL-3. Moreover, this purification method results in a pyrogen-free product. It is very suitable for upscaling after fermentation where hIL-3 contained in the fermentation broth after secretion from the cells must be purified from contaminating components of the growth medium. The method is particularly useful for the purification of hIL-3 produced by transformed hosts, both prokaryotic and eukaryotic.

The initial stage of the purification is preferably carried out by hydrophobic interaction. This step is unusual but very effective for the purpose of this invention. Presumably, it causes a selective separation on the basis of the structure of the protein itself. The next step is preferably ion exchange chromatography, in which hIL-3 is found in the run-through fractions separated from most of the contaminating proteins. Subsequently, gel filtration is applied which will separate low molecular proteins.

If hIL-3 degradation products are present in the starting material to be purified, for example from *Bacillus licheniformis*, these proteins can be advantageously separated from native hIL-3 by means of anion exchange chromatography, preferably on Q Sepharose Fast- Flow. Chromatography on hydroxylapetite and chromatofocussing on pBE94 are efficient techniques for the separation of hIL-3 degradation products.

The hydrophobic interaction is advantageously performed using a TSK-butyl or octyl Sepharose column, of which hIL-3 can be eluted for example with gradients of either $(NH_4)_2SO_4$ in Tris-HCl or ethylene glycol. The removal of contaminating proteins (and other substances) by ion-exchange chromatography may require the use of columns such as, for example, TSK-DEAE, Q Sepharose Fast-Flow or TSK-CM.

Finally, gel filtration using, preferably, Biogel A or Sephacryl S100 HR is an excellent final step in the purification of unglycosylated hIL-3.

The starting point for the purification can be either intracellular hIL-3 or hIL-3 contained in a fermentation broth. The isolation of intracellular hIL-3 is made much easier when the protein is contained in so-called inclusion bodies. The first step would then be the isolation of these bodies which contain the product in a relatively pure form at a high concentration. After solubilization, hIL-3 can be further purified by chromatography.

B. Retrieval of cDNA Encoding Human IL-3

Human IL-3 cDNA was isolated according to the following strategy:

1. A procedure was developed which allowed for reproducible production of hemopoietic growth factors (HGFs) by human leukocytes.
2. mRNA was prepared from such producing cells and transcribed into double-stranded cDNA.
3. The cDNA was screened with a complete mIL-3 cDNA which contained both the coding and untranslated 3′ downstream portions to obtain DII.
4. The hybridizing cDNA clone D11 was inserted into an expression vector pLO to obtain pLB4 which was expressed in COS cells to confirm the presence of the sequence encoding human IL-3. Conditioned media from these cells showed the biological activity expected of hIL-3.

The human cDNA was retrievable using this procedure because despite considerable lack of homology with the murine coding sequence, a surprising degree of homology was present in the 3, untranslated region. Applicants are unaware of any prior disclosure of the use of a 3′ untranslated sequence homology to retrieve an alternate species gene.

In more detail, conditioned medium of lymphocytes cultured in the presence of 12-O-tetradecanoylphorbol-13 acetate (TPA) and concanavalin A (ConA) is a suitable source for human HGFs as determined by assay of the medium using stimulation of mouse CFU-S in suspension cultures, proliferation of mIL-3 dependent DA-1 cells, human hemopoietic progenitor assays by colony formation in vitro, and in vitro stimulation of acute leukemia blasts. A cDNA library from human lymphocytes was constructed in lambda gt10 phage (Huynh et al., 1985) and screened using the HindIII-XbaI fragment of mIL-3 cDNA, for the occurrence of mIL-3 related sequences. No hybridizing clones were identified.

However, when complete murine IL-3 cDNA was used as probe, four clones were identified. Restriction enzyme analysis of the largest clone (D11) indicated a 910 bp insert containing an internal EcoRI site (at position 411, FIG. 1).

(It was investigated whether this EcoRI site had arisen by ligation of two independent cDNA fragments or was a naturally occurring site. Southern analysis of restriction enzyme digested human DNA using labeled 5′ and 3′ EcoRI fragments of clone D11 as probe, revealed identical DNA fragments following digestion with HindIII (15 kb) and BamHI (4.6 kb). Furthermore, the DNA sequence around the EcoRI site does not correspond to linker sequence (pCCGAATTCGG) used for inserting cDNA into phage DNA, indicating that these EcoRI fragments are derived from a single mRNA.)

From hybridization and sequencing experiments it was concluded that the small clones (II, IV and VI) are identical to the 3′ nucleotide sequence of clone D11 and derived from the same mRNA species.

Computer assisted alignment (FIG. 1) of the D11 cDNA and the mIL-3 cDNA revealed sequence homology in the 5′ terminal 100 bp, between nucleotides 236–269 and between nucleotides 598–803 in the 3′ terminal region (68%, 71% and 73% homology, respectively). In particular, the region between the nucleotides 706 and 763 is highly conserved (93% homology) and contains repetitive AT-rich sequences. The low homology in the 5′ terminal 600 bp of the human cDNA (52%) precludes detection by hybridization with the HindIII-XbaI fragment of mIL-3.

Analysis of the human cDNA clone for an encoded protein shows an open reading frame up to the termination codon TGA at position 495–497 (FIG. 1). The first ATG triplet is probably the actual initiation codon of the encoded polypeptide. The putative encoded protein consists of a hydrophobic leader peptide of 19 amino acids, which is probably cleaved between the glycine and alanine residues (Von Heijne, 1983; Perlman and Halvorson, 1983).

The alignment of the predicted amino acid residues of the human and mouse IL-3 (FIG. 1) reveals a homology of 50% for the leader peptide (residues −19 to +1) and 28% for the mature protein (residues 1 to 133). Within the leader peptide, there are two conserved regions of four amino acids (residues −13 to −10 and −3 to +1), of which the second one encloses the processing site. The mature protein is 133 amino acids long and has a molecular weight of 15 kd. The mature protein has four conserved domains (residues 15–36, 54–61, 74–91 and 107–118) and contains two potential glycosylation sites (residues 15–17 and 70–72). Both cysteine residues present in the human protein (positions 16 and 84) are conserved and may play an essential role in protein folding by disulfide bridge formation.

In order to verify that this human cDNA encodes a functional protein that resembles mIL-3, the D11 cDNA was inserted in a eukaryotic expression vector (pLO containing an SV40 transcription unit) to obtain the expression vector pLB4 and transfected to COS 1 cells. The COS/pLB4 conditioned medium (CM) was tested for (1) its capacity to stimulate colony formation by human bone marrow cells, and (2) to stimulate human acute myelogenous leukemia (AML) blasts.

In vitro colony growth of human hemopoietic progenitors depleted of myelomonocytic (Vim-2 positive) and T-lymphocytic (T-3 positive) accessory cells, was efficiently stimulated by COS/pLB4 CM. The data demonstrate stimulation of progenitors of several hemopoietic differentiation lineages and of a subpopulation of BFU-E by COS/pLB4 CM.

In a separate experiment, bone marrow was enriched for progenitor cells by density centrifugation, E-rosette sedimentation to remove T-lymphocytes and adherence to remove mononuclear phagocytes and culture in enriched medium containing fetal calf serum. Under these conditions, the majority of the colonies obtained upon stimulation with COS/pLB4 CM contained two or more hemopoietic differentiation lineages: all contained macrophages, approximately half immature blasts and/or immature erythroid cells and/or neutrophilic granulocytes and a minority, in addition, basophilic or eosinophilic granulocytes. These results demonstrate the multilineage stimulatory properties of the protein encoded by the human cDNA clone D11 and its action on developmentally early, multipotent hemopoietic cells.

With respect to AML stimulation, AML blasts of five patients were stimulated with the COS/pLB4 CM and assayed for a response by measuring $^3$H-TdR incorporation and colony formation. Three of the five leukemia cell samples responded to the COS/pLB4 CM in both assays; characteristic dose-response relationships for colony formation and DNA synthesis of AML blasts of different patients were obtained. The responses to GM-CSF demonstrated further phenotypic differences among the leukemias responding to the COS/pLB4 CM.

These data demonstrate that the D11 cDNA clone contains the complete genetic information for a biologically active protein which is exported into the culture medium in the transformed COS cells. Despite the apparent lack of homology with respect to the protein sequence between the human protein and mIL-3 (less than 30%), the proteins are comparable with respect to their biological function. Both proteins exert their effect on developmentally early hemopoietic progenitors of various lineages. The low homology at the amino acid level is also reflected in a low homology in the coding nucleotide sequence. However, very unexpectedly, a rather high degree of homology—sufficient for retrieval of the human cDNA clone—occurred in the 3' untranslated region.

Southern analysis of human DNA revealed a single hybridizing gene indicating that this cDNA does not belong to a family of closely related genes.

From the foregoing results we conclude that the human cDNA insert in D11 encodes the human homolog of mIL-3. We decided to use the operational term hmulti-CSF for the protein encoded by the cDNA clone D11 in view of its major biological effect and assay.

The identification of hmulti-CSF cDNA clones by virtue of hybridization with the 3' terminal region of the mIL-3 cDNA was unexpected. Whereas homologous DNA sequences are in general predominantly in the coding region, the hmulti-CSF sequence has extensively diverged (45% homology) in this part of the gene. Analysis of the highly conserved domain in the 3' terminal noncoding region reveals the occurrence of 5 ATTTA repeat units which are all preserved in the mIL-3 cDNA (FIG. 1).

hmulti-CSF and mIL-3 display considerably less protein homology than other murine and human growth factors or lymphokines such as GM-CSF (Schrader et al., 1986), interleukin-2 (Schrader et al., 1986), interleukin-1 (March et al., 1985) and interferons (Higashi et al., 1983; Dijkema et al., 1985; Zwarthoff et al., 1985). The biological activity of the mature mIL-3 appears to be contained in the first 79 amino acids, including an absolute requirement for the cysteine residue at position 17 (Clark-Lewis et al., 1986). This cysteine residue is conserved in hmulti-CSF (FIG. 1, pos. 16) and may play an essential role in protein folding. The occurrence of a potential glycosylation site around this cysteine residue may interfere with disulfide bridge formation.

C. Production and Formulation of hmulti-CSF

Applicants have provided a representative variety of expression systems capable of producing human IL-3 protein in a variety of forms—as fusion proteins, as mature intracellular proteins, and as secreted proteins. Applicants are unaware of availability anywhere in the art of recombinant forms of human IL-3, or, indeed, of any human IL-3 in a preparation which is free of proteins normally accompanying this desired protein. Accordingly, the invention herein provides, for the first time, the human IL-3 protein in a manner which is capable of adaptation to therapeutic and diagnostic uses.

The human IL-3 can be produced as a fusion protein with sequences heterologous to the human IL-3 amino acid sequence. By "heterologous" is meant a sequence which is not found in human IL-3 itself, but is an unrelated sequence. This heterologous sequence may be derived from a bacterial protein, a yeast protein, a mammmalian protein, or any of a variety of miscellaneous fortuitously encoded sequences such as, for example, those encoded by polylinkers. It is clear from the results hereinbelow that at least the first 14 amino acids of the N-terminus of the human IL-3 sequence can be replaced by a heterologous sequence, at least if the fusion protein is further extended past the N-terminus.

Heterologous gene expression has been found to be a particularly useful method for producing the subject proteins. For example, host signal sequences can be fused to mature hIL-3 coding sequences in conjunction with strong promoters in Bacillus. Likewise, strong promoter/enhancer combinations and mRNA stabilizing sequences on BPV-1-derived vectors in such cell lines as C127, CHO and FR3T3 are also useful. These and other heterologous expression systems are described more fully in the examples.

The protein can also be obtained as a mature intracellular protein by constructs in which the ATG start codon is placed immediately upstream of the desired N-terminus. These intracellular proteins, whether mature or fusion proteins, can be recovered by lysing the cells and purifying the human IL-3 using standard protein purification techniques.

Protein purification is simplified if the human IL-3 is secreted into the medium. When produced in mammalian cells with which the native signal sequence is compatible, this native signal sequence can be used to effect secretion into the medium. In bacterial or yeast systems, signal sequences compatible with these hosts, such as the penicillinase or alpha-amylase sequence in bacteria or the alpha-factor signal sequence in yeast can be used.

When produced recombinantly, the human IL-3 is free of proteins normally accompanying it, and can be purified from the proteins and other materials indigenous to the recombinant host using, for example, chromatographic methods, gel filtration, ammonium sulfate precipitation, and so forth. A combination of hydrophobic interaction, ion-exchange chromatography, and gel filtration has proved to be an extremely powerful method for obtaining substantially pure hIL-3. The hydrophobic interaction may be performed using a TSK-butyl or octyl Sepharose column, on which hIL-3 can be eluted with gradients of either $(NH_4)_2SO_4$ in Tris-HCl or ethylene glycol. Contaminating substances can be removed by ion-exchange chromatography, using, for example, TSK-DEAE or TSK-CM columns. Finally, gel filtration using Biogel A has proved to be an excellent step in purification of unglycosylated hIL-3.

As described hereinbelow, the protein is useful for therapeutic and diagnostic purposes. For therapeutic uses, the protein may be formulated in ways standard for pharmaceutical compositions which are used for the administration of proteins. Suitable excipients include, for example, physiological saline, Ringer's solution, and so forth. Alternate formulations, including solid formulations (e.g., lyophilized), can also be employed.

D. Preparation of Antibodies

The availability of recombinant IL-3 protein or parts thereof will permit production of antibodies directed against the protein or parts thereof, as demonstrated hereinbelow. Such antibodies are useful, inter alia, for in vitro detection of colonies producing hIl-3, such as in quantitative or qualitative ELISA tests, for therapeutical use and for the purification of both natural and recombinant hIL-3.

Statement of Utility

The nucleotide sequence of the whole or parts of the cDNA of human IL-3, or closely-related DNA sequences will advantageously enable the detection of genetic abnormalities, including genomic rearrangements, restriction fragment-length polymorphisms, mutations and altered gene expression with the use of such techniques as the analysis of chromosomal DNA using restriction enzymes, DNA and RNA blotting as well as hybridization techniques (Maniatis et al., 1982) and two-dimensional gel electrophoresis (Fisher and Lerman, 1983).

The recombinant hmulti-CSF as provided by the present invention will facilitate a detailed analysis of its role in human hemopoiesis, in particular the possible synergism of hmulti-CSF and various other HGFs. Furthermore, hmulti-CSF is of considerable interest because of its applicability for in vitro diagnosis of human diseases in which hemopoietic progenitor cells are involved, which include leukemia, as well as potential therapeutic applications aimed at expansion of hemopoiesis in vivo. The effect of hmulti-CSF on various hemopoietic malignancies with respect to terminal differentiation of the leukemic cells also needs to be explored. In addition hmulti-CSF may be required for establishing a proliferative state of human stem cells in gene therapy protocols, since stimulation with mIL-3 was shown to be required for successful infection of mouse stem cells with recombinant, replication defective retroviruses.

IL-3 protein can also advantageously be used for the detection of early hemopoietic precursor cells in standardized in vitro cultures (Wagemaker and Visser, 1980; Merchav and Wagemaker, 1984; and Metcalf, 1986).

IL-3 protein and variants can further be used for the multiplication of hemopoietic stem cells in vitro, possibly in conjunction with other growth factors, for bone marrow transplantation and the genetic manipulation of stem cells (Lowenberg and Dicke, 1977; Wagemaker and Peters, 1978; Lemischka et al., 1986).

The IL-3 protein can be used for the determination of the response pattern of malignant hemopoietic cells in in vitro tests (Touw and Lowenberg, 1985; Griffin et al., 1986; Griffin and Lowenberg, 1986).

The IL-3 protein can further be used for the detection of remaining leukemic cells by in vitro methods (Touw et al., 1986; Griffin et al., 1986; Griffin and Lowenberg, 1986).

Furthermore, the IL-3 protein can be used in vivo for the treatment and prevention of malignant and non-malignant disorders, either by itself or in combination, in which an obtained specific response by the hemopoietic system can result in a clinical benefit.

These applications include: cytopenias and/or immunosuppression due to infections such as AIDS; cytopenias due to chemotherapy and/or irradiation; bone disorders such as bone fractures and osteoporosis; immunodeficiencies due to general anaesthetic procedures; recovery following bone marrow transplantation; adjunct to vaccinations and adjunctive therapy of infections.

The cloned human IL-3 DNA sequence or closely related DNA can be used for gene therapy in genetic deviations from the normal IL-3 gene.

To facilitate the above-described analysis, a large quantity of human IL-3 is required. The easiest way to obtain sufficient amounts of the protein is the production with microorganisms, in particular yeasts, bacteria and fungi, e.g., Saccharomyces, Kluyveromyces, Aspergillus, Streptomyces, Bacillus and *E. coli* species. Production in mammalian and other eukaryotic systems, such as C127 cells, CHO cells, FR3T3 cells, Spodoptera cells, and transgenic animals and plants, is also possible for skilled persons following the teaching of the present invention. These possibilities are all included within the scope of this invention.

As an illustration of how to obtain living cells that produce the human IL-3 protein by expression of the hIL-3 cDNA, a number of plasmids were constructed and transferred to *E. coli, B. subtilis, B. licheniformis, S. cerevisiae, K. lactis,* C127 cells, CHO cells, and FR3T3 cells. Using these host strains, the production of recombinant human IL-3 was achieved. The products were tested for their capacity to stimulate human AML blasts as described above for the COS/pLB4-conditioned medium. From these experiments it appeared that the proteins made were biologically active.

The following examples are intended to illustrate but not to limit the invention.

EXAMPLE 1

Retrieval of cDNA Encoding Human multi-CSF (hmulti-CSF)

Human leukocytes stimulated with TPA (5 ng/ml) and ConA (10 ug/ml) produced considerable amounts of HGFs as measured by the murine stem cell proliferation assay and various other colony assays. Cells were harvested 24 hours after stimulation, because mRNA production is often transient following stimulation with phorbol esters and lectins. Already after 24 hours, HGFs were easily detectable in the CM.

mRNA Preparation

Cells were harvested, washed with PBS and homogenized in guanidinium isothiocyanate solution (Maniatis et al., 1982). RNA was pelleted through a cesium chloride cushion. Oligo(dT)-cellulose chromatography was used for selection of mRNAs (Maniatis et al., 1982).

cDNA Synthesis cDNA was synthesized essentially according to Gubler and Hoffman (1983), using oligo(dT) as primer and AMV reverse transcriptase. Second strand was synthesized with RNaseH and *E. coli* DNA polymerase I. Gaps were closed with T4-DNA ligase and ends were flushed by T4-DNA polymerase. To protect internal EcoRI restriction sites, the cDNA was methylated with EcoRI methylase. Subsequently, the cDNA was ligated to phosphorylated EcoRI linkers with T4-DNA ligase. After digestion with EcoRI, excess linkers were removed by Sepharose CL-4B chromatography. The material recovered in the void volume of the column was larger than 250 bp and was used for construction of the libraries.

Construction of the Phage cDNA Library

The cDNA was ligated to lambda gt10 phage arms (Huynh et al., 1985) and packaged with commercial packaging extracts (Gigapack, Vector Cloning Systems). The recombinant phages were propagated in *E. coli* C600 hfl. cI Screening of the Phage Library Of each plate containing 1–5000 plaques, two nitrocellulose filter replicas were made according to standard procedures. Filters were then hybridized with radiolabeled mIL-3 probe from the HindIII-XbaI fragment of mIL-3 cDNA or with the complete mIL-3 cDNA clone radiolabeled with random primers. The mIL-3 cDNA clone (pL101) was isolated from a WEHI-3B cDNA library. WEHI-3B mRNA was isolated using the guanidinium isothiocyanate CsCl method, size fractionated on sucrose gradient and injected into *Xenopus laevis* oocytes. RNA fractions inducing the oocytes to produce a factor capable of supporting murine stem cell proliferation, were used for synthesis of cDNA as described above, cDNA was tailed with dC residues and inserted in the PstI site of pUC9. mIL-3 clones were identified using synthetic oligonucleotides (from published mIL-3 sequence; Fung et al., 1984). Insert of pL101 was purified on polyacrylamide gel and used for screening of the human cDNA library. Probe DNA was labeled using the random primer method (Feinberg and Vogelstein, 1983). Potential positive plaques were rescreened and plaque purified. In this way four clones were identified, including phage D11.

Sequencing of cDNA Clones

Recombinant phages were grown at large scale and purified, cDNA inserts were removed from the phage arms by digestion with EcoRI and purified on polyacrylamide gel. The purified fragments were ligated into M13mp18 and pTZ18R DNA digested with EcoRI and used for transformation of *E. coli* JM109. Single-strand DNA was prepared and sequenced according to established procedures (Sanger et al., 1977). Sequence data were analyzed using various computer programs (Queen and Korn, 1984; Staden, 1982; Devereux et al., 1984; Lipman and Pearson, 1985).

The sequence obtained for the insert in phage D11 is shown in FIG. 1. This 910 bp sequence contains the entire coding region for hmulti-CSF and its signal sequence, and exhibits high homology to the murine clone pL101 in the 3' untranslated region. The homology upstream in the coding sequence is relatively more limited. As described above, the protein has a putative 19 amino acid signal sequence followed by a 133 amino acid mature protein containing two glycosylation sites (15–17 and 70–72) and two cysteine residues at 16 and 84.

The deduced amino acid sequence is the same as that encoded by the genomic DNA disclosed by Yang et al. (1986) except for one amino acid—that at position 8 of the putative mature protein; the Yang DNA encodes Ser, the cDNA herein encodes Pro.

The intronless sequence obtained in the phage D11 can be used for prokaryotic expression, as well as for expression in eukaryotic systems, as illustrated below.

EXAMPLE 2

Expression in Mammalian Cells

A. Construction of The Eukaryote Expression Vector pLB4

Phage D11 (containing the longest cDNA insert) was digested with HindIII and BglII and subcloned in plasmid pT1 (a derivative of pTZ18R, containing some additional restriction sites in the multilinker; see Example 3A). Clones containing the phage fragment containing the cDNA insert were identified by restriction analysis. The cDNA insert was removed from this plasmid by partial digestion with EcoRI and purified by polyacrylamide gel electrophoresis. The appropriate fragment was inserted in a eukaryote expression vector (pLO) in an SV40 transcription unit.

pLO comprises: EcoRI (filled in)-PstI of pBR322 (1–755), PstI-AvaI of pBR329 (756–1849), AvaI-PvuII adapter (1850–1868), PvuII-HindIII (filled in) of SV40 promoter (1869–2211), PvuII-BamHI adapter containing the unique EcoRI site (2211–2251), MboI "splice fragment" of SV40 (2252–2861), BclI-BamHI (filled in) "poly A fragment" of SV40 (2862–3098), PvuII-HindIII promoter fragment of SV40 (3099–3440), HindIII-BamHI Eco gpt gene (3441–4501), MboI "splice fragment" of SV40 (4502–5111), and the BclI, BamHI (filled in) "poly A fragment" of SV40 (5112–5348).

The Eco gpt transcription unit is of no importance in transient expression of proteins in COS 1 cells. The resultant expression plasmid for hmulti-CSF was termed pLB4 and was purified on CsCl. This plasmid in *E. coli* was deposited with the Centraal Bureau of Schimmelcultures (CBS), Baarn, the Netherlands, under the provisions of the Budapest Treaty on Dec. 12, 1986, under CBS 568.86. The construct is shown in FIG. 2.

B. Expression of hmulti-CSF in COS 1 Cells and Bioassays pLB4 DNA was transfected to COS 1 cells using the calcium phosphate coprecipitation method (Wigler et al., 1978). Cells were cultured for 48–72 hours in alpha medium containing 10% fetal calf serum. The culture medium was recovered, filtered, and used in assays for establishing its biologic activity. Human bone marrow progenitor colony assays and acute myeloid blasts colony and proliferation assays were performed as follows. Bone marrow was obtained from hematologically normal adult volunteers by posterior iliac crest puncture following informed consent. The mononucleated cells were separated by density gradient centrifugation on a Ficoll gradient (Nijegaard and Co., Oslo, Norway), washed and resuspended in Hank's balanced salt solution (HBSS). Myeloid cells and T-lymphocytes were then removed. For this purpose, marrow cells were lysed following incubation with monoclonal antibodies OKT-3 (CD3; Ortho, Ravitan, N.Y.) and Vim 2 (myelomonocytic cells; Majdic et al., 1984) at saturating concentrations in the presence of rabbit complement (40%; 30 minutes, 25° C.) according to established procedures (Lowenberg and Bauman, 1984). The cells were washed two times in HBSS, resuspended in Iscove's modified Dulbecco's medium (IMDM) and cultured in the presence of autologous plasma according to Fauser and Messner (1978), as described before (Delwel et al., 1986), at a concentration of $1.5-3 \times 10^4$/ml. Erythropoietin 1 U/ml (sheep, step III, Connaught, Willowdale, Canada) and COS/pLB4 CM were added as growth-stimulating activities. Results of standard cultures with phytohemagglutinin-stimulated leukocytes CM (PH-LCM) in direct comparison with CS/pLB4 CM are also given. Sixty percent of the colonies were plucked and identified by microscopic analysis. The CM from COS cells transfected with the vector without insert (pLO) failed to stimulate colony formation by itself.

Figure 3:
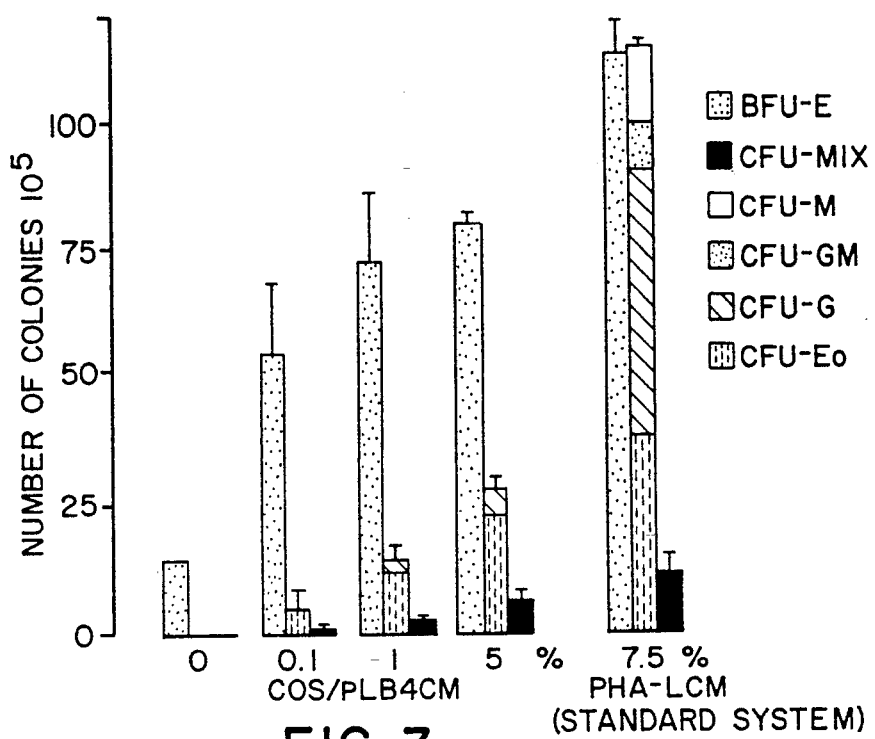
FIG. 3 shows the biological activity of COS/pLB4 CM on human bone marrow progenitors. The mean numbers of erythroid (BFU-E), granulocyte-macrophage (CFU-GM), granulocyte (CFU-G), eosinophil (CFU-Eo), macrophage (CFU-M) and mixed (CFU-MIX) colonies (±SD) are shown for duplicate cultures stimulated with graded volumes for COS/pLB4 CM.

The results are shown in FIG. 3. As shown in the figure, the mean numbers of erythroid (BFU-E), granulocyte-macrophage (CFU-GM), granulocyte (CFU-G), eosinophil (CFU-Eo), macrophage (CFU-M) and mixed (CFU-MIX) colonies (±SD) are shown of duplicated cultures stimulated with graded volumes of COS/pLB4 CM.

Induction of AML Proliferation (see FIG. 4)

Figure 4A:
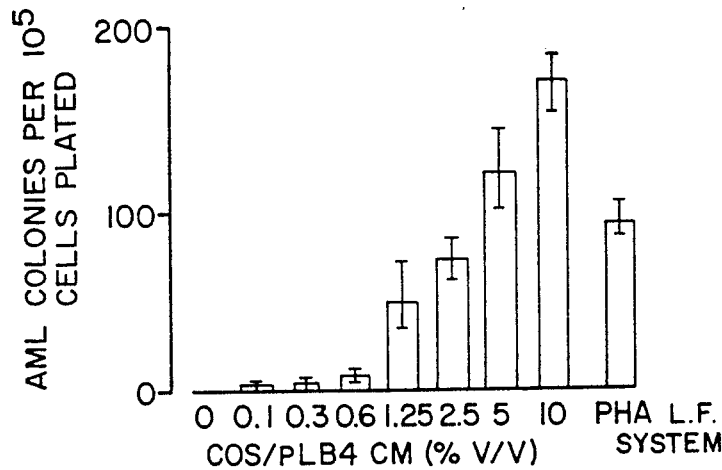
FIGS. 4A–4B shows induction of AML proliferation by COS/pLB4 CM as assessed in a colony culture assay (panel A) and in a DNA synthesis (3H-TdR incorporation) assay (panel B).
Figure 4B:
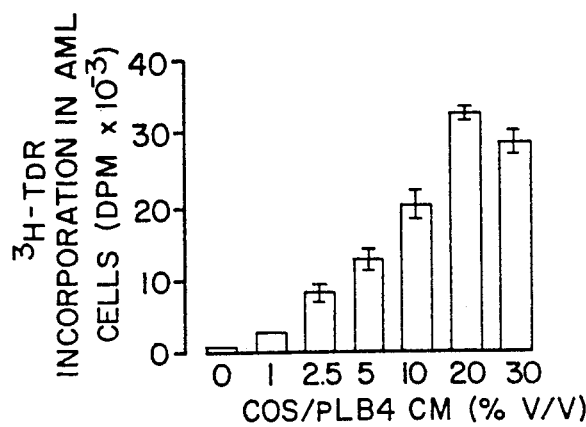

AML blasts were purified using a bovine albumin (BSA) density gradient. Residual T-lymphocytes were removed from the AML samples by E rosette sedimentation (Lowenberg et al., 1980; Swart et al., 1982; Swart and Lowenberg, 1984). AML (patient 1) colony formation was determined not only in the established PHA leukocyte feeder (PHA 1.f) system, but also in a modified version of the technique in which the leukocytes were replaced by COS/pLB4 CM, permitting assessment of its colony-stimulating activity (Lowenberg et al., 1980; Lowenberg et al., 1982; Swart et al., 1982; Swart and Lowenberg, 1984) as shown in FIG. 4A. All experiments were performed in triplicate. DNA synthesis of AML blasts (patient 2) was assayed by thymidine uptake as described (Touw et al., 1986) with results shown in FIG. 4B. Both assays showed a dose dependent relationship to COS/pLB4 CM added. Addition of control COS medium did not affect AML proliferation in either assay.

C. Construction of Eukaryotic Expression Vector pLB4/BPV

In order to establish stable cell lines expressing human IL-3, C127 cells (ATCC CRL 1616) were transfected with a derivative of pLB4. This derivative was constructed by insertion of the entire BPV-1 genome (Chen et al., 1982) into pLB4 by the following strategy. The BPV-1 BamHI fragment was excised from the vector pdBPV-MMTneo(342-12) (Law et al., 1983). The BamHI sticky ends were filled in using Klenow polymerase. Then the vector pLB4 was cleaved at the unique EcoRV site within the Eco gpt gene. Subsequently, the blunt-ended BPV-1 fragment was cloned into the EcoRV-cleaved pLB4, resulting in the vector pLB4/BPV, which is able to replicate in C127 cells.

pLB4/BPV was transfected to C127 cells using the calcium phosphate precipitation method (Wigler et al., 1978). The transfected cells were cultured for 16 days, after which foci were picked from the culture dishes. Several independent cell lines were established. The pLB4/BPV vector appears to be stably maintained within the cells, as judged by Southern blotting of Hirt extracts (Hirt, 1967) of several cell lines. Conditioned culture medium was tested for IL-3 activity using the AML proliferation assay. The stable cell lines produce active human IL-3.

D. Construction of Eukaryotic Expression Vectors pGB/IL-328, pGB/IL-329 and pGB/IL-330

An expression vector with elements similar to those in p8-4 of Sarver et al. (1985) was constructed. This vector contains a pML2 sequence (BamHI-ClaI, 2623 bp) and the Moloney murine sarcoma virus (MSV) enhancer fused to the mouse metallothionein I (MT) promoter. This fusion is described by Sarver et al. (1985). The vector also includes the SV40 polyadenylation signal, as in Sarver et al. (1985), and the complete BPV-1 genome.

To construct the desired hIL-3 expression vector, the hIL-3-encoding AvaII-AvaI fragment from pLB4 (with the AvaI site filled in by Klenow polymerase) was cloned into EcoRI/SmaI-cleaved pTZ18R (Pharmacia), together with a synthetic DNA fragment composed of the following two oligonucleotides:

```
              10         20         30         40         50
5'-AATTCAGATC TAAAAATGAG CCGCCTGCCC GTCCTGCTCC TGCTCCAACT CCTG-3'
              10         20         30         40         50
       5'-GACCAGGAGT TGGAGCAGGA GCAGGACGGG CAGGCGGCTC ATTTTTAGAT CTG-3'
```

The resulting plasmid, pGB/IL-327, was subsequently cleaved with BglII and BamHI, and the hIL-3-encoding fragment was isolated and cloned into the unique BglII site of the expression vector described above. The resulting vector was named pGB/IL-328. In this new hIL-3 expression vector, pGB/IL-328, the BglII recognition sequence is followed by 4 A-residues after which the ATG initiation codon is placed. Use of the AvaI site in the 3' noncoding region of the cDNA sequence for construction of the new expression vector eliminates ATTTA repeats which have been implicated in mRNA instability (Shaw and Kamen, 1986).

pGB/IL-328 was introduced into C127 cells as described above. Stable cell lines were established which produce high levels of human interleukin-3. These cell lines have a more than 20-fold higher production level of hIL-3 than stable cell lines derived from C127 cells carrying pLB4/BPV. These cell lines allow for the efficient production of hIL-3 with mammalian-type (complex) glycosylation. pGB/IL-328 was also introduced into FR3T3 cells (Seif and Cuzin, 1977) using the methods described above. Stable cell lines were also established, although with lower frequency. The obtained cell lines showed lower hIL-3 productivity than the C127 cell lines transformed with pGB/IL-328.

pGB/IL-328 was also introduced into CHO cells (Wood and Burki, 1984) using the method described earlier. Since CHO cells do not form foci upon transfection of a vector carrying the BPV-1 sequences, a co-transfection with pSV2neo (Southern and Berg, 1982) was performed in a ratio of 10:1 (pSV2neo being the minor component), enabling selection for G418 resistance. G418-resistant colonies were isolated and tested for IL-3 production. A significant amount of these clones produced hIL-3. Subsequently, a single cell cloning procedure was carried out in order to establish stable cell lines. Several cell lines were established with production levels equivalent and better than the level of the best producing C127-pGB/IL-328 lines. This unexpected result has no precedent in the prior art.

The cytomegalovirus IE enhancer/promoter combination was used for expression of hIL-3. The 815 bp BaI-SphI fragment from plasmid pES (Boom et al., 1986) was cloned into SmaI-SphI cleaved pTZ18R (Pharmacia). Subsequently a BglII site was introduced just downstream of the transcription initiation site using site-directed mutagenesis with the following oligonucleotide:

5'-GAG CTC GTT TAG TGA ACC GTC AGA TCT CCT GGA GAC GCC ATC CAC GCT GTT T-3'

An expression vector, pGB/IL-329, was constructed containing the pML2 sequence from pGB/IL-328 (BamHI-EcoRI), the CMV enhancer/promoter (EcoRI-BglII) and the SV40 polyadenylation signal (BglII-BamHI) as in Sarver et al. (1985). The final IL-3 expression construct pGB/IL-330 was made by introduction of the IL-3 encoding BamHI-BglII fragment from pGB/IL-327 into the unique BglII site of pGB/IL-329, followed by introduction of the BamHI cleaved BPV-1 genome into the unique BamHI site of this expression vector.

After introduction of pGB/IL-330 into C127 cells stable cell lines were established which produced high levels of IL-3. Expression is 2-4 times lower than with the pGB/IL-327 construct, however, pGB/IL-330 gives rise to mRNA with an extremely short 5' untranslated region of 12 nucleotides. The introduction of a larger 5' untranslated region may facilitate translation, thereby enhancing the production level.

pGB/IL-330 was also introduced into CHO cells (Wood and Burki, 1984) using the co-transfection method described above. G418-resistant colonies were picked and tested for hIL-3 production. Stable cell lines were established by single cell cloning of the positive clones. Unexpectedly the best producing cell lines were equally productive as the best CHO-pGB/IL328 lines indicating that either the short 5' untranslated region of the mRNA has no effect on the production of hIL-3 or that the CMV enhancer/promoter is more effective in the CHO cells.

The IL-3 present in the conditioned media of the established cell lines showed high activity in the biological assays described in WO 88/04691.

EXAMPLE 3

Construction of E. coli Expression Vectors

A. Construction of pGB/IL-301 (see FIGS. 5, 6, 7 and 8)

For construction of E. coli expression vectors, the following modifications were performed according to standard procedures (Maniatis et al., 1982).

Figure 5:
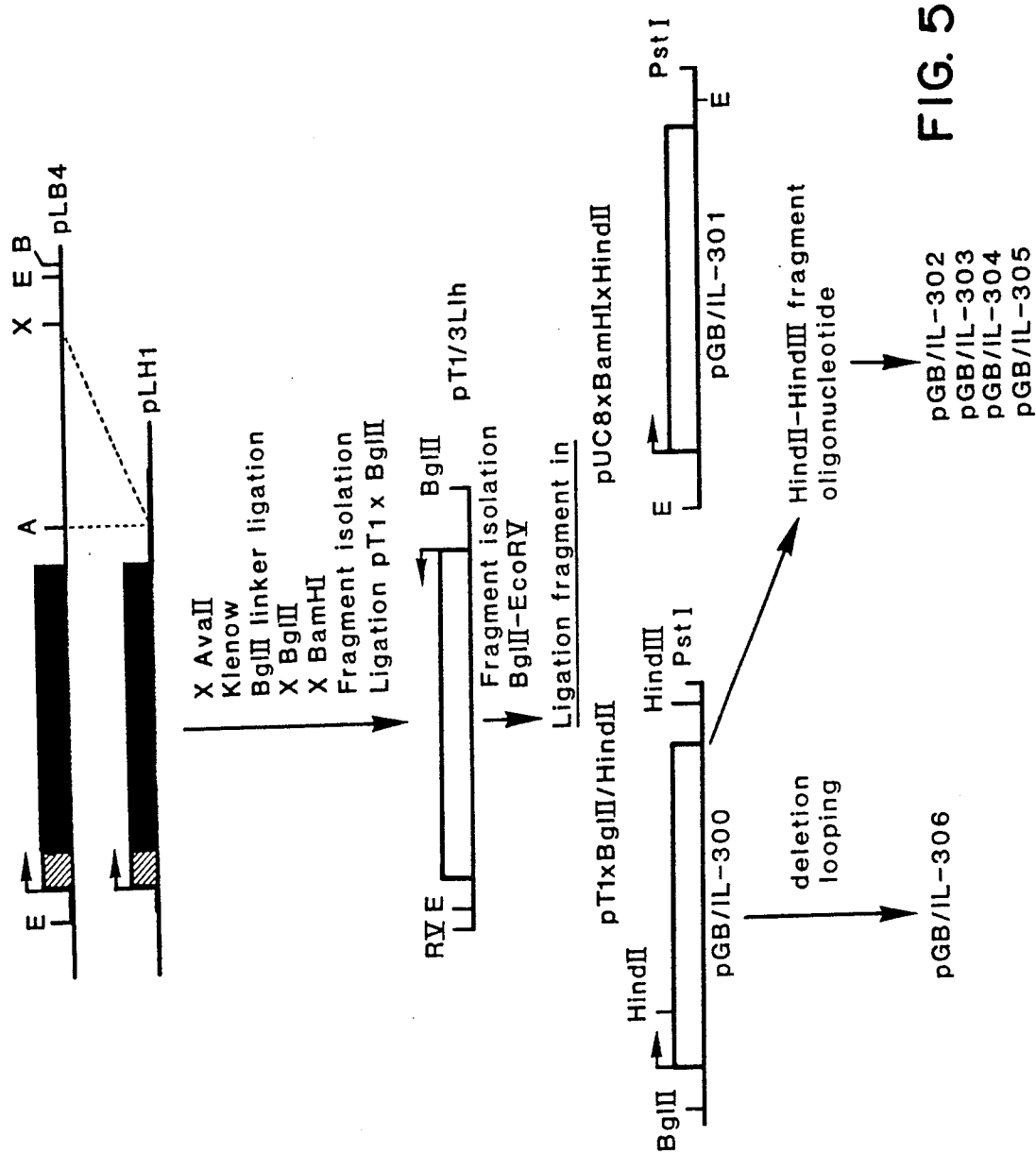
FIG. 5 shows a construction diagram of the *E. coli* expression vectors pGB/IL-301, pGB/IL-302, pGB/IL-303, pGB/IL-304, pGB/IL-305 and pGB/IL-306. In this figure, X stands for XhoI, E for EcoRI, B for BamHI and A for AvaI sites.

1. The 3'-terminal noncoding sequences between the AvaI site (position 541) and the XhoI site (position 856) in pLB4 were deleted by fusion of the DNA fragments following filling of the sticky ends with Klenow enzyme (FIG. 5).

2. For introduction of the hmulti-CSF insert into a bacterial expression vector, the following steps were performed. The pLH1 vector was digested with AvaII and the recessed ends filled with Klenow polymerase. Following ligation of a BglII linker (CAGATCTG), the DNA was digested with BglII and BamHI. The BglII-BamHI hmulti-CSF fragment was purified on polyacrylamide gel and subcloned in the BglII site of pT1, a derivative of pTZ18R (Pharmacia) modified in the multiple cloning site (see FIG. 6). Two clones were obtained, which had the insert in the opposite orientation with respect to the lacZ promoter (see FIG. 5). Inserts of these two clones were isolated on polyacrylamide gel following digestion with BglII and EcoRV and subcloned in pT1 digested with BglII and HindII.

The junction of the BglII linker and the hmulti-CSF DNA was verified by sequence analysis and showed a fusion of the linker to the AvaII site located at nt 1 of the cDNA clone (this AvaII site had arisen by ligation of the EcoRI linker to the cDNA molecule). Since this construct (pGB/IL-300) was not in phase with the lacZ protein, the BglII-EcoRV insert was subcloned into BamHI- and HindII-digested pUC8 (Vieira and Messing, 1982). The resulting construct (pGB/IL-301, see FIGS. 5, 7 and 8) was tested for production of a lacZ/hmulti-CSF fusion protein.

Figure 7:
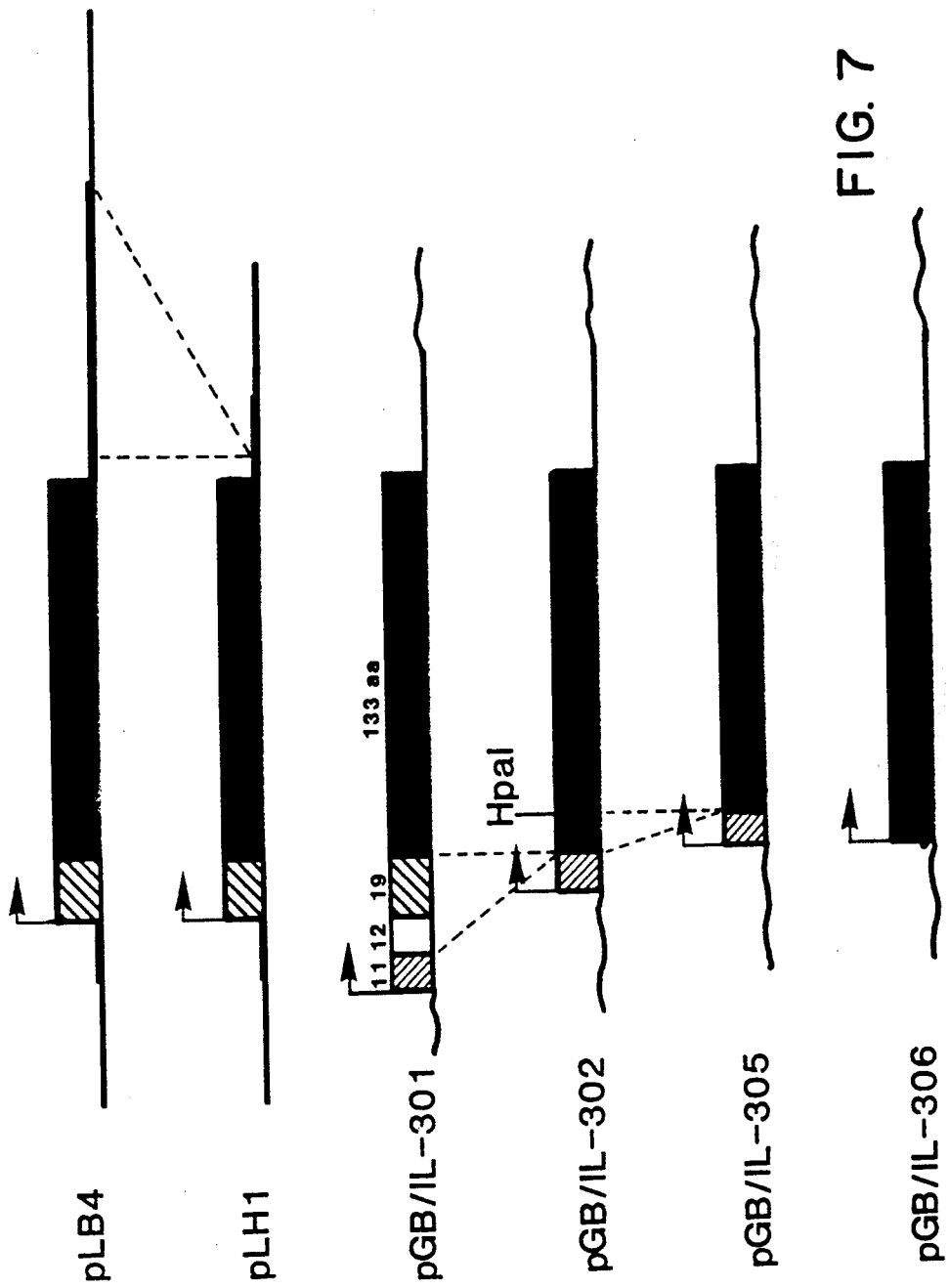
FIG. 7 shows a schematic presentation of hmulti-CSF expression clones. For the eukaryote expression plasmids pLB4 and pLH1 only the multi-CSF cDNA insert is shown. Leader peptide (▨) and mature multi-CSF protein (■) coding regions are indicated in boxes. Bacterial expression clones of hmulti-CSF (derived from pLH1) contain the lacZ and multi-linker protein coding region (▨), the 5' terminal noncoding region of hmulti-CSF (▭) and the hmulti-CSF coding region. The arrow marks the ATG start codon used in the particular vector.

B. Construction of pGB/IL-302, pGB/IL-303, pGB/IL-304 and pGB/IL-305 (FIGS. 5, 7 and 8)

Several base changes were introduced into the coding sequence for the N-terminal part of the fusion proteins by introduction of synthetic oligo nucleotides into pGB/IL-300. The new expression vectors, called pGB/IL-302, pGB/IL-303, and pGB/IL-304, were constructed as follows. The HindII-HindIII fragment of pGB/IL-300 was isolated on agarose gel and ligated to a synthetic oligonucleotide comprising the nucleotides 99-137 of hmulti-CSF and a 5' terminal SalI recognition sequence and inserted into pTZ18R digested with SalI and HindIII. The sequence of several clones was established. Indeed, several base changes were observed, resulting in modifications of the hmulti-CSF protein. Inserts of several clones were transferred to pUC8 for expression of the lacZ fusion protein (pGB/IL-302, pGB/IL-303). Clone pGB/IL-304 was made in phase with lacZ by ligation of the SalI site following filling of recessed ends with Klenow. Construction was verified by PvuI digestion. Several clones lacked a synthetic oligonucleotide and were found to be fused in frame to the lacZ protein. One example of these clones was called pGB/IL-305.

C. Construction of pGB/IL-306 (see FIGS. 5, 7 and 8)

An expression vector coding for a protein lacking the lacZ N-terminal amino acids was made from pGB/IL-300 by deletion looping as described in Osinga et al., 1983 The synthetic oligonucleotide comprised 22 nucleotides upstream of the pTZ lacZ gene including the ATG start codon and the first 24 nucleotides coding for mature IL-3. This plasmid was called pGB/IL-306 (FIGS. 5, 7 and 8).

E. coli strains containing the plasmids pGB/IL-300, pGB/IL-301 and pGB/IL-302 were deposited with CBS on Jul. 13, 1987, under CBS 377.87, CBS 378.87 and CBS 379.87.

FIG. 8 shows the sequence of fusion regions for the various plasmids constructed. The sequence of the clones is given from the start of the lacZ protein coding region in either pUC8 or pTZ18R (lower case letters)

and of the hmulti-CSF coding region (upper case letters) up to the ClaI site at position 158. Mutations in the hmulti-CSF DNA sequence are underlined, resulting in Trp$^{13}$→Arg$^{13}$ (pGB/IL-302); Leu$^9$→Pro$^9$ and Trp$^{13}$→Arg$^{13}$ (pGB/IL-303); Met$^3$→Thr$^3$ and a silent change (pGB/IL-304).

In the parent application, EP 87201322.2, filed on Jul. 13, 1987, other designations were used for these plasmids as follows:

pGB/IL-300=pT-hIL3;
pGB/IL-301=pUC/hmulti;
pGB/IL-302=pUC/hmultiDELTA1A;
pGB/IL-303 =pUC/hmultiDELTA1B;
pGB/IL-304=pUC/hmultiDELTA1C;
pGB/IL-305=pUC/hmultiDELTA2;
pGB/IL-306=pTZ/hmulti;

D. Expression of lacZ/hmulti-CSF Fusion Proteins and Nature hmulti-CSF in *E. coli*

*E. coli* strains (JM 109) carrying various expression vectors were grown in LB medium containing 50 ug/ml of ampicillin at 37° C. until an optical density of 0.5 at 550 nm was reached. Subsequently IPTG (isopropyl beta-D-thiogalactoside, Pharmacia) was added to the culture to a final concentration of 1 mM and incubation was continued for 3-4 hours.

Plasmids pGB/IL-306 and pGB/IL-302 were also transformed to *E. coli* DH1 (wild-type lacZ operon). Those strains were grown in LB medium or 2×TY medium containing 50 ug/ml of ampicillin at 37° C. for 16 hours.

Bacteria were collected by centrifugation and sonicated in buffer containing 0.1M Tris/HCl, pH 8.0; 5 mM EDTA 0.2% Nonidet P40 (NP-40) and 1 mM phenylmethylsulfonyl fluoride (PMSF) and centrifuged for 30 min at 20,000× g. Polyacrylamide gel electrophoresis of the pellet and supernatant fractions showed that the bulk of the hmulti-CSF protein is stored in the bacteria in an insoluble form.

Figure 9:
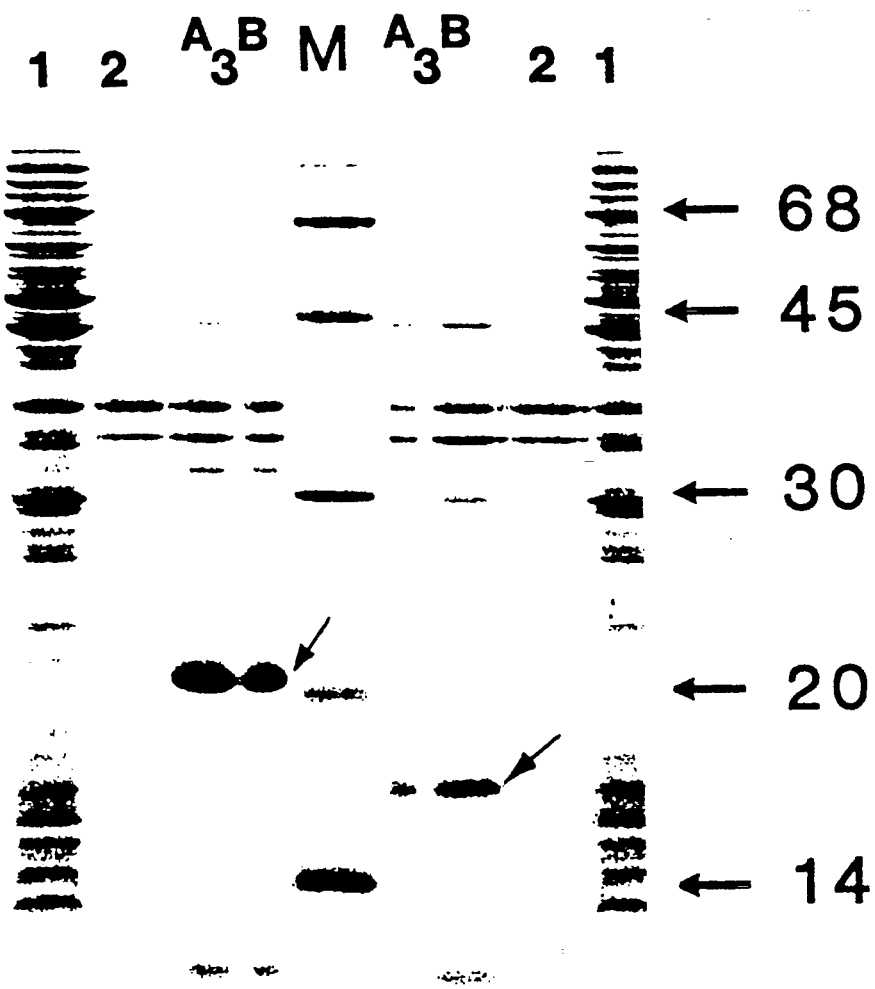
FIG. 9 shows polyacrylamide gel-electrophoresis of bacterial hmulti-CSF produced from bacteria containing pGB/IL-301 and pGB/IL-302.

The pellet was reextracted with 0.5% NP-40 buffer and finally solubilized with 8 M urea 0.1M Tris/HCl, pH 8.0 and 5 mM dithiothreitol. Thus, an extensive purification of the fusion proteins was achieved (FIG. 9).

As shown in the figure, inclusion bodies from bacteria (*E. coli*) containing pGB/IL-301 and pGB/IL-302 were isolated as described. Lanes 1 show the 0.2% NP40 supernatant (sample corresponds to 0.1 ml of the original bacterial culture). Lanes 2 show the 0.5% NP40 supernatant (0.2 ml) and lanes 3 the pellet solubilized in 8M urea buffer (A: 0.05 ml; B: 0.2 ml). The proteins were separated on a 13.5% SDS-polyacrylamide gel and stained with Coomassie Brilliant Blue. Molecular weights (in kd) of marker proteins (lane M) are denoted on the right. The human multi-CSF fusion proteins are indicated by arrows. The fusion protein encoded by pGB/IL-301 has a molecular weight, as expected, of about 20 kd; that produced from pGB/IL-302, of about 16 kd.

Figure 10:
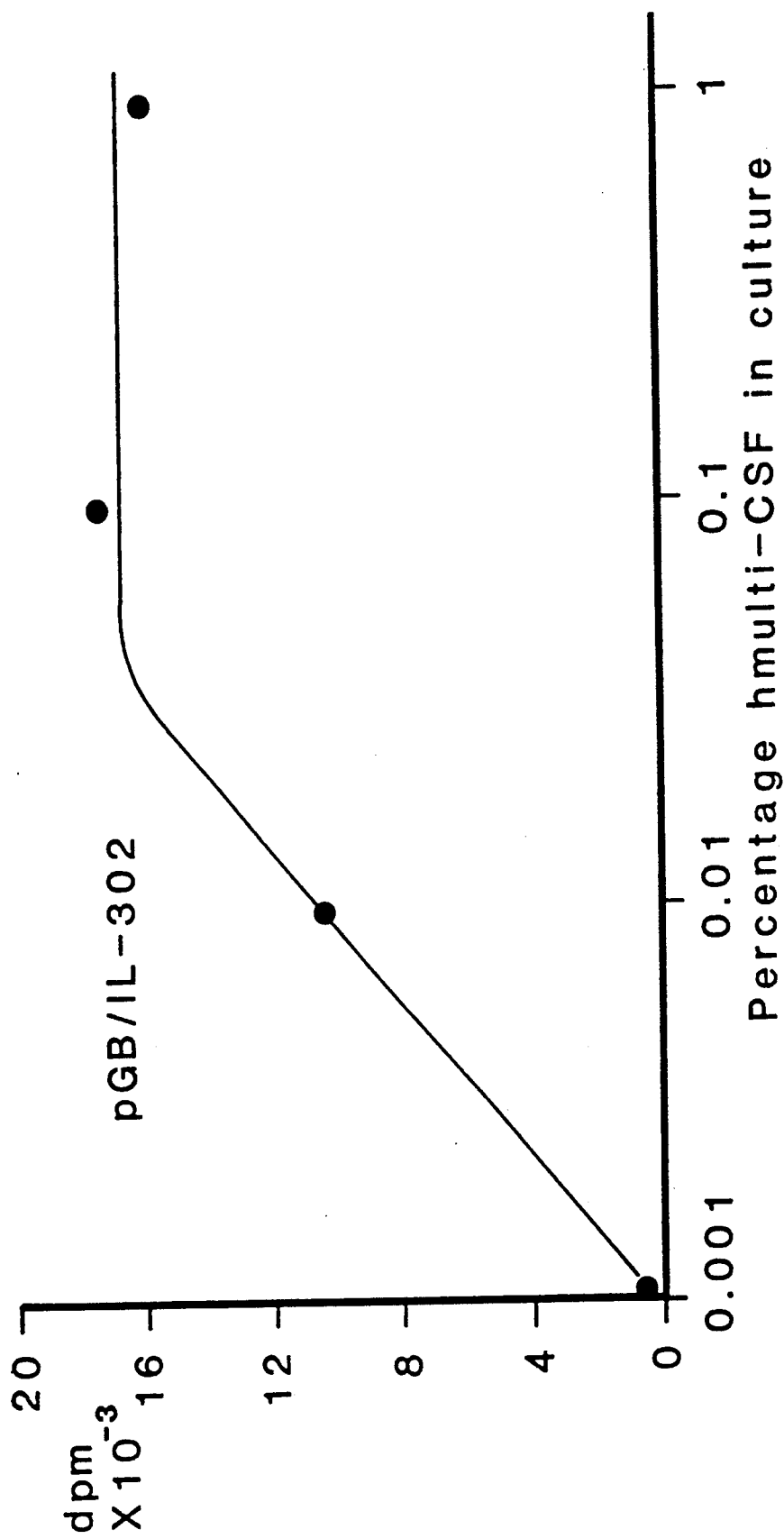
FIG. 10 shows the titration of hmulti-CSF fusion protein on AML blast cells.

E. Determination of Biological Activity of Bacterial hmulti-CSF Preparations Bacterial protein preparations were diluted in alpha medium containing 1% bovine serum albumin, filter sterilized and assayed in the AML blast proliferation assay. Diluted samples were added to purified AML blasts and cultured for four days. DNA synthesis was measured using $^3$H thymidine as described (Touw et al., 1986). One unit per ml is defined as the amount of hmulti-CSF required for half maximal proliferation of AML blasts. FIG. 10 shows this titration. Various dilutions of the urea extracted protein preparation of bacteria containing the plasmid pGB/IL-302, were assayed for the stimulation of AML blast proliferation using $^3$H-thymidine. The fusion protein concentration of this protein preparation was 33 ug/ml. Based on the presented titration curve, the activity of this preparation is 16,000 units/ml.

The amount of bacterial fusion protein in the preparations was estimated from polyacrylamide gel electrophoresis and used for calculating specific activities.

The results are shown in the following table:

TABLE 1

| Biological Activity of Bacterial hmulti-CSF Preparations | | | |
|---|---|---|---|
| | Mr (× 10$^{-3}$) lacZ/hmulti (1) | ug protein per ml (2) | Units per ml (3) | Specific activity units per mg IL-3 |
| pGB/IL-301 | 20 | 20 | 45 | 4,500 |
| pGB/IL-302/303 | 16 | 5 | 2400 | 480,000 |
| pGB/IL-304 | 18 | ND(4) | 18 | — |
| pGB/IL-305 | 16 | 1 | 300 | 300.000 |
| pGB/IL-306 | 15 | ND | 70 | ND |

1. Approximate molecular weights are estimated from the DNA sequence of the fusion protein (FIG. 8).
2. IL-3 concentrations were estimated on SDS-polyacrylamide gel and calculated per ml of starting culture.
3. Activity of urea solubilized protein was determined in the AML proliferation assay and is expressed per ml of starting culture.
4. Not determined.

From these results it was concluded that human multi-CSF expressed as a fusion protein in *E. coli* was obtained in biologically active form. The results show that changes introduced into the N-terminus of the fusion proteins may influence the specific activity of these proteins.

EXAMPLE 4

Preparation of Antibody Preparations Capable of Immunospecific Reaction with Human IL-3 Protein

A. Polyclonal Rabbit Anti-Human IL-3 Antiserum

A preparative gel was made from a lysate of *E. coli* containing the plasmid pGB/IL-301. The 21 kd band with the IL-3 fusion protein was sliced out, minced in saline with a mortar and emulsified in a 1:1 ratio in Complete Freund's Adjuvant containing 1 mg of *Mycobacterium tuberculosis* H37RA per ml. New Zealand White rabbits (spf) were immunized with 1 ml of the emulsion (with ±100 ug IL-3 fusion protein) divided over 5 injection sites (2×i.m. in the thighs, 3×s.c. on the back). Booster injections of the same antigen in Incomplete Freund's Adjuvant were given at week 2, 4 and 6. Serum was collected at week 8 by venapuncture from the ear.

One volume of serum was absorbed with 9 volumes of sonicated pUC8 containing *E. coli* (overnight at 4° C.) to remove nonspecific antibodies. Immunoblotting of all IL-3 constructs made in *E. coli, B. licheniformis, B. subtilis* and *S. cerevisiae,* and *K. lactis* showed immunospecific reaction with the absorbed sera at a dilution of 1 in 6500.

Figure 11:
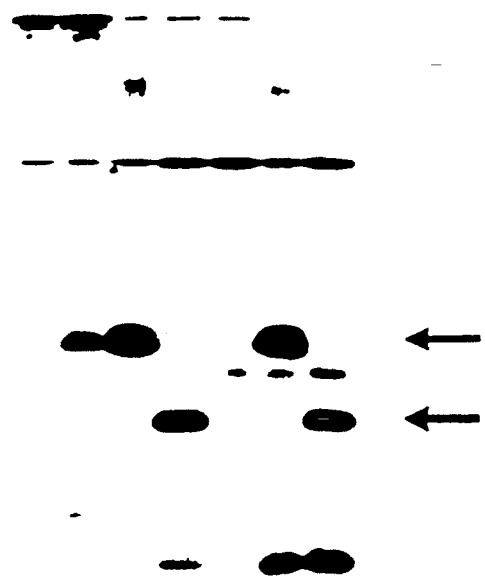
FIG. 11 shows a Western blot demonstrating the IL-3 specific reaction of rabbit antisera raised against the 21 kd protein isolated from a lysate of *E. coli* transformed with pGB/IL-301.

Some of these results are shown in FIG. 11. The proteins were isolated from the recombinant hosts as described above and were separated on a 13.5% polyacrylamide gel and blotted onto a nitrocellulose membrane. Lane 1: *E. coli* containing pTZ18R (control);

Lane 2: pGB/IL-301; Lane 3: pGB/IL-301; Lane 4: pGB/IL-302; Lane 5: pUC19 (control); Lane 6: pGB/IL-301; Lane 7: pGB/IL-302. Lanes 6 and 7 show proteins present in the pellet after the sonication of the bacteria. Lanes 3, 4 and 5 show proteins present in the pellet after the first washing step. Lanes 1 and 2 show the final urea-solubilized protein fractions.

The arrows show the fusion proteins (of the expected size) from pGB/IL-301 and pGB/IL-302.

Figure 12B:
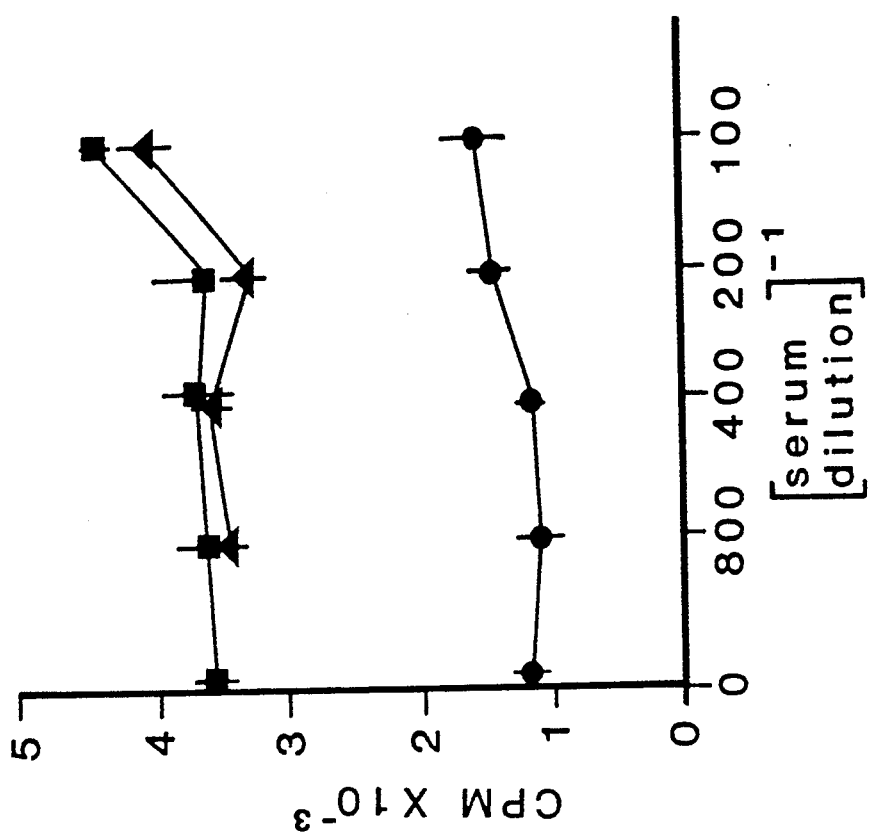
FIGS. 12A and 12B show the effect of the antisera of FIG. 11 on IL-3 activity.
Figure 12A:
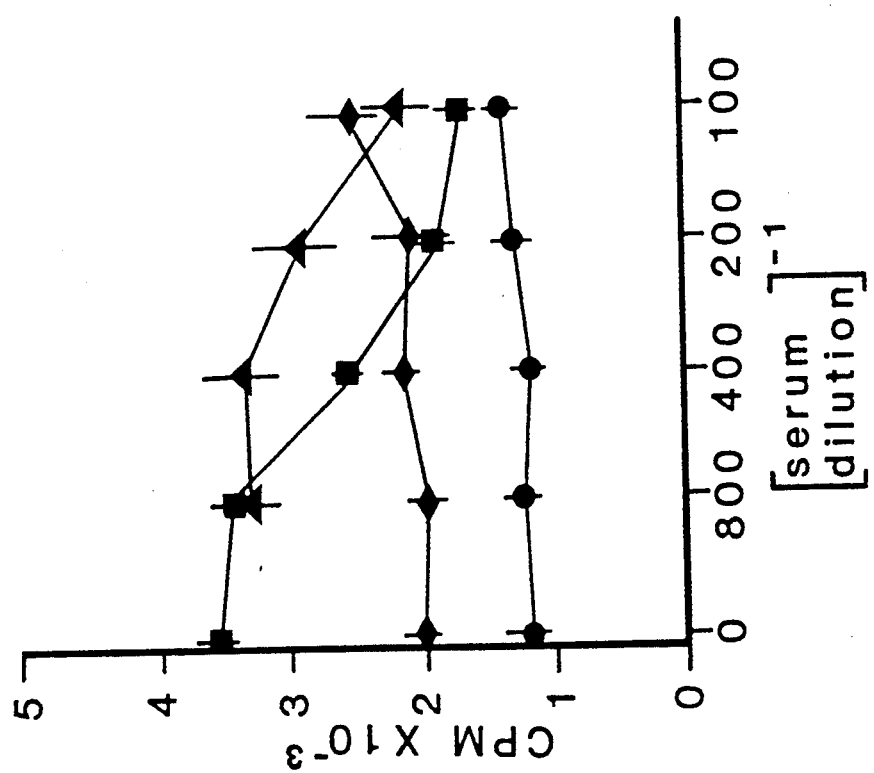

FIG. 12A shows the inhibition of IL-3 dependent proliferation of AML blast cells by anti-IL-3 antiserum. FIG. 12B shows that preimmune serum does not affect the action of IL-3 on AML blast cell proliferation. In both panels. ▲=IL-3 at 10 U/ml; ■=IL-3 at 1 U/ml; ●=control no addition.

FIG. 12A shows IL-3 dependent growth in the AML blast proliferation assay (Touw et al., 1986) was inhibited by the sera in a dose dependent manner; FIG. 12B shows preimmune sera do not have this effect. As control, GM-CSF dependent growth was unaffected by these sera in the same assay (FIG. 12A where ♦=GM-CSF at 100 U/ml.

B. Monoclonal Mouse Anti-Human IL-3 Antibodies

Balb/C mice were immunized with 3×0.1 ml (s.c.) of the same emulsion as used for the rabbits. A booster (0.1 ml i.p.) of antigen in Incomplete Freund's Adjuvant was given at week 2 and three days later spleen lymphocytes were fused with SP2/0 myeloma cells according to standard procedures (Salfre and Milstein, 1981). Hybridoma supernates were screened in the Enzyme Linked Immunosorbent Assay, using a lysate of E. coli pGB/IL-302 (containing the 17 kd IL-3 fusion product) as a positive control and a lysate of E. coli pUC8 as negative control. In total, 29 IL-3 hybridoma cultures secreting antibodies specific for IL-3 were selected and stabilized.

EXAMPLE 5

Construction of Bacillus Expression Vectors

General cloning techniques were used (Maniatis et al., 1982).

Figure 13:
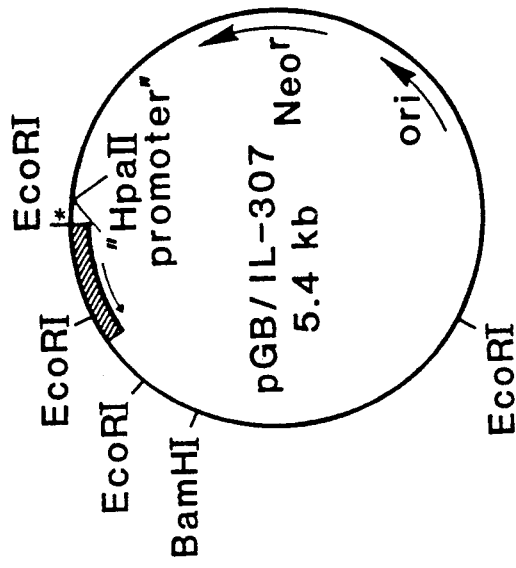
FIG. 13 shows a schematic representation of plasmid pGB/IL-307. The box (▨) indicates the human Il-3 coding sequence. The N-terminal amino acids of the fusion protein are depicted below the drawing.

A. Construction of pGB/IL-307 (FIG. 13)

For construction of pGB/IL-307 the SmaI fragment of pLB4 carrying the hmulti-CSF gene, was ligated into PvuII digested pUB110 (Gryczan et al., 1978). After transformation to competent cells (Bron and Venema, 1972) of DB105 (an spo⁻ derivative of the protease deficient strain DB104 (Kawamura and Doi, 1984), two clones were obtained, as expected; the fragment was cloned in both orientations. The plasmid that harbored the fragment in the correct orientation with respect to the so-called "HpaII promoter" (Zyprian and Matzura, 1986) was called pGB/IL-307. In this case a fusion protein will be made (see FIG. 13).

B. Construction of pGB/IL-310

An hmulti-CSF expression plasmid was prepared as described below.

Figure 14:
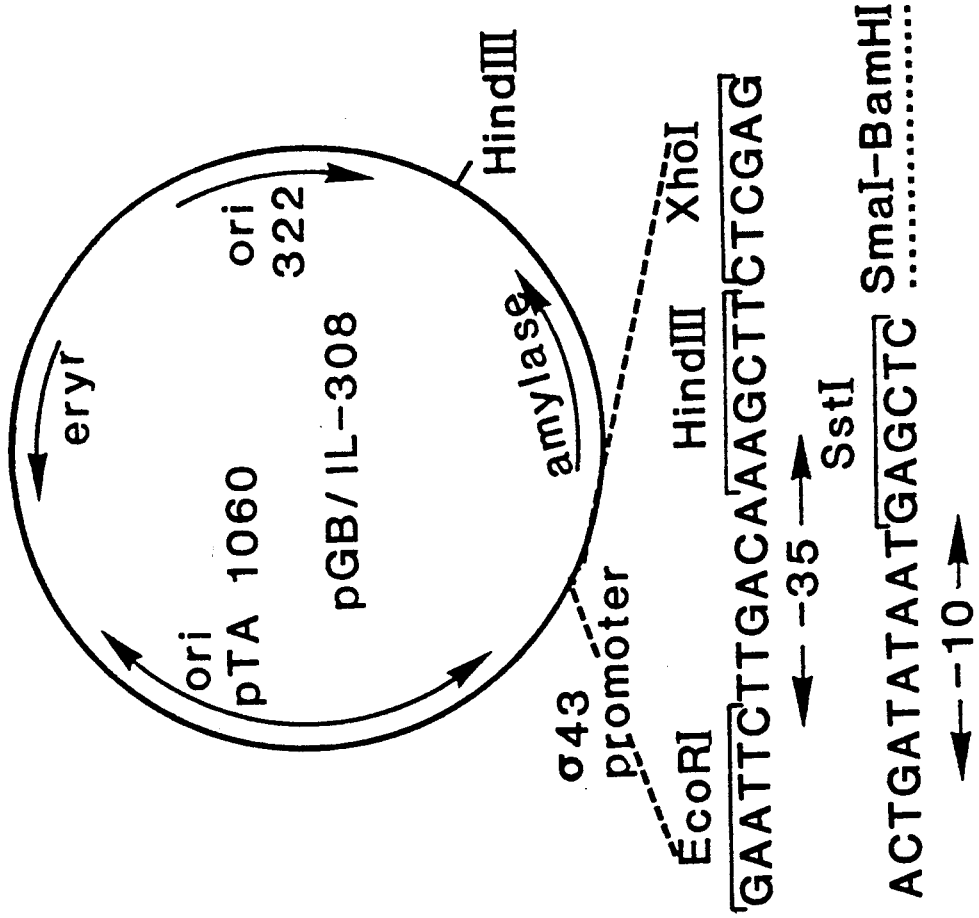
FIG. 14 shows a schematic of plasmid pGB/IL-308. The nucleotide sequence of the promoter region is depicted below the drawing.

1. Promoter Cloning (FIG. 14)

For expression in Bacillus, a synthetic sigma-43 promoter as described (EPA0024.294) is used (the promoter used to be called sigma-55).

Plasmids pPROM55s (EPA0024.294), the promoter containing plasmid, and pGPA14 (EPA0244042) were digested with EcoRI and XbaI. The promoter fragment was ligated into the vector fragment, which had been purified on an agarose gel. After transformation to E. coli (JM 101), the correct plasmid was obtained and called pGB/IL-308 (FIG. 14).

Figure 15:
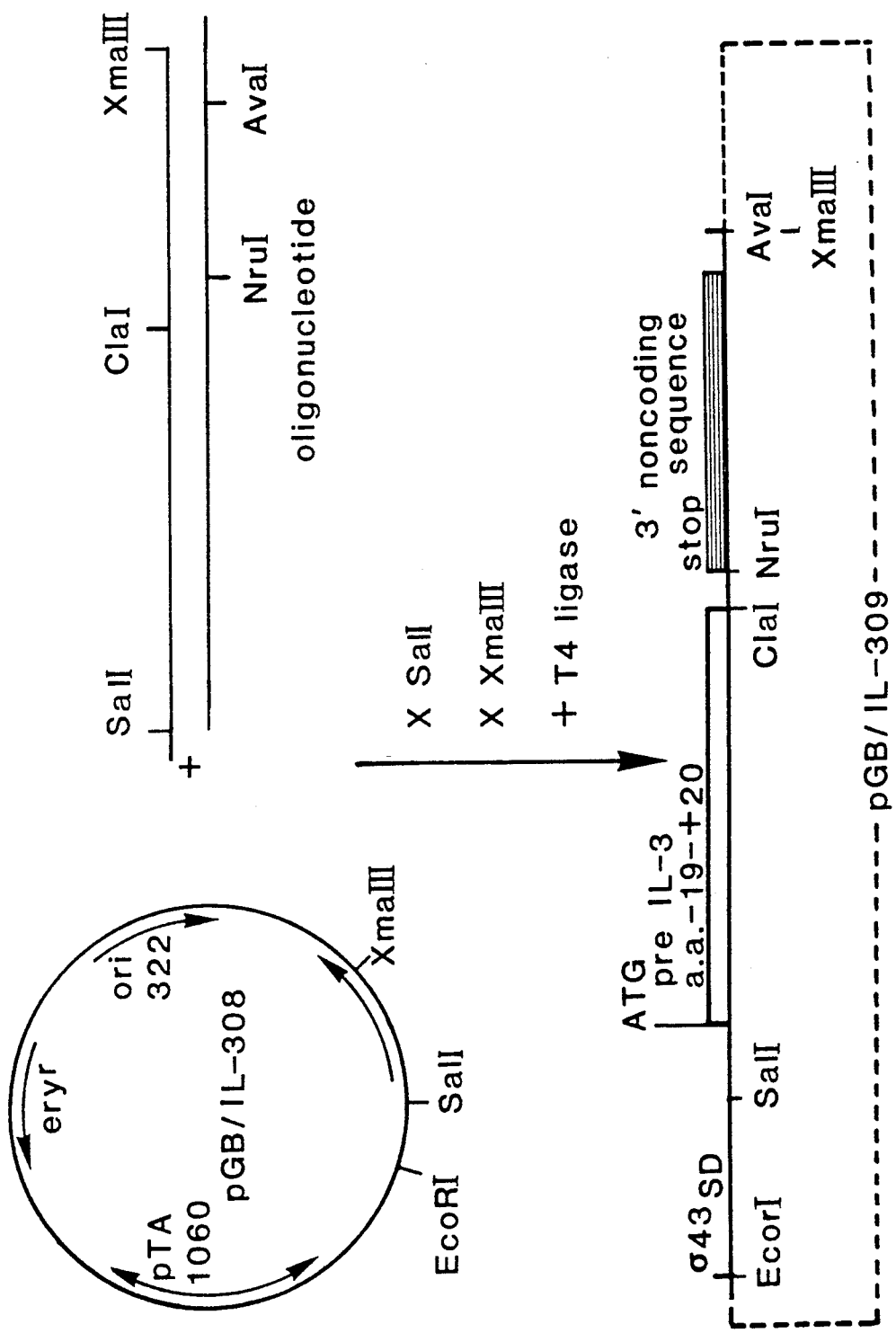
FIG. 15 shows construction of plasmid pGB/IL-309. The first box (▭) indicates a part of the human IL-3 sequence, viz., the signal sequence plus 20 amino acids of the mature protein. The other box (▨) indicates part of the 3' noncoding region of the IL-3 cDNA sequence.

2. Introduction of a Synthetic Oligonucleotide into pGB/IL-308 (FIG. 15)

A synthetic oligonucleotide comprising the nucleotides 39-158 and 484-546 of hmulti-CSF, a 5'-terminal SalI recognition sequence- and a 3'-terminal XmaIII site was ligated into SalI-XmaIII digested pGB/IL-308. The ligation mixture was introduced into JM101. After analysis of a number of transformants, the correct plasmid was found, pGB/IL-309.

Figure 16:
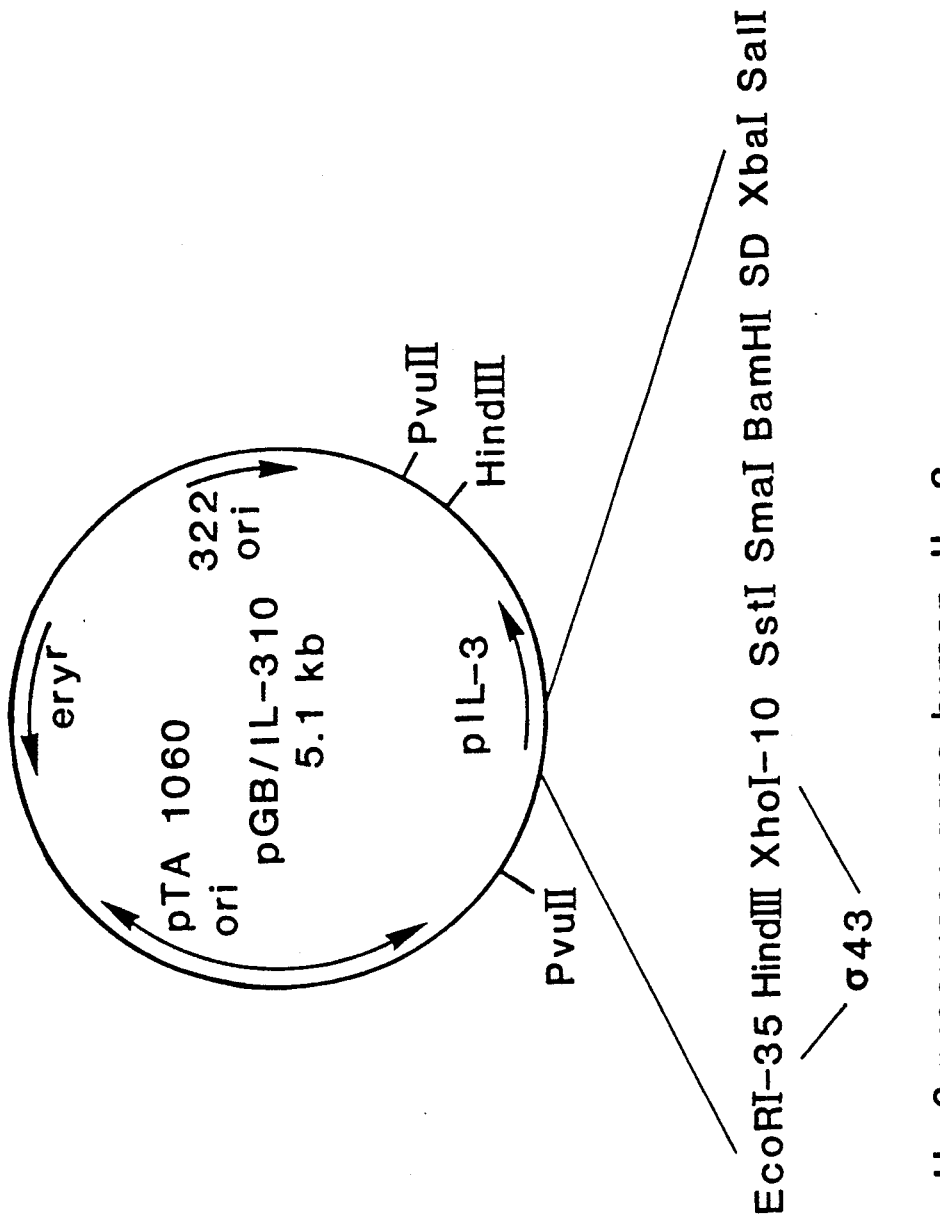
FIG. 16 is a schematic representation of plasmid pGB/IL-310.

3. Introduction of hIL3 (FIG. 16)

After transformation to and isolation from B. subtilis DB105, the plasmid pGB/IL-309 was digested with XmaIII. The recessed ends were filled in with Klenow polymerase, and the plasmid then was cleaved with ClaI. The plasmid pGB/IL-307 was digested with AvaI, the ends filled in with Klenow and then digested with ClaI. Subsequently, the hmulti-CSF containing fragment was ligated with the pGB/IL-309 fragment and transformed to JM101. The resulting plasmid was called pGB/IL-310 (FIG. 16). This plasmid harbored the hIL-3 gene with its own signal sequence. After isolation of the correct plasmid, it was also introduced into B. subtilis DB105.

C. Construction of pGB/IL-311 and pGB/IL-312 (FIGS. 17, 18)

pGB/IL-310 was partially digested with HindIII and totally with PvuII. The two hmulti-CSF containing PvuII digests were subsequently digested with HindIII and SmaI.

FIG. 17 shows the nucleotide sequence of plasmid pBHA1. The plasmid consists of positions 11–105 and 121–215; bacteriophage FD terminator (double): positions 221–307; a part of plasmid pBR322 (viz., positions 2069–2153): positions 313–768; bacteriophage F1, origin of replication (viz., positions 5482–5943): positions 772–2571; part of plasmid pBR322, viz., the origin of replication and the beta-lactamase gene: positions 2572–2685; transposon Tn903, complete genome: positions 2719–2772; tryptophan terminator (double): positions 2773–372-9; transposon Tn9, the chloramphenicolacetyltransferase gene. The nucleotides at position 3005 (A), 3038 (C), 3302 (A), and 3409 (A) differ from the wild-type cat coding sequence. These mutations were introduced so as to eliminate the NcoI, BalI, EcoRI and PvuII sites: positions 3730–3804; multiple cloning site: positions 3807–7264; part of plasmid pUB110, viz., the replication function and kanamycin resistance gene (EcoRI-PvuII fragment) (McKenzie et al., 1986; McKenzie et al., 1987): positions 7267–7331; multiple cloning site. The fragments were put together by known cloning techniques, e.g., filling in of sticky ends with Klenow, adapter cloning, etc. All data were derived from Genbank ® National Nucleic Acid Sequence Data Bank, NIH, USA.

Figure 18:
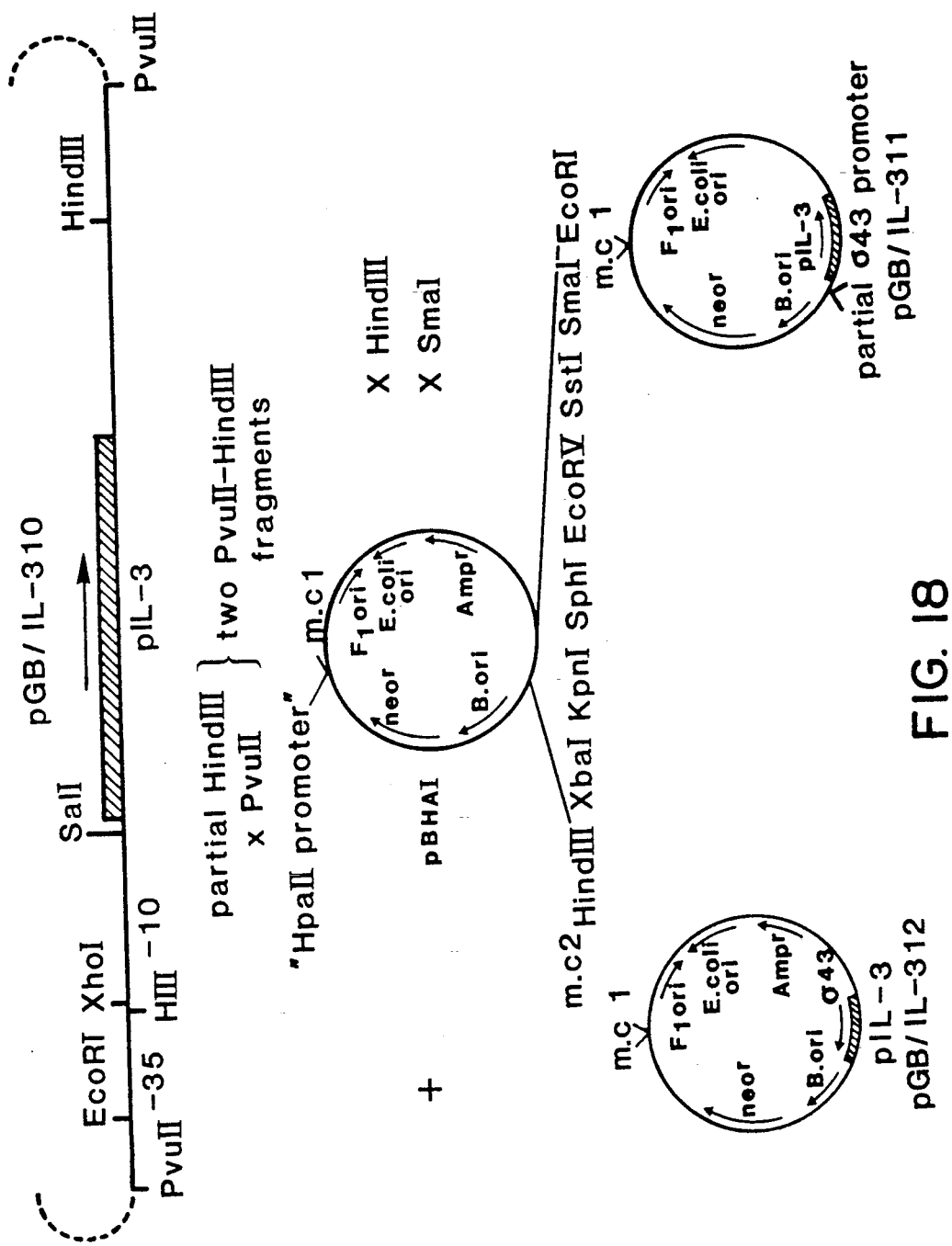
FIG. 18 shows the construction of the plasmids pGB/IL-311 and pGB/IL-312. The box (▨) indicates the precursor human IL-3 coding region.

After transformation to JM101 and analysis of a number of ampicillin resistant colonies, two different plasmids were found: pGB/IL-312, which harbored the complete gene with complete control sequences, and pGB/IL-311, which contained the complete gene and the promoter lacking the −35 region in the other orientation (see FIG. 18).

pGB/IL-311 has been transformed to *B. subtilis* DB105 and *B. licheniformis* strain T9 (DELTAamy, spo−, exoprotease negative, rif$^r$, see EPA87201379.2).

Figure 19:
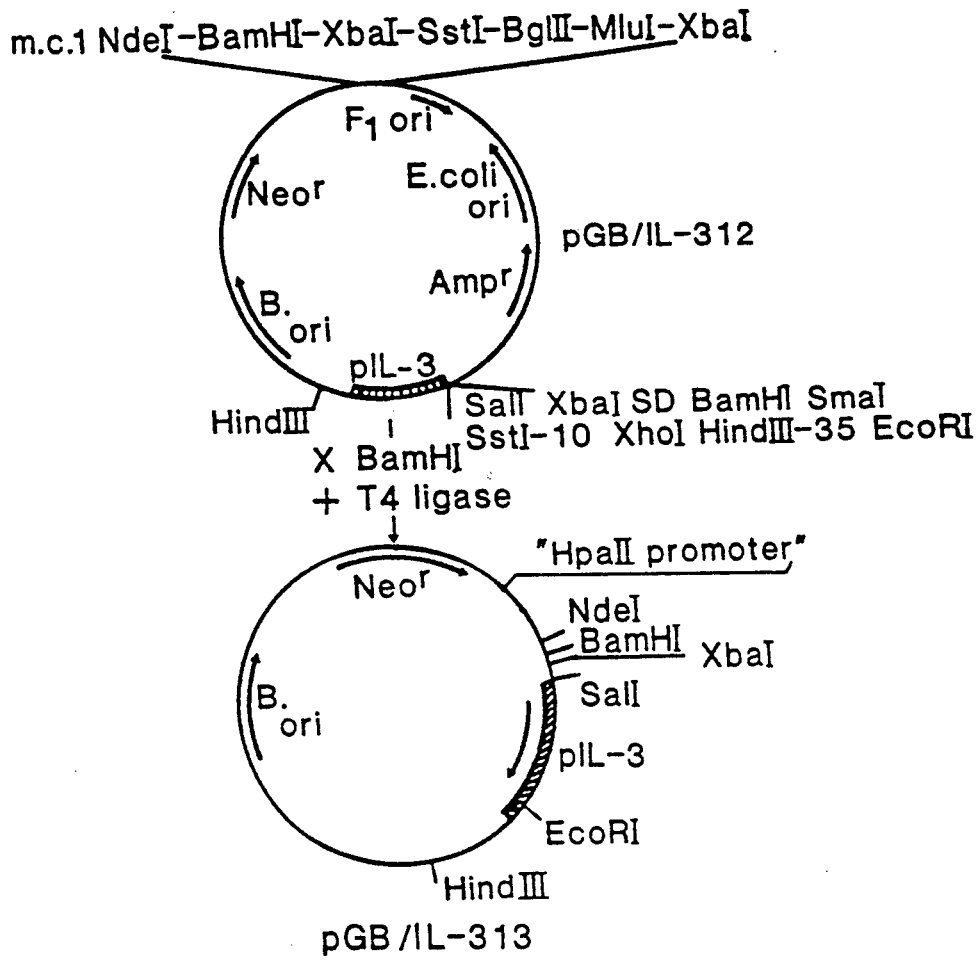
FIG. 19 shows the construction of the plasmid pGB/IL-313. The sequence at the 5' side of the IL-3 sequence is depicted below the drawings.

D. Construction of pGB/IL-313 (FIG. 19)

In order to obtain a smaller plasmid, with the hmulti-CSF gene downstream of the "HpaII promoter", pGB/IL-312 was digested with BamHI and religated. The ligation mixture was transformed into competent DB105 cells. A number of neomycin resistant colonies were analyzed and the correct plasmid was obtained. The plasmid was called pGB/IL-313.

Figure 20:
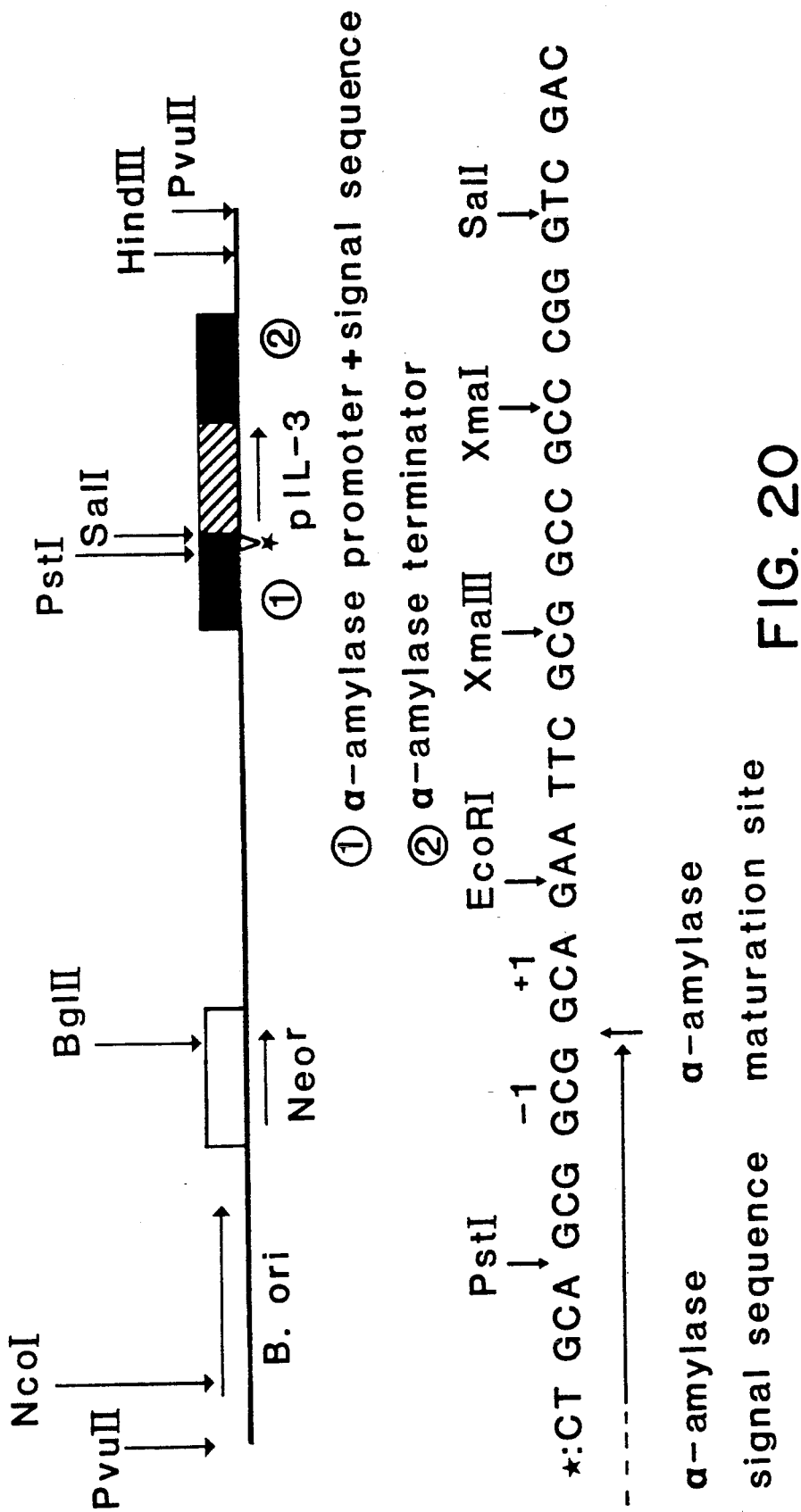
FIG. 20 shows a schematic representation of plasmid pGB/IL-317 construction.

E. Construction of pGB/IL-317 (FIG. 20)

In order to clone the hmulti-CSF gene downstream of the *B. licheniformis* alpha-amylase transcriptional and translational initiation region and signal sequence, one of the earlier-described pOL5-delta vectors (EPA87201379.2) was used, viz., pOL5-2-delta. Besides the alpha-amylase signal sequence (29 amino acids long), this plasmid harbors one amino acid of the alpha-amylase mature sequence (an Ala) followed by a multiple cloning site: EcoRI-SmaI-SalI, HindIII (EPA87201379.2).

The SalI-PvuII fragment of plasmid pGB/IL-310 containing the hmulti-CSF gene was ligated into the SalI-PvuII-digested pOL5-2-delta vector and transformed to DB105. The resulting plasmid was called pGB/IL-317 (FIG. 20). The hIL-3 gene still harbors its own signal sequence on this plasmid. The plasmid was also introduced into *B. licheniformis* T9.

F. Construction of pGB/IL-322 and pGB/IL-326

In order to obtain an improved Bacillus expression vector for human IL-3, a derivative of plasmid pGB/IL-317 was made. This plasmid contains downstream of the strong alpha-amylase promoter, in a 5'-to-3' direction, coding information for the Bacillus alpha-amylase signal sequence, extra amino acids, the IL-3 signal sequence, mature IL-3, and the 3' end of the amylase gene.

First, a perfect junction between the DNA sequence encoding the amylase signal sequence and the DNA sequence encoding mature human IL-3 was made in the *E. coli*-Bacillus shuttle-plasmid pGB/IL-311. This plasmid was cleaved with restriction enzymes SalI and ClaI. subsequently, the small fragment containing the information for the human IL-3 signal sequence was exchanged with a synthetic SalI-ClaI fragment containing the coding information for the alpha-amylase signal sequence fused to the mature IL-3 coding sequence. The resulting plasmid, pGB/IL-321, was transformed to *B. subtilis* 1A40 and to *B. licheniformis* T9. Transformants synthesize only small amounts of IL-3, but the protein is secreted into the medium.

The small PstI-ClaI fragment from pGB/IL-321 was isolated and inserted into the PstI-ClaI-cleaved plasmid pGB/IL-317, thereby exchanging the DNA sequence encoding the extra amino acids and the IL-3 signal sequence with the perfect junction of alpha-amylase signal sequence and mature IL-3 coding sequence. The resulting plasmid was designated pGB/IL-322. pGB/IL-322 gives rise to a high production of IL-3 by *B. licheniformis* T9 transformants. This was not determined for *B. subtilis* 1A40. More than 95% of the protein is secreted into the culture medium. N-terminal sequencing of the purified protein showed that the IL-3 synthesized by these transformants has the correct amino-terminus (Ala$^1$-Pro$^2$-Met$^3$ ... ).

Another new expression vector, pGB/IL-326, was constructed as follows. The HindIII-SalI fragment (HindIII end filled in using Klenow polymerase) from pGB/IL-311 was cloned into pTZ18R (Pharmacia) cleaved with SalI and SmaI, resulting in vector pGB/IL-323. Subsequently, the DNA encoding the IL-3 signal sequence was exchanged with a synthetic DNA fragment encoding the Bacillus alpha-amylase signal sequence. In this synthetic piece of DNA, the ATG start codon is preceded by the sequence CAT resulting in a cleavage site for the restriction enzyme NdeI. The SphI-KpnI fragment from this plasmid pGB/IL-324, containing alpha-amylase signal sequence, mature IL-3, and amylase terminator, was then cloned into pBAH3 cleaved with SphI and KpnI (pBAH3 is a derivative of pBAH1 lacking the PstI site in the Ap$^R$ gene). The resulting plasmid, pGB/IL-325, was subsequently cleaved with NdeI and religated, thereby fusing the so-called HpaII promoter with the alpha-amylase signal sequence and the mature IL-3 encoding sequence. The resulting plasmid, pGB/IL-326, was transformed to *B. licheniformis* T9. Transformants produced high amounts of IL-3 of which more than 95% was secreted into the culture medium. For proper secretion of mature hIL-3 by Bacillus, a perfect junction between alpha-amylase signal sequence and mature hIL-3 coding sequence appears crucial.

The mature IL-3 produced by *B. licheniformis* T9 transformants obtained with the expression vectors pGB/IL-322 and pGB/IL-326 has the correct amino acid sequence, is unglycosylated, and shows high biological activity both in AML and human bone marrow assays. Thus, surprisingly, by rearrangement of the different genetic elements with respect to each other, optimal combinations of promoters, signal sequences and mature hIL-3 coding sequences were found. pGB/IL-326 was also transformed to *B. subtilis* 1A40.

G. Expression of Eight Expression Plasmids in Bacillus Strains

*B. subtilis* and *B. licheniformis* strains carrying the expression plasmids mentioned below were grown in TSB medium containing 20 ug/ml neomycin or 10 ug/ml erythromycin at 37° C. (for 16-24 hours); 300 ug/ml of the culture was centrifuged. The pellet was resuspended in sample buffer and analyzed using polyacrylamide gel-electrophoresis followed by Western blotting. The supernatant was TCA precipitated, and the pellet was resuspended in sample buffer. Both supernatant and pellet were analyzed for IL-3 protein (see Table 2).

To determine the biological activity of the produced proteins, the following steps were carried out: the cell pellets were resuspended in a buffer containing 0.1M Tris/HCl pH 8.0 and 10 mM MgCl$_2$. Lysozyme was added to a final concentration of 1 mg/ml and PMSF to a final concentration of 1 mM. The solution was incubated for 30 min. at 37° C. Subsequently DNase (final concentration 20 ug/ml) was added and the solution was incubated for 15 min. at 20° C. Finally, the biological activity of this preparation as well as of the supernatant of the cultured cells was determined as described. The results are shown in Table 2.

TABLE 2

Expression of the Bacillus Vectors

| Plasmid | Strain | MW IL-3 Pellet (kd) | MW IL-3 Supernat. (kd) | Biological Activity Pellet | Biological Activity Supernat. |
|---|---|---|---|---|---|
| pGB/IL-307 | DB105 | 21 | — | + | — |
| pGB/IL-310 | DB105 | 15; 17 | 15; 17 | — | — |
| pGB/IL-311 | DB105 | 12.5; 15 | — | + | — |
|  | T9 | — | — | + | — |
| pGB/IL-313 | DB105 | 15; 17 | 12.5; 15 | + | — |
|  | T9 | — | — | + | — |
| pGB/IL-317 | DB105 | 12.5; 15 17; 20 | 12.5; 15 17 | + | + |
|  | T9 | 12.5; 15 17; 20 | 12.5; 15 17 | + | + |
| pGB/IL-321 | 1A40 | — | — | — | + |
|  | T9 | — | — | — | + |
| pGB/IL-322 | 1A40 | N.D. | N.D. | N.D. | N.D. |
|  | T9 | 14.5; 17 | 14.5 | + | +++++ |
| pGB/IL-326 | 1A40 | 14.5; 17 | 14.5 | + | ++ |
|  | T9 | 14.5; 17 | 14.5 | + | +++++ |

It can be concluded that in *B. subtilis,* using pGB/IL-307, a fusion protein is made that has IL-3 activity. When the human IL-3 gene only contains its own signal sequence, no significant secretion of human IL-3 is obtained. All IL-3 activity is found intracellularly. In those cases it seems that besides precursor IL-3, mature IL-3 (15 kd) has been formed in the cell. Thus, some transport across the membrane might have taken place, but the protein is not transported across the cell wall. However, using the alpha-amylase regulation and secretion signals (pGB/IL-317), most of the IL-3 activity appeared to be secreted into the culture medium. Besides a degradation product, two proteins are detected in the supernatant, one of about 15 kd and one of about 17 kd, most probably mature IL-3 and precursor IL-3, respectively. These data indicate that both processing sites, viz., the alpha-amylase and the hmulti-CSF processing site, are used. In the cell the most abundant product is precursor IL-3 containing the alpha-amylase signal sequence (the 20 kd protein) as shown by Western blotting. Sometimes a degradation product is detected.

EXAMPLE 6

Construction of Kluyveromyces Lactis Expression Vectors

A. Construction of pGB/IL-316

A DNA fragment comprising the Tn5 gene (Reiss et al., 1984) conferring resistance to gentamycin G418, under the direction of the alcohol dehydrogenase I (ADHI) promoter from *S. cerevisiae,* similar to that described by Bennetzen and Hall (1982), was inserted into the SmaI site of pUC19 (Yanisch-Perron et al., 1985). An *E. coli* strain containing the obtained plasmid, pUC-G418, was deposited with CBS on Dec. 4, 1987, under CBS872.87.

Into the XbaI-HindIII cleaved pUC-G418 vector an XbaI-HindIII fragment from plasmid pGB903 (U.S. patent application Ser. No. 07/078,539) containing the *K. lactis* lactase promoter and calf prochymosin DNA was inserted, resulting in plasmid pGB/IL-314.

Figure 21:
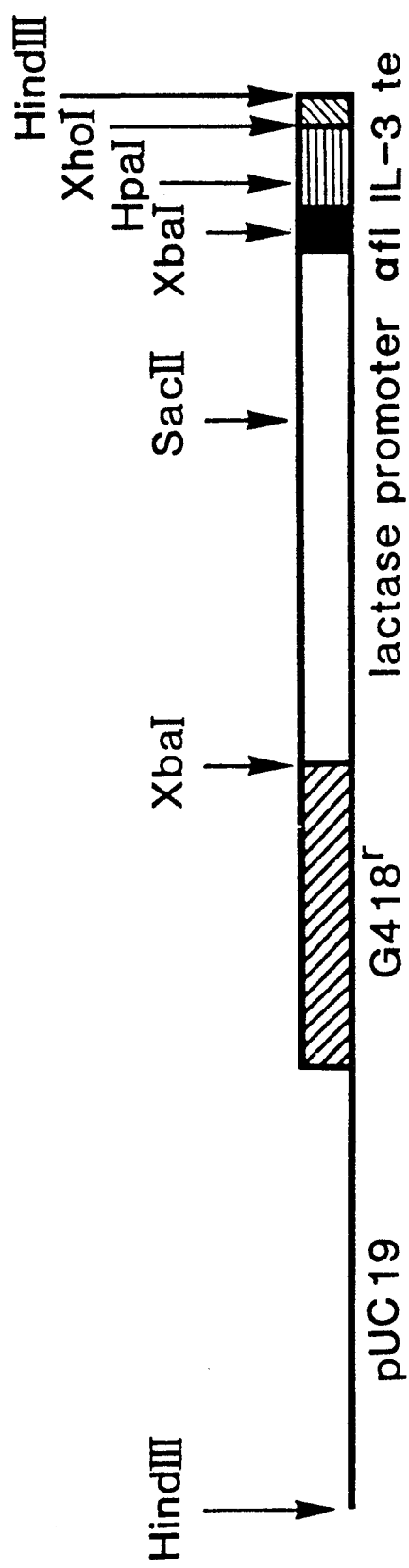
FIG. 21 shows a schematic representation of plasmid pGB/IL-316 construction.

The SalI-HindIII fragment from this plasmid was replaced by a synthetic DNA fragment containing a small multiple cloning site and the lactase terminator (see FIGS. 21, 22). The resulting plasmid is designated pGB/IL-315.

In the SacII-XhoI cleaved pGB/IL-315 vector the following fragments were ligated:

1. The SacII-XbaI fragment from pKS105 (U.S. patent application Ser. No. 07/078,539; U.S. patent application Ser. No. 07/078,539) carrying the 3' part of the lactase promoter and the 5' part of the alpha-factor signal sequence of *S. cerevisiae.*

2. A synthetic oligonucleotide comprising the 3' part of the alpha-factor signal sequence starting at the XbaI site and the 5' part of the mature hIL-3 cDNA sequence up to the 5' half of the HpaI site (amino acid residue 14).

3. The HpaI-XhoI fragment carrying most part of the hIL-3 cDNA sequence (residue 15–133 plus the 3' noncoding region). The resulting plasmid, designated pGB/IL-316, is depicted schematically in FIG. 21. The complete vector sequence from the SacII site in the lactase promoter sequence up to the HindIII site at the end of the synthetic terminator is given in FIG. 22.

FIG. 22 shows the nucleotide sequence of plasmid pGB/IL-316 between the unique SacII site in the lactase promoter and the HindIII site behind the terminator (residues 4457 to 7204). Residues 4457 to 6100 compromise the lactase promoter sequence. Residues 6101 to 6355 compromise the alpha factor signal sequence. Residues 6356 to 7115 compromise the sequence for mature human IL-3 plus the 3' noncoding cDNA sequence. Residues 7116 to 7204 compromise the synthetic terminator sequence.

B. Construction of pGB/IL-318

An expression vector similar to pGB/IL-316 was constructed in which the coding information for the alpha factor signal sequence of *S. cerevisiae* was replaced by the alpha-factor signal sequence of *K. lactis* (U.S. patent application Ser. No. 07/078,539). The remaining part of the plasmid is identical to pGB/IL-316. The sequence of pGB/IL-318 between the SacII site in the lactase promoter and the HindIII site behind the terminator (residues 4457 to 7190) is given in FIG. 23.

Residues 4457 to 6087 comprise the sequence of the lactase promoter and a small linker sequence. Residues 6088 to 6342 comprise the *K. lactis* alpha factor signal sequence. Residues 6343 to 7102 comprise the sequence for mature human IL-3 plus the 3' noncoding cDNA sequence. Residues 7103 to 7190 comprise the synthetic terminator sequence.

C. Transformation of Kluyveromyces Lactis and Analysis of Secreted hIL-3

Plasmid pGB/IL-316 and pGB/IL-318 was digested at the unique SacII site in the lactose promoter region, and used to transform *K. lactis* strain CBS 2360 (see U.S. patent application Ser. No. 07/078,539). Integration of the plasmids is thus targeted to the chromosomal lactase gene promoter region. The resulting G418-resistant transformants were grown to saturation in liquid YEPD medium, and the culture supernatants and cell lysates were assayed for IL-3 activity using the AML cell DNA synthesis assay.

Virtually all IL-3 appeared to be secreted into the culture medium, and to be active. The proteins from the culture supernatant were precipitated using ethanol and analyzed using denaturing polyacrylamide gel electrophoresis followed by Western blotting. The predominant product has an apparent MW of about 21 kd, whereas also a distinct band at about 15 kd is observed. The latter product most probably corresponds to the mature unglycosylated IL-3, whereas the 21 kd product is the product carrying core glycosylation at the two potential glycosylation sites. Incubation with Endoglycosidase H results in a protein migrating in the 15 kd range, suggesting that all IL-3 is processed correctly during the secretion process and that the bulk of the protein is being glycosylated.

EXAMPLE 7

Construction of a Saccharomyces Cerevisiae Expression Vector

A. Construction of pGB/IL-319

First an expression vector called pGB/TEFact was constructed On this pTZ18R (Pharmacia)-derived plasmid the *S. cerevisiae* translation elongation factor (EF-1alpha) promoter sequence which was cloned and sequenced as described (Najata et al., 1984; Nagashima et al., 1986), is coupled by means of a small SalI-BglII-XhoI linker to the *S. cerevisiae* actin transcription terminator sequence (Gallwitz and Sures, 1980), which was synthesized using an Applied Biosystems DNA synthesizer. The sequence of the expression cassette is given in FIG. 24. Residues 1 to 949 comprise the EF-1alpha promoter. Residues 950 to 967 comprise the sequence of the SalI-BglII-XhoI linker. Residues 968 to 1113 comprise the actin terminator sequence.

The unique SmaI site in pGB/TEFact was used to introduce the G418 resistance cassette described in Example 6. The resulting plasmid was called pGB/TEFactG418.

Finally, the hIL-3 expression vector pGB/IL-318 was constructed by introduction of the following DNA sequences into the SalI-XhoI-cleaved pGB/TEFactG418 plasmid:

1. The SalI-NruI fragment from pGB/IL-316 carrying the *S. cerevisiae* alpha factor signal sequence and the hIL-3 coding sequence up to the NruI site.
2. A synthetic NruI-XhoI DNA fragment comprising the remaining nucleotides coding for hIL-3 and the XhoI recognition sequence immediately following the TGA stop codon.

B. Transformation of Saccharomyces Cerevisiae and Analysis of Secreted hIL-3

Plasmid pGB/IL-319 was cleaved at the unique EcoRI site in the EF-1alpha promoter. Integration of the plasmid is thus targeted to the chromosomal EF-1alpha region. *S. cerevisiae* wild-type strain D273-103 (alpha; ATCC 25657) was transformed as described for *K. lactis* (U.S. patent application Ser. No. 07/078,539). The G418-resistant colonies were picked, and transformants were given to saturation in liquid YEPD medium. The culture supernatant was assayed for hIL-3 activity using the AML assay. The protein produced by *S. cerevisiae* was found biologically active.

The proteins from the supernatant were precipitated using ethanol and subsequently analyzed by polyacrylamide gel electrophoresis followed by Western blotting. Two prominent products could be distinguished on the Western blot, a 21 kd glycosylated product and an unglycosylated product of about 15 kd.

EXAMPLE 8

Construction of Mammalian Expression Vectors

The BPV genome encodes 3 proteins with sequences of the E2 open reading frame called E2-ta, E2-tr and E8/E2 respectively (Lambert et al., 1988). The ATG codon at position 3091-3093 may be changed into either an GCG (Ala) or an ACG (Thr), thereby on the one hand prohibiting the translation initiation of the E2-tr protein, and on the other hand, substituting Met$^{162}$ in E2-ta with Ala$^{162}$ or Thr$^{162}$. The BPV genome in pGB/IL-328 and pGB/IL-330 may be exchanged by the E2-tr mutant BPV genomes. The equivalents of pGB/IL-328 are designated pGB/IL-331 (Ala) and pGB/IL-332 (Thr). The equivalents of pGB/IL-330 are designated pGB/IL-333 (Ala) and pGB/IL-334 (Thr). The new expression vectors can be introduced into C127 and CHO cells as described. The level of hIL-3 production is expected to be substantially raised in both cell types with respect to the C127-pGB/IL-328, CHO-pGB/IL-328 and C127-pGB/IL-330, CHO-pGB/IL-330 combinations respectively.

The IL-3 present in the conditioned media of the established cell lines will show high activity in the biological assays described in WO 88/04691.

EXAMPLE 9

Purification of hIL-3 from Heterologous Expression Systems

A. Purification of hIL-3 from Bacillus licheniformis T9 (pGB/IL-322)

In order to obtain highly purified and homogeneous hIL-3 from *Bacillus licheniformis* T9 containing plasmid pGB/IL-322, isolation procedures were developed that offer extended possibilities for upscaling. Cell-free medium from *B. licheniformis* T9 was brought to 1M $(NH_4)_2SO_4$ and adjusted to pH 7.0 with NaOH and loaded on a column of Fractogel TSK-Butyl 650C, equilibrated in 1M $(NH_4)_2SO_4$ in 10 mM Tris-HCl buffer, pH 7.0. One mM phenylmethylsulfonylfluoride (PMSF) was used as a proteinase inhibitor. Whereas most of the protein was found in the run-through fractions, hIL-3 was adsorbed to the column. After extensive washing of this column with the same buffer, hIL-3 was eluted in a gradient from 1M to 0M $(NH_4)_2SO_4$ in 10 mM Tris-HCl, pH 7.0. The hIL-3-enriched fractions were concentrated by $(NH_4)_2SO_4$ precipitation at 70% saturation, and partly desalted by dialysis against water (up to a conductivity that was identical or lower than the conductivity of 20 mM Tris-HCl, pH 7.8) and loaded at pH 7.8 on a column of Fractogel TSK-DEAE 650M, equilibrated in 20 mM Tris-HCl, pH 7.8. Again, most of the hIL-3, now found in the run-through fractions, could be separated from the contaminating protein that remained bound to the column. For a final isolation procedure, the hIL-3-containing solution was concentrated (either by adsorption and separation on a small column of Fractogel TSK-Butyl 650C as described above, or by $(NH_4)_2SO_4$ precipitation) and purified to homogeneity by gel filtration on Biogel A (0.5M; 100–200 mesh) with 200 mM NaCl in 20 mM Tris-HCl, pH 7.0, as the running buffer. hIL-3 obtained at this stage of the purification consisted of several hIL-3 degradation products and was free from contaminating proteins, as was determined by SDS-PAGE followed by silver staining and by immunoblotting using anti-hIL-3 antibodies. The observed different molecular forms of hIL-3 most probably are the result of proteolytic degradation of the proteins during the fermentation procedure.

Further analysis of this preparation of hIL-3 resulted in single A280-detectable peak elutions after separation by reverse-phase HPLC (using a gradient from 40–60% acetonitrile in 0.1% trifluoroacetic acid, TFA), gel filtration on an HPLC TSK G2000SW column (7.5×600 mm) and cation-exchange chromatography on Fractogel TSK CM 650M. (IL-3 was loaded at pH 5.0 and eluted in a phosphate-buffered gradient from pH 5.0 to pH 9.0.)

If hIL-3 degradation products were present in the starting medium obtained from *B. licheniformis* T9, selective removal of these proteolytic degradation products from the fraction of interest was carried out by the following purification procedures.

hIL-3 enriched fractions derived from the hydrophobic interaction column above were concentrated as described, adjusted to pH 7.8 and brought to a conductivity of 0.7 mS. hIL-3 was then loaded on a column of Q Sepharose Fast-Flow (50×5 cm) that was equilibrated in a Tris buffer with identical pH and conductivity (with a flow of about 300ml/h). In this purification step, the volume of the concentrated solution with hIL-3 that was loaded did comprise just 3-4% of the total column volume. All active forms of hIL-3 were found in the run-through fractions. The major form of hIL-3 was separated from other hIL-3-like smaller proteins that were also positive in western blotting using antihuman IL-3 antibodies. When contaminating hIL-3 degradation products were still present in the peak fraction of interest, this isolation procedure was repeated. Amino-terminal sequence analysis of the first 30 amino acids of the major form of hIL-3 revealed a sequence that is identical with the mature protein.

Chromatography on hydroxylapatite also turned out to be an effective method for the isolation of several *B. licheniformis* hIL-3 degradation products. hIL-3 was loaded on a Biogel hydroxylapatite column in 10 mM $NaH_2PO_4$, 0.01 mM $CaCl_2$, 0.02% $NaN_3$, pH 6.8, and was eluted from the column in a gradient from 10 to 350 mM $NaH_2PO_4$ in the same solution. This method was effective on both an analytical and a preparative scale. All hIL-3 preparations obtained were positive in the AML assay as described herein.

hIL-3 degradation products from *B. licheniformis* T9 could also be separated by means of chromatofocussing on the polybuffer exchanger pBE94. By the application of a pH-gradient onto the column, different hIL-3 degradation products were eluted between pH 6.5 and pH 8.5.

A similar isolation procedure based on hydrophobic interaction of hIL-3 from *B. licheniformis* on octyl-Sepharose instead of Fractogel TSK-Butyl, was performed. hIL-3 was eluted by the application of a gradient from 0% (v/v) to 100% (v/v) ethylene glycol which illustrates the stronger binding characteristics of the former matrix.

B. Large-Scale Purification of hIL-3 from *Bacillus licheniformis* T9 (pGB/IL-322)

hIL-3 was purified from *B. licheniformis* T9 (pGB/IL-322) using the following four step large-scale purification scheme.

Step One: Hydrophobic Interaction Chromatography

Figure 26:
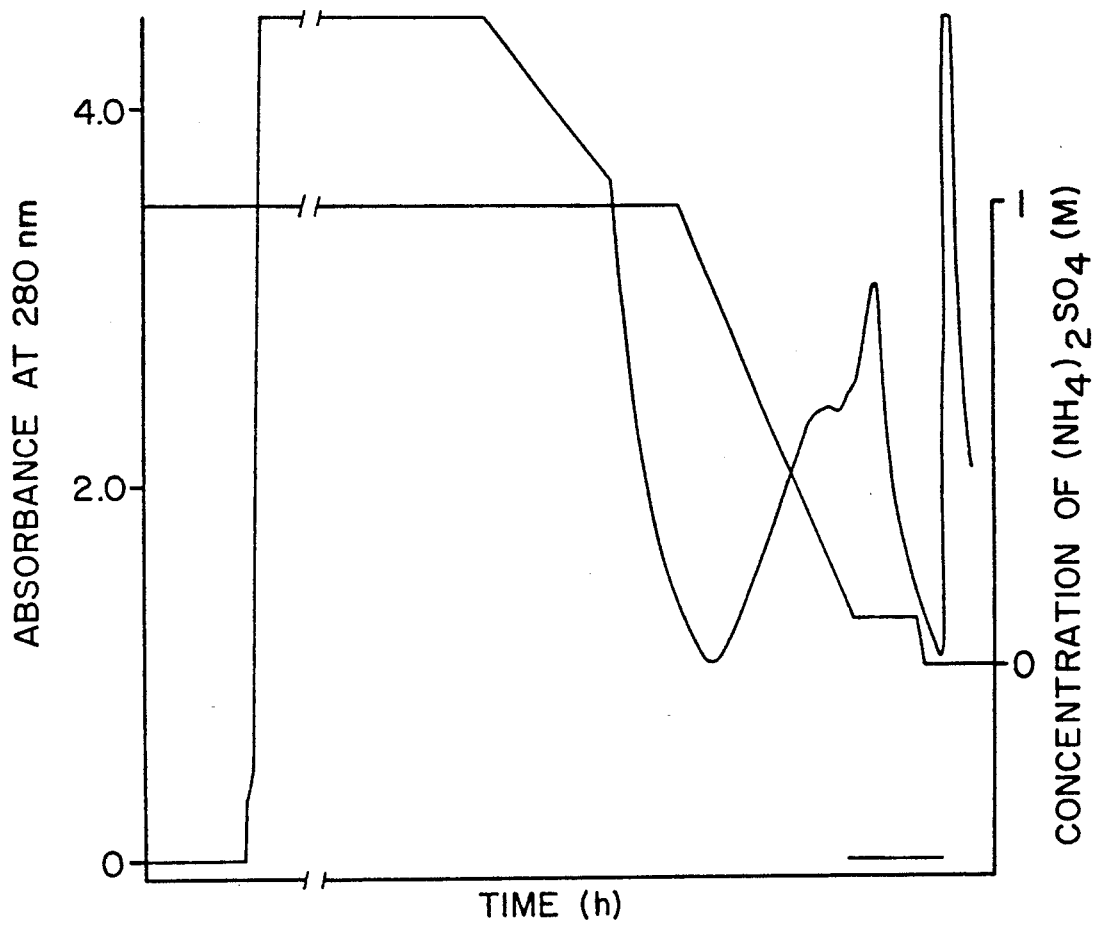
FIG. 26 shows the elution profile of the hydrophobic interaction chromatography of hIL-3 from *Bacillus licheniformis* T9 on Fractogel TSK-butyl 650C (d×h 25×8 cm). The hIL-3 containing fractions are indicated with a horizontal bar.

The cell-free supernatant derived from 6 fermentation runs of *B. licheniformis* T9 (see WO 88/04691), having a total volume of 48 liters, was brought to 1M $(NH_4)_2SO_4$, pH 7.0. Human IL-3 was adsorbed on a Fractogel TSK-butyl 650C column (d×h 25×8 cm) equilibrated with 1M $(NH_4)_2SO_4$ in Tris, pH 7.0 (q 8 l/h). The column was extensively washed with the same buffer. hIL-3 was eluted with a linear salt gradient from 1.0–0.1M $(NH_4)_2SO_4$ in 10 mM Tris, pH 7.0 (see FIG. 26). The hIL-3 enriched fractions were further concentrated by $(NH_4)_2SO_4$ precipitation at 60% saturation and the precipitate was desalted by dialysis (Spektra/Por, cutoff 3.500D) against Milli-Q water up to a conductivity of 0.70 mS or less.

Step Two: Anion Exchange Chromatography (First Run)

Figure 27:
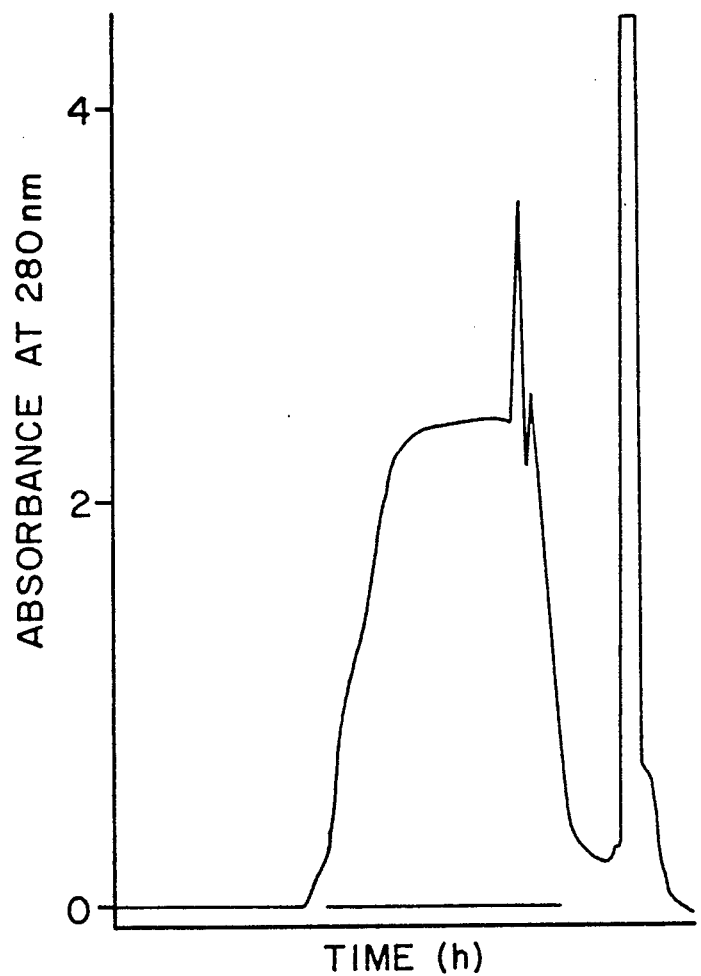
FIG. 27 shows the elution profile of the anion exchange chromatography (first run) of hIL-3 from *Bacillus licheniformis* T9 on Q-Sepharose Fast Flow (d×h 10×11 cm).

The hIL-3 enriched solution was brought to pH 7.8 using solid Tris and to a final conductivity of less than 0.70 mS. Subsequently it was run on a Q-Sepharose Fast Flow column (d×h 10×11 cm, q 3 l/h), equilibrated in a Tris buffer, pH 7.8, with a conductivity of less than 0.70 mS. hIL-3 was collected in the run-through fraction. Most of the contaminating protein was bound to the column (see FIG. 27). hIL-3 was concentrated to 25–30 mg/ml by ultrafiltration (Amicon, ym5 filter).

Step Three: Anion Exchange Chromatography (Second Run)

Figure 28:
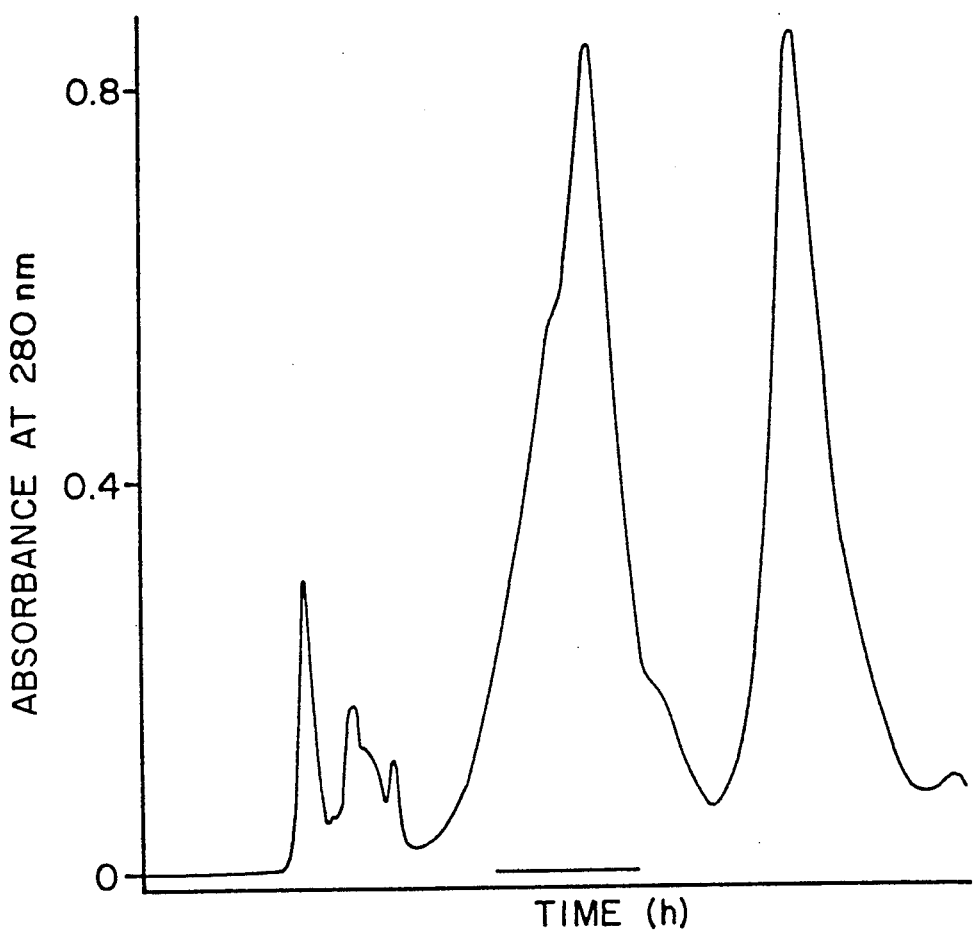
FIG. 28 shows the elution profile of the anion exchange chromatography (second run) of hIL-3 from *Bacillus licheniformis* T9 on Q-Sepharose Fast Flow (d×h 5×90 cm).

Sixty milliliters (containing 1.5–1.8 g hIL-3) of the solution obtained from the previous step was run on a Q-Sepharose Fast Flow column (d×h 5×90 cm, q 0.3 l/h). Several peaks with hIL-3 activity were detected in the run-through fractions (see FIG. 28). Thus, the hIL-3 protein fraction of interest was separated from hIL-3 degradation products. The hIL-3 was concentrated as described above.

Step Four: Gel Filtration Chromatography

Figure 29:
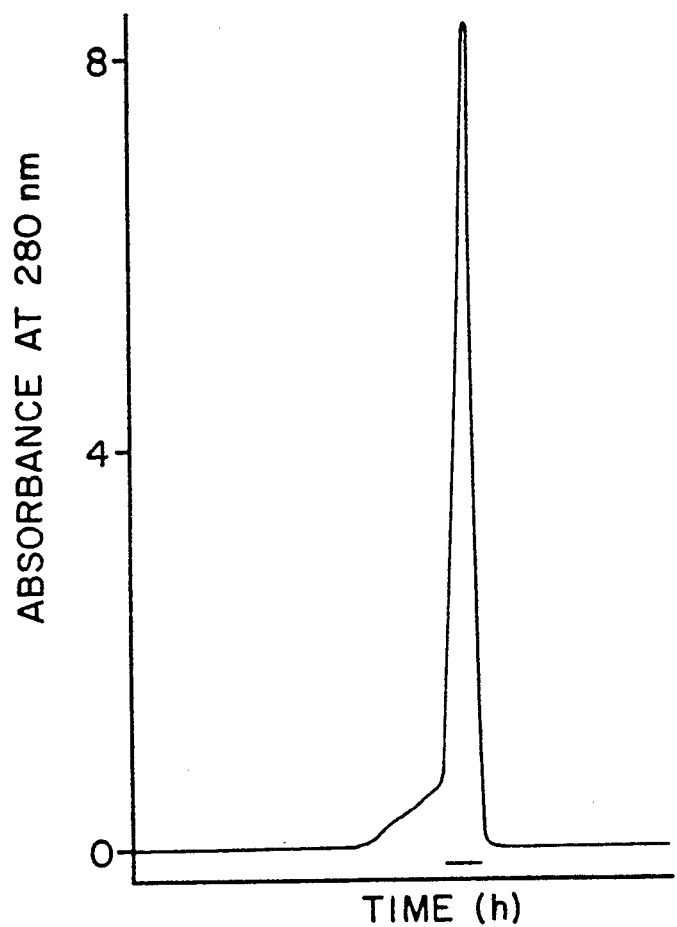
FIG. 29 shows the elution profile of the gel filtration chromatography of hIL-3 from *Bacillus licheniformis* T9 on Sephacryl S100 HR (d×h 5×90 cm).

Approximately 0.9 g hIL-3 (obtained from the above steps) was run on a Sephacryl S100 HR column (d×h 5×90 cm, q 0.15 l/h), equilibrated in 10 mM $NaH_2PO_4$, 140 mM NaCl, pH 7.0. The hIL-3 was collected in a single peak which was separated from a small amount of hIL-3 aggregates eluting just before the hIl-3 (see FIG. 29).

hIL-3 obtained by this purification procedure was free from detectable amounts of contaminating protein and nucleic acid. The solution containing hIL-3 was desalted and subsequently concentrated by ultrafiltration to the appropriate concentration.

C. Purification of hIL-3 from *E. coli* (pGB/IL-302)

hIL-3 was purified from *E. coli* as follows. For the isolation of a lacZ/hIL-3 fusion product that was intracellularly expressed in *E. coli* (pGB/IL-302) and stored in inclusion bodies, the cells were lysed in a Tris buffer, pH 8.0, containing 1% (v/v) octanol, 1% (w/v) Tx100, 0.1% (w/v) EDTA, and 0.025% (w/v) lysozyme. 1 mM PMSF was used as a proteinase inhibitor. After an extra incubation with DNAse and $Mg^{2+}$, the crude inclusion bodies were centrifuged (10 min., 4000 g) and washed in the same Tris buffer as above. After an extra centrifugation procedure (30 min., 10,000 g), inclusion body-derived protein was solubilized in 8 M urea in Tris buffer under reducing conditions (5 mM dithiothreitol, DTT). Finally, centrifugation (30 min., 27,000 g) resulted in a supernatant with most of the hIL-3 that was originally present in the inclusion bodies. This solution of hIL-3 was adjusted to pH 5.0 and loaded on a Fractogel TSK CM 650M column, equilibrated in a buffer containing 8M urea, 5 mM DTT, pH 5.0. IL-3 was eluted from this column by a linear salt gradient from 0 to 300 mM NaCl in the same buffer. IL-3 from *E. coli*, renaturated and solubilized in urea and partly purified by ion-exchange chromatography, is positive in an AML assay.

D. Purification of hIL-3 from *K. lactis* (pGB/IL-316) and *S. cerevisiae* (pGB/IL-316)

hIL-3 was purified from yeast as follows. After centrifugation of a culture of *K. lactis* (pGB/IL-316), the hIL-3-containing supernatant was filtrated for residual cell removal, brought to a concentration of 1M $(NH_4)_2SO_4$, and adjusted to pH 7.0. (1 mM PMSF was used as a proteinase inhibitor.) This solution was loaded on a column of octyl-Sepharose equilibrated in 1M $(NH_4)_2SO_4$ in phosphate buffer, pH 7.0. Whereas most of the protein was found in the run-through fractions, hIL-3 was abandoned to the column. After a washing procedure with the same buffer, hIL-3 was partly released from the column in a gradient from 1M to 0M $(NH_4)_2SO_4$ in phosphate buffer, pH 7.0.

The major part of hIL-3 that was still adsorbed to the column was eluted by the application of a gradient from 0% (v/v) to 100% (v/v) ethylene glycol. The technique of hydrophobic interaction of hIL-3 on octyl-Sepharose (or Fractogel TSK-butyl) proved to be a highly efficient first isolation procedure. This technique, followed by ion-exchange chromatography and gel filtration, resulted in a homogeneous preparation of hIL-3 from *K. lactis*. In a similar procedure using the medium from *S. cerevisiae* (pGB/IL-316), hIL-3 was also eluted from octyl-Sepharose in a gradient from 0% (v/v) to 100% (v/v) ethylene glycol.

In an alternative procedure, hIL-3 was isolated from the cell-free medium of a culture of *K. lactis* by first performing $(NH_4)_2SO_4$ precipitation (at 75% saturation). The collected precipitate was resuspended in, and dialyzed against, phosphate buffer. This method resulted in precipitation of most hIL-3 included in just a minor part of the total amount of protein that was originally present. The hIL-3-containing solution was adjusted to pH 5.0 and loaded on a Fractogel TSK-CM 650M cation-exchange column, equilibrated in the same buffer. Whereas all hIL-3 was adsorbed to the column, most of the contaminating protein was found in the run-through fractions. hIL-3 was eluted from the column by the application of a gradient from 0 mM to 300 mM NaCl in the same buffer. Fractionated hIL-3 obtained by this two-step procedure is close to homogeneity. As a result of the nature of glycosylation, inherent when using *K. lactis* as the expression system, hIL-3 purified to homogeneity was composed of different forms of the protein with respect to molecular weight. All hIL-3 preparations obtained from the above-mentioned yeast expression systems are positive in the AML assay.

hIL-3 from *K. lactis* obtained after purification on Fractogel TSK-CM 650M as described above, surprisingly showed a low but distinct binding affinity for heparin-Sepharose as was detected by SDS-PAGE and immunoblotting. The affinity of hIL-3 for heparin may suggest a binding in vivo to similar matrices (the glycosaminoglycans, for instance) that are present within the human bone marrow stroma. Binding of hIL-3 to such a matrix may be part of its physiological function. The presence of heparin-like and/or glycosaminoglycan-like binding site(s) on growth factors or other proteins could be an important mechanism for the in vivo targeting of such proteins to specific matrices within the bone marrow stroma or elsewhere in the body where their action is required. The development of second generation proteins with new or better binding sites for the above-mentioned matrices could become a potent tool in the formulating and targeting of pharmaceutical proteins.

E. Purification of hIL-3 from Mammalian Cell Cultures hIL-3 obtained from a mammalian cell culture was purified from the medium by using similar methods as described for the purification of hIL-3 from *B. licheniformis*. Medium from transformed C127 cells containing pGB/IL-328 was brought to 1M $(NH_4)_2SO_4$, adjusted to pH 7.0 with NaOH, and loaded on a Fractogel TSK-Butyl 650C column (1 mM PMSF was used as a proteinase inhibitor). hIL-3-enriched fractions (with about 10% of total protein that was loaded on the column) were eluted in a gradient from 1M to 0M $(NH_4)_2SO_4$ in 10 mM Tris-HCl, pH 7.0. These fractions were concentrated by $(NH_4)_2SO_4$ precipitation at 60% saturation. The protein precipitate was dissolved and dialyzed against $H_2O$, after which 20 mM Tris-HCl, pH 7.8, was added up to a conductivity of 1.4 mS or less. The hIL-3 preparation was subsequently loaded on a Fractogel TSK-DEAE 650M column. hIL-3 was partly found in the run-through fractions and was also eluted in a gradient from 0 to 200 mM NaCl. Most of the contaminating proteins bound to the column and eluted after the hIL-3 fractions.

Again this two-step procedure, combined with $(NH_4)_2SO_4$ precipitation, resulted in a highly concentrated and purified preparation of hIL-3.

EXAMPLE 10

In vivo Effect of hIL-3 in Chimpanzees

Figure 25:
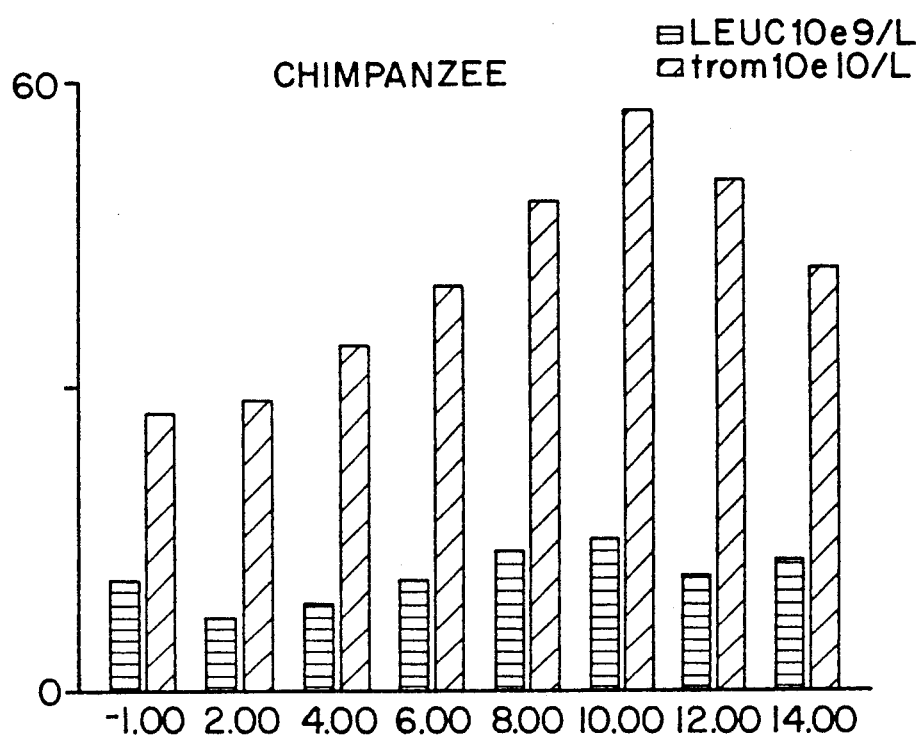
FIG. 25 shows the number of leukocytes and thrombocytes in chimpanzee blood after subcutaneous injection of 30 ug/kg IL-3, during day 0 to 6.

The recombinant hIL-3 produced by *B. licheniformis* cells was purified according to the procedure described in Example 9A. The IL-3 solution was then diluted in pyrogen free water to give the required final concentration. Chimpanzees were injected subcutaneously with this solution. Administration of 30 ug of IL-3 per kg per day for a period of seven days resulted in an increase of thrombocytes and a tendency to leucocytosis see FIG. 25). This surprising result of IL-3 activity as a single agent was unanticipated and may indicate a clinical application for IL-3 in thrombocytopenia.

REFERENCES

Bennetzen, J. L., and Hall, B. D., *J Biol Chem* (1982) 257:3018–3025.
Boom et al., *J Virol* (1986) 58:851–859.
Bron, S., and Venema, G., *Mutat Res* (1972) 15:1–10.
Buick, R. N., et al., *Blood* (1979) 54:95–104.
Chen, E. Y., et al., *Nature* (1982) 299:529–534.
Clark-Lewis, I., et al., *Science* (1986) 231:134–139.
DeLamarter, J. F., et al., *EMBO J* (1985) 10:2575–2581.
Delwel, R., et al., *Blood* (1986) 68:41–45.
Devereux, J., et al., *Nucleic Acid Res* (1984) 12:387–395.
Dijkema, R., et al., *EMBO J* (1985) 4:761–767.
Dorssers, L., et al., *Exp Hematol* (1984) 12:357.
Dorssers, L., et al., *Gene* (1987) 55:115–124.
EPA0244042, J. H. Van Ee, published Nov. 4, 1987.
EPA87201379.2, filed Jul. 20, 1987.
Fauser, A. A., and Messner, H. A. *Blood* (1978) 52:1243–1248.
Feinberg, A. P., and Vogelstein, B., *Anal Biochem* (1983) 132:6–13.
Fisher and Lerman, *Proc Natl Acad Sci USA* (1983) 80:1579–1583.

Fung, M. C., et al., *Nature* (1984) 307:233–237.
Gallwitz, D., and Sures, I., *Proc Natl Acad Sci USA* (1980) 77:2546–2550.
Garland, J. M., and Crompton, S., *Exp Hematol* (1983) 11:757–761.
Griffin et al., *Blood* (1986) 68:1232–1241.
Griffin and Lowenberg, *Blood* (1986) 68:1185–1195.
Gryczan, T. C., et al., *J Bacteriology* (1978) 134:318–329.
Gubler, U., and Hofmann, B. J., *Gene* (1983) 25:263–269.
Hapel, A. J., et al., *Blood* (1985) 65:1453–1459.
Higashi, Y., et al., *J Biol Chem* (1983) 258:9522–9529.
Hirt, B., *J Mol Biol* (1967) 26:365–367.
Huynh, T. V., et al., In "DNA Cloning" (1985) (Glover, D. M., ed.) IRL Press, Oxford, Vol. 1, pp 45–78.
Ihle, J. N., et al., *J Immunol* (1981), 129:2184–2189.
Ihle, J. N., et al., *J Immunol* (1982), 129:2431–2436.
Ihle, J. N., et al., In "Advances in Viral Oncology" (1984), (Klein, G., ed.), Raven Press, New York, Vol. 4, pp. 95–137.
Kawamura, F., and Doi, R. H., *J Bacteriol* (1984) 160:442–444.
Kindler, V., et al., *Proc Natl Acad Sci USA* (1986) 83:1001–1005.
Kozak, M., *Cell* (1986) 44:283–292.
Kreigler, A B., et al., *Blood* (1982) 60:503–508.
Lambert et al., *Ann Rev Genet* (1988), 22:235–258.
Law, M.-F., et al., *Proc Natl Acad Sci USA* (1981), 78:2727–2731.
Law, M.-F., et al., *Mol Cell Biol* (1983) 3:2110–2115.
Lemischka, I. R., et al., *Cell* (1986) 45:917–927.
Lipman, D. J., and Pearson, W. R., *Science* (1985) 227:1435–1441.
Lowenberg, B., and Dicke, K. A., *Exp Hematol* (1977) 5:319–331.
Lowenberg, B., et al., *Leuk Res* (1980) 4:143–149.
Lowenberg, B., et al., *Blood* (1982) 59:64??–645.
Lowenberg, B., and Bauman, J. G. J., *Blood* (1984) 66:1225–1232.
Majdic, O., et al., *Int J Cancer* (1984) 33:617–623.
Maniatis, T., et al., In "Molecular Cloning, A Laboratory Manual" (1982) Cold Spring Harbor Laboratories, New York.
March, C. J., et al., *Nature* (1985) 315:641–647.
McKenzie, T., et al., *Plasmid* (1986) 15:93–104.
McKenzie, T., et al., *Plasmid* (1987) 17:83–85.
Merchav and Wagemaker, *Int J of Cell Cloning* (1984) 2:356–367.
Metcalf, D., *Blood* (1986) 67:257–267.
Miyajima et al., *Gene* (1987), 58:273–281.
Miyatake, S., et al., *Proc Natl Acad Sci USA* (1985) 82:316–320.
Nagashima, K., et al., *Gene* (1986) 45:265–273.
Najata, S , et al., *EMBO J* (1984) 3:1825–1830.
Osinga, K. A., et al., *Nucleic AcidsRes* (1983) 11:8595–8608.
Perlman, D., and Halvorson, H. O., *J Mol Biol* (1983) 167:391–109.
Queen, C., and Korn, L. J. *Nucleic Acid Res* (1984) 12:581–599.
Reiss, B., et al., *EMBO J* (1984) 3:3317–3322.
Salfre, S., and Milstein, C., *Meth Enz* (1981) 73:3–75.
Sanger, F., et al., *Proc Natl Acad Sci USA* (1977) 74:5463.
Sarver et al., Papillomaviruses: Molecular and Clinical Aspects (1985), Alan R. Liss, Inc., pp. 515–527.
Scheven, B. A. A., *Nature* (1986) 321:79–81.
Schrader, J. W., et al., *Proc Natl Acad Sci USA* (1986) 83:2458–2462.
Seif and Cuzin, *Virology* (1977) 52:721–728.
Shaw, G., and Kamen, R., *Cell* (1986) 46:659–667.
Southern, P. J. and Berg, P., *J Mol Appl Genet* (1982), 1:327–341.
Staden, R., *Nucleic Acid Res* (1982) 10:2951–2961.
Stanley, E. R., et al., *Cell* (1986) 45:667–674.
Stanssens, P., et al., In "Protein Engineering and Site-Directed Mutagenesis." Twenty-Fourth Harden Conference. Program and Abstracts (1985) (Fersht, A. R., and Winter, G., eds).
Suarez Rendueles, M. P., et al., *FEBS Lett* (1981) 131:296–300.
Subramani, S., and Southern, P. J., *Anal Biochem* (1983) 135:1–15.
Swart, K., et al., *Blood* (1982) 59:816–821.
Swart, K., and Lowenberg, B., *Cancer Res* (1984) 44:657–660.
Till, J. E., and McCulloch, E. A., *Radiat Res* (1961) 14:213–222.
Touw, I., et al., *Blood* (1986) 68:1088–1094.
Touw, I., and Lowenberg, B., *Blood* (1985) 66:237–240.
Van den Berg, J. A., et al., U.S. application Ser. No. 078,539.
Van Ee, J. H., EPA0024.294.
Vieira, J., and Messing, J., *Gene* (1982) 19:259–268.
Von Heijne, G., *Eur J Biochem* (1983) 133:17–21.
Wagemaker, G., In "Bone Marrow Transplantation" (1986)(Van Bekkum, D. W., and Lowenberg, B., eds.) Marcel Dekker Inc. New York, 1–72.
Wagemaker, B., and Peters, M. F., *Cell Tiss Kinet* (1978) 11:45–56.
Wagemaker and Visser, *Cell Tiss Kinet* (1980) 13:505–517.
Whetton, A. D., and Dexter, T. M., *TIBS* (1985) 11:207–211.
Wigler, M., et al., *Cell* (1978) 14:725–731.
Wood, R. D., and Burki, J. H., *Mutat Res* (1984), 95:505.
Yang, Y.-C., et al., *Cell* (1986) 47:3–10.
Yanisch-Perron, C., et al., *Gene* (1985) 33:103–119.
Yokata, T., et al., *Proc Natl Acad Sci USA* (1984) 81:1070–1074.
Ziltener et al., *J Biol Chem* (1988), 263:14511–14517.
Zwarthoff, E. C., et al., *Nucleic Acid Res* (1985) 13:791–804.
Zyprian, E., and Matzura, H., *DNA* (1986) 5:219–225.

We claim:

1. A method of substantially purifying a protein having human IL-3 activity from a crude protein product obtained from a recombinant cell expressing a DNA sequence encoding a protein having the biological activity of human IL-3 said method comprising:
   (a) performing hydrophobic interaction chromatography on said protein product and collecting fractions comprising a protein having human IL-3 activity; followed by
   (b) performing ion exchange chromatography on the fractions collected in step (a) and collecting fractions comprising a protein having human IL-3 activity; followed by
   (c) performing gel filtration chromatography on the fractions collected in step (b) to yield a substantially pure potential having human IL-3 activity.

2. The method of claim 1 wherein said recombinant cell is a bacterial cell and said crude protein product is obtained from a lysate of said recombinant cell.

3. The method of claim 2 wherein said recombinant bacterial cell is *E. coli* transformed with pGB/IL-302.

4. The method of claim 1 wherein said crude protein product is obtained from substantially cell-free medium in which said recombinant cells have been cultured.

5. The method of claim 4 wherein said recombinant cell is *B. licheniformis* T9 transformed with pGB/IL-322.

6. The method of claim 4 wherein said recombinant cell is a yeast cell selected from the group consisting of *K. lactis* transformed with pGB/IL-316 and *S. cerevisiae* transformed with pGB/IL-316.

7. The method of claim 4 wherein said recombinant cell is a C127 cell transformed with pGB/IL-328.

8. A method for substantially purifying a protein having human IL-3 activity from a crude protein product obtained from a recombinant cell expressing a DNA sequence encoding a protein having the biological activity of human IL-3 said method comprising:

(a) precipitating said protein using $(NH_4)_2SO_4$; followed by (b) resuspending said protein-containing precipitate and performing hydrophobic interaction chromatography on resuspended protein and collecting fractions comprising protein having human IL-3 activity; followed by (c) performing ion exchange chromatography on the fraction collected in step (b) and collecting fractions comprising a protein having human IL-3 activity; followed by (d) performing gel filtration chromatography on the fractions collected in step (c) to yield a substantially purified protein having human IL-3 activity.

9. The method of claim 8 wherein said crude protein product is obtained from substantially cell free medium in which said recombinant cells have been cultured.

10. The method of claim 9 wherein said recombinant cell is *K. lactis* transformed with pGB/IL-316.

11. A method for substantially purifying a protein having human IL-3 activity from a crude protein product obtained from a recombinant cells expressing a DNA sequence encoding a protein having the biological activity of human IL-3 said method comprising:

(a) performing hydroxylapatite chromatography on said crude protein product and collecting fractions comprising a protein having human IL-3 activity; followed by (b) performing hydrophobic interaction chromatography on the fractions collected in step (a) and collecting fractions comprising protein having human IL-3 activity; followed by (c) performing ion exchange chromatography on the fractions collected in step (b) and collecting fractions comprising protein having human IL-3 activity; followed by (d) performing gel filtration chromatography on the fractions collected in step (c) to yield a substantially pure protein having human IL-3 activity.

12. The method of claim 11 wherein said crude protein product is obtained from substantially cell free medium in which said recombinant cells have been cultured.

13. The method according to any one of claims 1, 8 or 11 wherein the IL-3 protein is produced by the recombinant expression of a DNA sequence encoding the amino acid sequence shown as positions 1–133 in sequence "H" of FIG. 1.

14. The method according to any one of claims 1, 8 or 11 wherein the IL-3 protein is produced by the recombinant expression of a DNA sequence encoding the amino acid sequence shown as potassium 1–133 in sequence "H" of FIG. 1 with the proviso that said amino acid sequence contains a substitution selected from the group consisting of $trp^{13} \rightarrow arg^{13}$; $leu^9 \rightarrow pro^9$ and $trp^{13} \rightarrow arg^{13}$; and $met^3 \rightarrow thr^3$.

15. The method according to any one of claims 1, 8 or 11 wherein the IL-3 protein is produced by the recombinant expression of a DNA sequence encoding the amino acid sequence shown as positions 1–133 in sequence "H" of FIG. 1 wherein 1–14 amino acids at the N-terminus of said sequence are substituted by other amino acids.

16. The method according to claim 15 wherein the first 14 N-terminal amino acids of said sequence H are replaced by lacZ protein.

17. The method according to any one of claims 1, 8 or 11 wherein the protein or fragment thereof is purified from contaminating components of the growth medium after secretion from the recombinant cells.

18. The method according to claim 17 wherein said purified protein or fragment thereof is a substantially pyrogen-free product.

* * * * *